US008507466B2

(12) United States Patent  
Plat et al.

(10) Patent No.: US 8,507,466 B2  
(45) Date of Patent: Aug. 13, 2013

(54) OILS ENRICHED WITH DIACYLGLYCEROLS AND PHYTOSTEROL ESTERS AND UNIT DOSAGE FORMS THEREOF FOR USE IN THERAPY

(75) Inventors: Dorit Plat, Shimshit (IL); Dori Pelled, Hod Hasharon (IL); Avidor Shulman, Kiryat Tivon (IL); Gal Ben-Dror, Moshav Ofer (IL)

(73) Assignee: Enzymotec Ltd., Migdal Haemeq (IL)

( * ) Notice: Subject to any disclaimer, the term of this patent is extended or adjusted under 35 U.S.C. 154(b) by 169 days.

(21) Appl. No.: 12/655,240

(22) Filed: Dec. 23, 2009

(65) Prior Publication Data

US 2010/0184734 A1 Jul. 22, 2010

Related U.S. Application Data

(63) Continuation of application No. 11/396,257, filed on Mar. 31, 2006, now abandoned, which is a continuation-in-part of application No. 11/199,584, filed on Aug. 8, 2005, which is a continuation-in-part of application No. PCT/IL2004/000131, filed on Feb. 10, 2004.

(30) Foreign Application Priority Data

Feb. 10, 2003 (IL) .......................................... 154381  
Mar. 27, 2003 (IL) .......................................... 155136

(51) Int. Cl.  
*A61K 31/56* (2006.01)  
*A61P 3/00* (2006.01)

(52) U.S. Cl.  
USPC ...................................................... 514/171

(58) Field of Classification Search  
USPC ...................................................... 514/171  
See application file for complete search history.

(56) References Cited

U.S. PATENT DOCUMENTS

| | | |
|---|---|---|
| 4,064,236 A | 12/1977 | Dorn et al. |
| 4,457,917 A | 7/1984 | Schaller nee Kornmayer et al. |
| 4,639,435 A | 1/1987 | Fujii et al. |
| 4,755,383 A | 7/1988 | Fujii et al. |
| 4,863,860 A | 9/1989 | Halling et al. |
| 4,900,549 A | 2/1990 | De Vries et al. |
| 5,164,372 A | 11/1992 | Matsuo et al. |
| 5,298,246 A | 3/1994 | Yano et al. |
| 5,354,900 A | 10/1994 | Matsuo et al. |
| 5,418,219 A | 5/1995 | Ueda |
| 5,439,688 A | 8/1995 | Orsolini et al. |
| 5,554,378 A | 9/1996 | Uda et al. |
| 5,733,877 A | 3/1998 | Sato et al. |
| 5,736,519 A | 4/1998 | Deigin et al. |
| 5,843,499 A | 12/1998 | Moreau et al. |
| 5,998,396 A | 12/1999 | Nakano et al. |
| 6,025,348 A | 2/2000 | Goto et al. |
| 6,046,022 A | 4/2000 | Zhang et al. |
| 6,080,173 A | 6/2000 | Williamson, IV et al. |
| 6,106,886 A | 8/2000 | van Amerongen et al. |
| 6,113,972 A | 9/2000 | Corliss et al. |
| 6,129,924 A | 10/2000 | Maurel et al. |
| 6,129,945 A | 10/2000 | Awad et al. |
| 6,139,897 A | 10/2000 | Goto et al. |
| 6,303,586 B1 | 10/2001 | Mcpeak et al. |
| 6,326,050 B1 | 12/2001 | Goto et al. |
| 6,365,211 B1 | 4/2002 | Corrigan et al. |
| 6,589,588 B1 | 7/2003 | Wester et al. |
| 6,605,452 B1 | 8/2003 | Basheer |
| 6,620,440 B1 | 9/2003 | Hsia et al. |
| 6,667,068 B2 | 12/2003 | Smith et al. |
| 6,753,032 B1 | 6/2004 | Hirokawa et al. |
| 6,844,021 B2 | 1/2005 | Koike et al. |
| 7,008,661 B2 | 3/2006 | Koike et al. |
| 2001/0046548 A1 | 11/2001 | Berry et al. |
| 2002/0016314 A1 | 2/2002 | Schersl et al. |
| 2002/0025349 A1 | 2/2002 | Brindavanam et al. |
| 2002/0045000 A1 | 4/2002 | Nakajima et al. |
| 2002/0045773 A1 | 4/2002 | Ekblom et al. |
| 2002/0132035 A1 | 9/2002 | Tamarkin et al. |
| 2003/0031758 A1 | 2/2003 | Koss et al. |
| 2003/0108591 A1 | 6/2003 | Meijer et al. |
| 2003/0133965 A1 | 7/2003 | Bruno et al. |
| 2003/0158257 A1 | 8/2003 | Hase et al. |

(Continued)

FOREIGN PATENT DOCUMENTS

| | | |
|---|---|---|
| AU | 2003209617 | 8/2003 |
| BG | 104701 | 2/2002 |

(Continued)

OTHER PUBLICATIONS

Harris (Omega-3 long-chain PUFA and triglyceride lowering: minimum effective intakes (European Heart Journal Supplements (2001) 3 (Supplement D), D59-D61).*  
G. Assman et al., Am. J. Cardiol., 1996, pp. 1179-1184, vol. 77(14).  
M. Aviram and E. Kasem, Ann. Nutr. Metab., 1993, pp. 75-84, vol. 37.  
Awad et al., J. Nutr., 2000, pp. 2127-2130, vol. 130.  
Awad et al., Nutr. Cancer, 2000, pp. 74-78, vol. 36.  
Awad et al., Anticancer Res., 2000, pp. 821-824, vol. 20.  
Barr et al., Am. J. Med., 1951, pp. 480-493, vol. 11.  
Blonk et al., Am. J. Clin. Nutr., 1990, pp. 120-127, vol. 52.  
L. Calabresi et al., Metabolism, 2004, pp. 153-158, vol. 53(2).  
Calder, Ann. Nutr. Metab., 1997, pp. 203-234, vol. 41(4).  
Coste et al., Diabetes, 2003, pp. 2578-2584, vol. 52(10).  
Davidson et al., J. Ann. Coll. Nutr., 1997, p. 236, vol. 16.  
Dunstan et al., Diabetes Care, 1997, pp. 913-921, vol. 20.

(Continued)

*Primary Examiner* — San-Ming Hui  
*Assistant Examiner* — Kathrien Cruz  
(74) *Attorney, Agent, or Firm* — John P. White; Cooper & Dunham LLP

(57) ABSTRACT

Described herein are various lipid mixtures, more particularly special mixtures of fatty acids esters, which may be phytosterol esters and/or glyceride esters. Said mixtures are evaluated in the context of their ability to, upon consumption, affect the levels of circulating LDL and HDL particles, and their therapeutic effect on conditions associated with lipid metabolism, such as atherosclerosis, diabetes, metabolic disorders, etc. Compositions, dietary nutrients, food supplements and nutraceuticals comprising the herein described mixtures are also described.

21 Claims, 25 Drawing Sheets

(56) References Cited

U.S. PATENT DOCUMENTS

| | | |
|---|---|---|
| 2003/0225160 A1 | 12/2003 | Geerlings et al. |
| 2004/0105931 A1 | 6/2004 | Basheer et al. |
| 2004/0219188 A1 | 11/2004 | Comer et al. |
| 2005/0054621 A1 | 3/2005 | Gako-Golan et al. |
| 2005/0148666 A1 | 7/2005 | Hase et al. |
| 2006/0052351 A1 | 3/2006 | Plat et al. |
| 2006/0233863 A1 | 10/2006 | Plat et al. |

FOREIGN PATENT DOCUMENTS

| | | |
|---|---|---|
| CA | 2279402 | 9/1999 |
| CA | 2375023 | 7/2000 |
| CH | 692263 | 9/1975 |
| CN | 1348983 | 5/2002 |
| DE | 3909707 | 3/1989 |
| EP | 0203706 | 3/1986 |
| EP | 0203706 A2 | 12/1986 |
| EP | 0195311 | 6/1990 |
| EP | 0982315 A2 | 1/2000 |
| EP | 099039 | 4/2000 |
| EP | 1180545 | 5/2000 |
| EP | 1121928 | 8/2001 |
| EP | 1180545 A1 | 2/2002 |
| FR | 2761887 | 10/1998 |
| GB | 1405346 | 9/1975 |
| JP | 61-293341 | 12/1986 |
| JP | 2001-040388 | 2/2001 |
| JP | 2001-247473 | 9/2001 |
| JP | 2002-138297 | 5/2002 |
| JP | 2002-206100 | 7/2002 |
| JP | 2004-519232 | 2/2004 |
| JP | 2004-201672 | 7/2004 |
| JP | 2004-210652 | 7/2004 |
| KR | 20010035226 A | 5/2001 |
| WO | WO 96/14311 | 5/1996 |
| WO | WO 99/04782 | 2/1999 |
| WO | WO 99/13737 | 3/1999 |
| WO | WO 99/48378 | 9/1999 |
| WO | WO 99/59423 | 11/1999 |
| WO | WO 00/19842 | 4/2000 |
| WO | WO 00/56869 | 9/2000 |
| WO | WO 01/15552 | 3/2001 |
| WO | WO 01/32029 | 5/2001 |
| WO | WO 01/32035 | 5/2001 |
| WO | WO 01/72136 | 10/2001 |
| WO | WO 01/75083 | 10/2001 |
| WO | WO 02/11550 | 2/2002 |
| WO | WO 02/060272 | 8/2002 |
| WO | WO 02/100412 | 12/2002 |
| WO | WO 03/064444 | 8/2003 |
| WO | WO 2004/069150 | 8/2004 |

OTHER PUBLICATIONS

Fashing et al., Norm. Metab. Res., 1996, pp. 230-236, vol. 28.
Gerbi et al., J. Nutr., 1999, pp. 207-213, vol. 129.
Gylling H. and Miettinen T.A., Metabolism, 1999, pp. 575-580, vol. 48.
Hansen et al., Lipids, 1998, pp. 131-138, vol. 33.
Harris et al., J. Am. Coll. Nutr., 1991, pp. 220-227, vol. 10(3).
Hopkins and Barker, J. Lipid Res., 1986, pp. 1265-1277, vol. 27.
Horrobin, Prostaglandins Leukos. Essent. Fatty Acids, 1998, pp. 181-197, vol. 31.
Jellema et al., Eur. J. Clin. Invest., 2004, pp. 766-773, vol. 34(11).
Karpe, Intern. Med., 1999, pp. 341-355, vol. 246.
Katan et al., Mayo Clin. Proc., 2003, pp. 965-978, vol. 78.
Krauss, Diabetes Care, 2004, pp. 1496-1504, vol. 27.
Kris-Etherton P.M., Circulation, 2002, pp. 2747-2757, vol. 106(21).
Laasko et al., Metabolism, 1990, pp. 117-122, vol. 39.
Lemieux et al., Arch. Intern. Med., 2001, pp. 2685-2692, vol. 161(22).
Lou et al., Diabetes Care, 1998, pp. 717-724, vol. 21.
Mackness B. et al., Circulation, 2003, pp. 2775-2779, vol. 107.
Montori et al., Diabetes Care, 2000, pp. 1407-1415, vol. 23.
Mori T.A. et al., Am. J. Clin. Nutr., 2000, pp. 1085-1094, vol. 71.
Mori et al., Free Radic. Biol. Med., 2003, pp. 772-781, vol. 35(7).
Naghavi et al., Circulation, 2003, pp. 1664-1672, vol. 108.
Nissen et al., N. Eng. J. Med., 2005, pp. 29-38, vol. 352.
Relimpio et al., Diabetes Res. Clin. Practice, 2002, pp. 199-207, vol. 57(3).
Rifai and Ridker, Clin. Chem., 2001, pp. 28-30, vol. 47.
Ruiz-Gutierrez et al., Diabetologia, 1993, pp. 850-856, vol. 36.
Sanchez-Muniz et al., Eur. J. Nutr., 1999, pp. 20-27, vol. 38(1).
Sniderman et al., Ann. Int. Med., 2001, pp. 447-459, vol. 135.
Tilly-Kiese et al., J. Lipid Res., 1996, pp. 1569-1578, vol. 37.
Wilt et al., Cochrane Database Syst. Rev., 1998, vol. 3, Art. No. CD001042 DOI:10.1002/14651858.CD001042.
Amundsen AL. et al. (2002) Am. J. Clin. Nutr. 76: 338-344.
Austin M.A. et al. (1998) Am. J. Cardio. 81: 7B-12B.
Austin M.A. (1989) Am. J. Epidemiol. 129: 249-259.
Aviram M. (1993) Atherosclerosis 98: 1-9.
Aviram M. (1995) Isr. J. Med. Sci. 31: 241-249.
Aviram M. (1996) Europ. J. Clin. Chem. Clin. Biochem. 34: 599-608.
Aviram M. (1999) Antiox. Redox. Signal 1: 585-594.
Aviram M. (2000) Free. Radic. Res. 33: S85-97.
Aviram M. and Elias K. (1993) Ann. Nutr. Metabol. 37: 75-84.
Belinky, P.A. et al. (1998) Atherosclerosis 137: 49-61.
Belinky, P.A. et al. (1998) Free Radic. Biol. Med. 24: 1419-29.
Brown M.S. and Goldstein J.L. (1983) Annu. Rev. Biochem. 52: 223-261.
Ceconi, C. et al. (2003) Arch. Biochem. Biophys. \420: 217-221.
Chisolm G.M. and Steinberg D. (2000) Free Radic. Biol. Med. 28: 1815-1826.
Connor W.E. and Connor S.L. (1997) N. Engl. J. Med. 337: 562-563.
Connor W.E. and Connor S.L. (1997) N.Engl. J. Med. 337: 566-567.
Danesh J. et al. (2000) Circulation 102: 1082-1085.
Dhalla, N.S. et al. (2000) J. Hypertens. 18: 655-673.
Duckworth W.C. (2001) Curr. Atheroscler. Rep. 3: 383-91.
Expert Panel on Detection, Evaluation, and Treatment of High Blood Cholesterol in Adults (2001) J.A.M.A. 285: 2486-2497.
Gaullier J.M. et al. (2004) Am. J. Clin. Nutr. 79: 1118-1125.
Gerrity R.G. (1981) Am. J. Pathol. 103: 181-190.
Glass C.K. and Witztum J.L. (2001) Cell 104: 503-516.
Goupy, P. et al. (2003) Fr. J. Agricultural and Food Chemistry 51(3) 615-622.
Haisma, H. et al. (2005) J. Nutri. 135: 1889-1895.
Hallikainen M.A. et al. (2000) J. Nutr. 130: 767-776.
Heinecke, J.W. (2003) Am. J. Cardiol. 91: 12A-16A.
Johnston R.B. Jr. (1984) Methods Enzymol. 105: 365-9.
Jousilahtu et al. (1998) Circulation 97: 1087-1094.
Kaplan M. and Aviram M. (1999) Clin. Chem. Lab. Med. 37: 777-787.
Katan M.B. et al. (1997) N. Engl. J. Med. 337: 563-566.
Keidar S. (1998) Life Sci. 63: 1-11.
Kondo A. et al. (2002) J. Atheroscler Thromb. 9: 280-287.
Kris-Etherton P.M. et al. (1999) Am. J. Clin. Nutr. 70: 1009-1015.
Mackness, B. et al. (2003) Circulation 107: 2775-9.
Madigan C. et al. (2000) Diabetes care 23: 1472-1477.
Maritim A.C. (2003) J. Biochem. Mol. Toxico. 17: 24-38.
Moreau R. A. et al. (2002) Progress in Lipid Research 41: 457-500.
Normen L. et at. (2004) Curr. Med. Chem. Cardiovasc Hematol Agents 2: 1-12.
Rajagopalan S. et al. (1996) J. Clin. Invest. 97: 1916-1923.
Ross R. (1993) Nature 362: 801-809.
Schaffner T. et al. (1980) Am. J. Pathol. 100:57-80.
Stark, A.H. et al. (2002) Nutrition Reviews 60(6): 170-176.
Steinberg D. et al. (1989) N. Engl. J. Med. 320: 915-924.
Stone N.J. et al. (1996) Circulation 94: 3388-3391.
Taguchi, H. et al. (2000) J. Am. Coll. Nutr. 19: 789-796.
Thomas C.E. and Aust. S.D. (1986) Ann. Emerg. Med. 15(9): 1075-83.
Tsimikas S. et al. (2005) N. Engl. J. Med. 353: 46-57.
Tsuzura, S. et al. (2004) Metabolism 53: 297-302.
Vessby B. et al. (2001) Diabetologia 44: 312-319.
Visioli F. et al. (1995) Atherosclerosis 117: 25-32.
Walldius J. and Junger I. (2004) J. Intern. Med. 255: 188-205.
Yanagitani Y. et al. (1999) Hypertension 33: 335-9.
Yorek M.A. (2003) Free Radic. Res. 37: 471-80.

Mussner M.J. et al. (2002) Metabolism, Clinical and Experimental, vol. 51, No. 2, pp. 189-194.

Ling W.H. et al. (1995) Life Sciences, vol. 57, No. 3, pp. 195-206.

International Search Report for PCT/IL2004/000131 filed Feb. 10, 2004.

International Preliminary Report on Patentability for PCT/IL2004/000131 filed Feb. 10, 2004.

Office Action issued Jun. 23, 2009 in connection with U.S. Appl. No. 11/396.257, filed Mar. 31. 2006.

Ewart et al. "Fish Oil Containing Phytosterol Esters Alters Blood Lipid Profiles and Left Ventricle Generation of Thromboxane A2 in Adult Guinea Pigs 1,2." 2002 J. Nutr. 132: 1149-1152.

XP-002359318;Functional Oil shows Triple Action Against Heart Disease; Nov. 2, 2004.

XP-002359319; International Society for the Study of Fatty Acids and Lipids Issfal Newsletter. May 7-11, 2002. Montréal, Canada. Lipids. 2003 Winter;10(3).

XP009058643; Enzymotec Press Release. Apr. 23, 2003.

Kim et al. XP-002242960; Preparation method Fat oil composition containing high content. Jan. 18, 2011.

Zimmet P, Alberti KG, Shaw J. Global and societal implications of the diabetes epidemic. Nature. Dec. 13, 2001;414(6865):782-7. Review.

Ziv E, Kalman R, *Psammomys obesus*: Primary Insulin Resistance Leading to Nutritionally Induced Type 2 Diabetes. 327-342.

International Preliminary Examination Report issued Jan. 10, 2007 in connection with PCT International Application No. PCT/IL2005/000861.

International Search Report issued Aug. 1, 2011 in connection PCT International Application No. PCT/IL2005/000861.

Nagao T, Watanabe H, Goto N, Onizawa K, Taguchi H, Matsuo N, Yasukawa T, Tsushima R, Shimasaki H, Itakura H. Dietary diacylglycerol suppresses accumulation of body fat compared to triacylglycerol in men in a double-blind controlled trial. J Nutr. Apr. 2000;130 (4) :792-7.

Miettinen TA, Puska P, Gylling H, Vanhanen H, Vartiainen E. Reduction of serum cholesterol with sitostanol-ester margarine in a mildly hypercholesterolemic population. N Engl J Med. Nov. 16, 1995;333 (20) :1308-12.

http://en.wikipedia.org/wiki/docosahexaeoic_acid, Nov. 17, 2009.

http://en.wikipedia.org/wiki/eicosaoentaenoic_acid, Nov. 17, 2009.

http://lookwayup.com. Jun. 15, 2010.

http://diabetes.org. Jul. 2, 2010.

Russell et al. "Improvement of Vascular Dysfunction and Blood Lipids of Insulin-Resistant Rats by a Marine Oil-Based Phytosterol Compound" Lipids 37: 147-152 (2002).

Paul Jayaraj A, Tovey FI, Hobsley M. Duodenal ulcer prevalence: research into the nature of possible protective dietary lipids. Phytother Res. Apr. 2003;17(4):391-8.

Lichtenstein AH, Deckelbaum RJ. AHA Science Advisory. Stanol/sterol ester-containing foods and blood cholesterol levels. A statement for healthcare professionals from the Nutrition Committee of the Council on Nutrition, Physical Activity, and Metabolism of the American Heart Association. Circulation. Feb 27, 2001;103(8):1177-9.

Vuorio AF, Gylling H, Turtola H, Kontula K, Ketonen P, Miettinen TA. Stanol ester margarine alone and with simvastatin lowers serum cholesterol in families with familial hypercholesterolemia caused by the FH-North Karelia mutation. Arterioscler Thromb Vasc Biol. Feb. 2000;20(2):500-6.

Berger A, Jones PJ, Abumweis SS. Plant sterols: factors affecting their efficacy and safety as functional food ingredients. Lipids Health Dis. Apr. 7, 2004;1-19.

"Nutrition Principles and Recommendation in Diabetes." American Diabetes Association. 2004. pp. 1-42.

Awad AB, Fink CS. Phytosterols as anticancer dietary components: evidence and mechanism of action. J Nutr. Sep. 2000;130(9):2127-30. Review.

Baynes JW, Thorpe SR. Role of oxidative stress in diabetic complications: a new perspective on an old paradigm. Diabetes. Jan. 1999;48(1):1-9. Review.

Camino P, Moreda W., Cert A, Determination of diacylgycerol isomers in vegetable oils by solid-phase extraction followed by gas chromatography on a polar phase. Jur of Chromatography A, 1996;(721):305-314.

Carrero JJ, Baró L, Fonollá J, González-Santiago M, Martínez-Férez A, Castillo R, Jiménez J, Boza JJ, López-Huertas E. Cardiovascular effects of milk enriched with omega-3 polyunsaturated fatty acids, oleic acid, folid acid, and vitamins E and B6 in volunteers with mild hyperlipidemia. Nutrition. Jun. 2004;20 (6) : 521-7.

Gordon CM, DePeter KC, Feldman HA, Grace E, Emans SJ. Prevalence of vitamin D deficiency among healthy adolescents. Arch Pediatr Adolesc Med. Jun. 2004;158(6) :531-7.

Database FSTA Online! International Food Information Service (IFIS), Frankfurt-Main, DE; 2003, Blum M: "Vitamins, carotenoids and PUFA: key factors for functional foods." XP002354043.

Demonty I, Chan YM, Pelled D, Jones PJ. Fish-oil esters of plant sterols improve the lipid profile of dyslipidemic subjects more than do fish-oil or sunflower oil esters of plant sterols. Am J Clin Nutr. Dec. 2006;84(6) :1534-42.

Franz et al. American Diabetes Association Task Force for Writing Nutrition Principles and Recommendations for the Management of Diabetes and Related Complications. American Diabetes Association position statement: evidence-based nutrition principles and recommendations for the treatment and prevention of diabetes and related complications. J Am Diet Assoc. Jan. 2002;102(1) :148-198.

Griendling KK, FitzGerald GA. Oxidative stress and cardiovascular injury: Part II: animal and human studies. Circulation. Oct. 28, 2003;108(17):2034-40. Review.

Grundy SM. Obesity, metabolic syndrome, and cardiovascular disease. J Clin Endocrinol Metab. Jun. 2004;89(6):2595-600.

Hayes, C. Diabetes Bars and Beverages: The Benefits and the Controversies. Diabetes Spectrum. Nov. 2002; 15: 11-4. (Exhibit. 59).

Gylling H, Miettinen TA. Cholesterol reduction by different plant stanol mixtures and with variable fat intake. Metabolism. May 1999; 48(5):575-80.

Hendriks HF, Weststrate JA, van Vliet T, Meijer GW. Spreads enriched with three different levels of vegetable oil sterols and the degree of cholesterol lowering in normocholesterolaemic and mildly hypercholesterolaemic subjects. Eur J Clin Nutr. Apr. 1999;53(4):319-27.

Intensive blood-glucose control with sulphonylureas or insulin compared with conventional treatment and risk of complications in patients with type 2 diabetes (UKPDS 33). UK Prospective Diabetes Study (UKPDS) Group. Lancet. Sep. 12, 1998;352(9131) :837-53.

Jones PJ, Demonty I, Chan YM, Herzog Y, Pelled D. Fish-oil esters of plant sterols differ from vegetable-oil sterol esters in triglycerides lowering, carotenoid bioavailability and impact on plasminogen activator inhibitor-1(PAI-1) concentrations in hypercholesterolemic subjects. Lipids Health Dis. Oct. 25, 2007;6:28.

Kalman R, Adler JH, Lazarovici G, Bar-On H, Ziv E. The efficiency of sand rat metabolism is responsible for development of obesity and diabetes. J Basic ClinPhysiol Pharmacol. Apr.-Jun. 1993;4 (1-2) :57-68.

Katan MB, Grundy SM, Jones P, Law M, Miettinen T, Paoletti R; Stresa Workshop Participants. Efficacy and safety of plant stanols and sterols in the management of blood cholesterol levels. Mayo Clin Proc . Aug. 2003; 78 (8) : 965-78 . Review.

Larkin M. Diet and exercise delay onset of type 2 diabetes, say US experts. Lancet. Aug. 18, 2001;358(9281) :565.

Law M. Plant sterol and stanol margarines and health. BMJ. Mar. 25, 2000;320(7238) :861-4.

Simons LA. Additive effect of plant sterol-ester margarine and cerivastatin in lowering low-density lipoprotein cholesterol in primary hypercholesterolemia. Am J Cardiol. Oct. 1, 2002;90(7) :737-40.

Logroscino G, Kang JH, Grodstein F. Prospective study of type 2 diabetes and cognitive decline in women aged 70-81 years. BMJ. Mar. 6, 2004;328(7439) :548-553.

Javed A M., Akhtar N, Jabbar A. XP-009058587; Fatty acid and lipid composition of sesamum indicum DC. Pak J Sci Incl Res 2000 43 (1) 23-25.

Maki et al Faseb J 15 (4) A301.

Noakes M, Clifton P, Ntanios F, Shrapnel W, Record I, McInerney J. An increase in dietary carotenoids when consuming plant sterols or stanols is effective in maintaining plasma carotenoid concentrations. Am J Clin Nutr. Jan. 2002;75(1):79-86.

Mussner MJ, Parhofer KG, Von Bergmann K, Schwandt P, Broedl U, Otto C. Effects of phytosterol ester-enriched margarine on plasma lipoproteins in mild to moderate hypercholesterolemia are related to basal cholesterol and fat intake. Metabolism. Feb. 2002;51(2):189-94.

Matsuzawa Y, Shimomura I, Nakamura T, Keno Y, Tokunaga K. Pathophysiology and pathogenesis of visceral fat obesity. Ann N Y Acad Sci. Jan. 17, 1995;748:399-406.

Richelle M, Enslen M, Hager C, Groux M, Tavazzi I, Godin JP, Berger A, Métairon S, Quaile S, Piguet-Welsch C, Sagalowicz L, Green H, Fay LB. Both free and esterified plant sterols reduce cholesterol absorption and the bioavailability of beta-carotene and alpha-tocopherol in normocholesterolemic humans. Am J Clin Nutr. Jul. 2004;80(1):171-7.

Murase T, Aoki M, Wakisaka T, Hase T, Tokimitsu I. Anti-obesity effect of dietary diacylglycerol in C57BL/6J mice: dietary diacylglycerol stimulates intestinal lipid metabolism. J Lipid Res. Aug. 2002;43(8):1312-9.

Murase T, Mizuno T, Omachi T, Onizawa K, Komine Y, Kondo H, Hase T, Tokimitsu I. Dietary diacylglycerol suppresses high fat and high sucrose diet-induced body fat accumulation in C57BL/6J mice. J Lipid Res. Mar. 2001;42(3):372-8.

Muskiet FA, Fokkema MR, Schaafsma A, Boersma ER, Crawford MA. Is docosahexaenoic acid (DHA) essential? Lessons from DHA status regulation, our ancient diet, epidemiology and randomized controlled trials. J Nutr. Jan. 2004;134(1):183-6.

Ohr, L.M. XP-009057108; Fats for Healthy Living. Products & Technologies; Nutraceuticals & Functional Foods. Jul. 2003; 57(7):91-96.

Bouic PJ. The role of phytosterols and phytosterolins in immune modulation: a review of the past 10 years. Curr Opin Clin Nutr Metab Care. Nov. 2001;4(6):471-5. Review.

Pollak OJ. Reduction of blood cholesterol in man. Circulation. May 1953;7(5):702-6.

Ostlund RE Jr. Phytosterols and cholesterol metabolism. Curr Opin Lipidol. Feb. 2004;15 (1):37-41. Review.

Risman. 1998. pp. 220-222.

Moreau RA, Whitaker BD, Hicks KB. Phytosterols, phytostanols, and their conjugates in foods: structural diversity, quantitative analysis, and health-promoting uses. Prog Lipid Res. Nov. 2002;41 (6):457-500. Review.

Meguro S, Higashi K, Hase T, Honda Y, Otsuka A, Tokimitsu I, Itakura H. Solubilization of phytosterols in diacylglycerol versus triacylglycerol improves the serum cholesterol-lowering effect. Eur J Clin Nutr. Jul. 2001;55(7):513-7.

de Jongh S, Vissers MN, Rol P, Bakker HD, Kastelein JJ, Stroes ES. Plant sterols lower LDL cholesterol without improving endothelial function in prepubertal children with familial hypercholesterolaemia. J Inherit Metab Dis. 2003;26(4):343-51.

Sarkkinen E, Schwab U, Niskanen L, Hannuksela M, Savolainen M, Kervinen K, Kesäniemi A, Uusitupa MI. The effects of monounsaturated-fat enriched diet and polyunsaturated-fat enriched diet on lipid and glucose metabolism in subjects with impaired glucose tolerance. Eur J Clin Nutr. Sep. 1996;50 (9):592-8.

Shafrir E, Gutman A. Psammomys obesus of the Jerusalem colony: a model for nutritionally induced, non-insulin-dependent diabetes. J Basic Clin Physiol Pharmacol. Apr.-Jun. 1993;4(1-2):83-99. Review.

Souci et al. XP-002354065; Food Composition and Nutrition Tables. Scientific Publishers Stuttgart 2000.

Blair SN, Capuzzi DM, Gottlieb SO, Nguyen T, Morgan JM, Cater NB. Incremental reduction of serum total cholesterol and low-density lipoprotein cholesterol with the addition of plant stanol ester-containing spread to statin therapy. Am J Cardiol. Jul. 1, 2000;86(1):46-52.

Tada N. Physiological actions of diacylglycerol outcome. Curr Opin Clin Nutr Metab Care. Mar. 2004;7(2):145-9. Review.

Taguchi H, Nagao T, Watanabe H, Onizawa K, Matsuo N, Tokimitsu I, Itakura H. Energy value and digestibility of dietary oil containing mainlyl,3-diacylglycerol are similar to those of triacylglycerol. Lipids. Apr. 2001;36(4):379-82.

Takase H. Metabolism of diacylglycerol in humans. Asia Pac J Clin Nutr.2007;16 Suppl 1:398-403. Review.

The Diabetes Prevention Program. Design and methods for a clinical trial in the prevention of type 2 diabetes. Diabetes Care. Apr. 1999; 22 (4):623-34.

Yarnell JW. The PRIME study: classical risk factors do not explain the severalfold differences in risk of coronary heart disease between France and Northern Ireland. Prospective Epidemiological Study of Myocardial Infarction.QJM. Oct. 1998;91 (10):667-76.

Tremblay AJ, Després JP, Piché ME, Nadeau A, Bergeron J, Alméras N, Tremblay A, Lemieux S. Associations between the fatty acid content of triglyceride,visceral adipose tissue accumulation, and components of the insulin resistance syndrome. Metabolism. Mar. 2004;53 (3):310-317.

U.K. prospective diabetes study 16. Overview of 6 years' therapy of type II diabetes: a progressive disease. U.K. Prospective Study Group. Diabetes. Nov. 1995;44(11):1249-58.

Lau VW, Journoud M, Jones PJ. Plant sterols are efficacious in lowering plasma LDL and non-HDL cholesterol in hypercholesterolemic type 2 diabetic and nondiabetic persons. Am Clin Nutr. Jun. 2005;81(6):1351-8.

Ling W.H., Jones P.J.H., Minireview Dietary Phytosterrols: A Review of Metabolism, Benefits and Side Effects. Life Sciences. 1995; 57 (3):195-206.

XP-0020354042; Nutritional Facts of Peanuts in the Diet Part 2. Nutrition and Food Science. 2003; 33(2): 56-64.

XP-002354047; Potential Health Benefits of Flax Seed. 1999.

Fu Z, Hou Y, Jiang T. XP-0020354049; Nutrient Health Food Function Reduce Blood Fat Delay Senile Preparation Process. Nutrition and Food Science. 2002.

XP 002359317; Prepared Foods: Supplementing with Enhanced Phyosterols; Apr. 2004.

Kuksis et al., "Preparation and Certain Physical Properties of Some Plant Steryl Esters" (1960) J. Org. Chem. 25(7):1209-1219.

Pihlajamaki et al., "Insulin resistance is associated with increased cholesterol synthesis and decreased cholesterol absorption in normoglycemic men" (2004) Journal of Lipid Research 45:507-512.

"Enzymotec Launches Healthy Oil Ingredient" (2003) Nutraceuticals International, p. 24.

Seki et al., "Effects of phytosterol ester-enriched vegetable oil on plasma lipoproteins in healthy men" (2003) Asia Pacific Journal of Clinical Nutrition 12(3): 282-291.

Flickinger, et al., "Nutritional Characteristics of DAG Oil" (2003) Lipids 38(2):129-132.

"Enzymotec launches healthy oil" Nutraingredients.com; Mar. 2, 2003.

"Functional oil shows triple action against heart disease" Nutraingredients.com; Feb. 11, 2004.

* cited by examiner

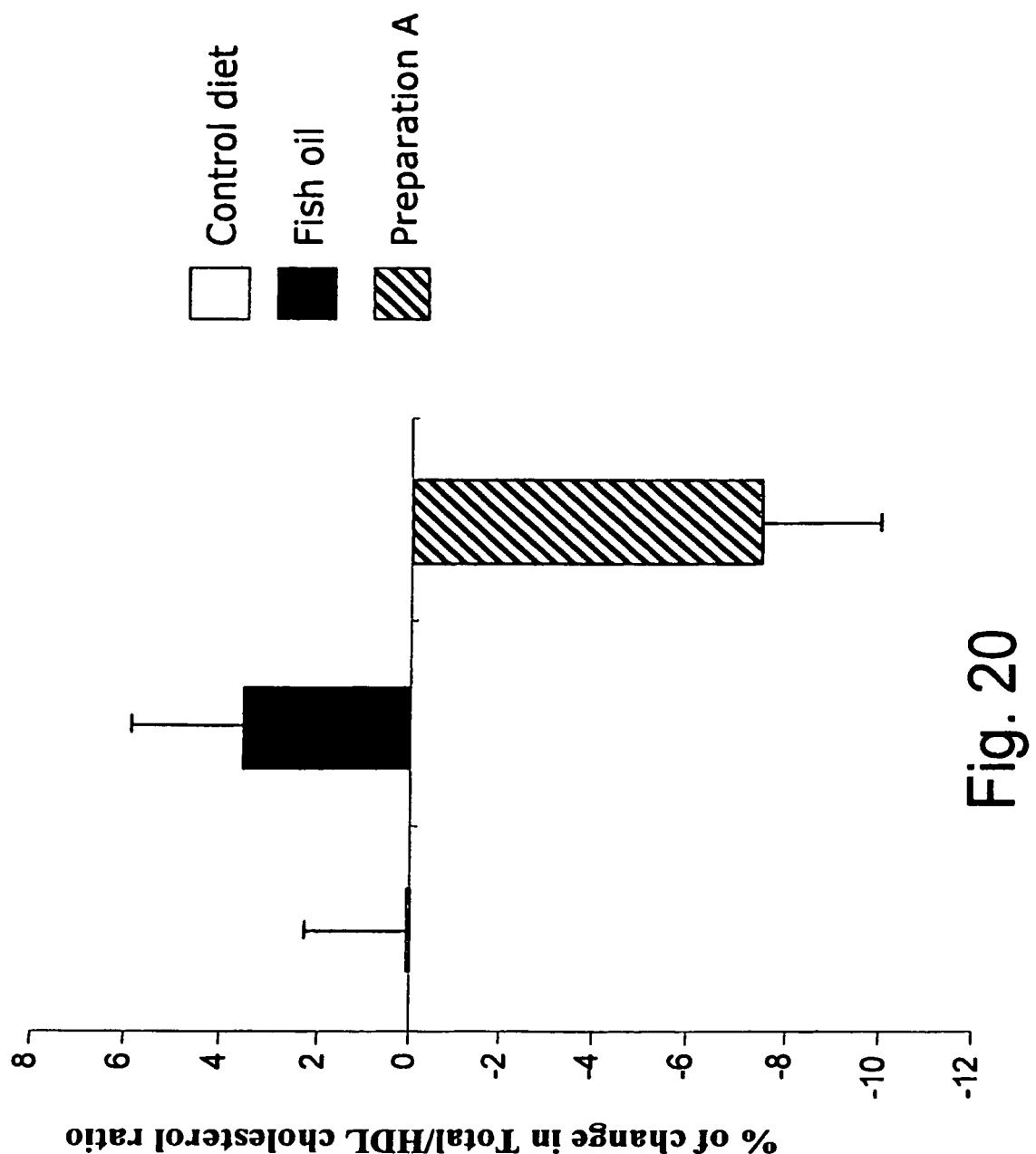

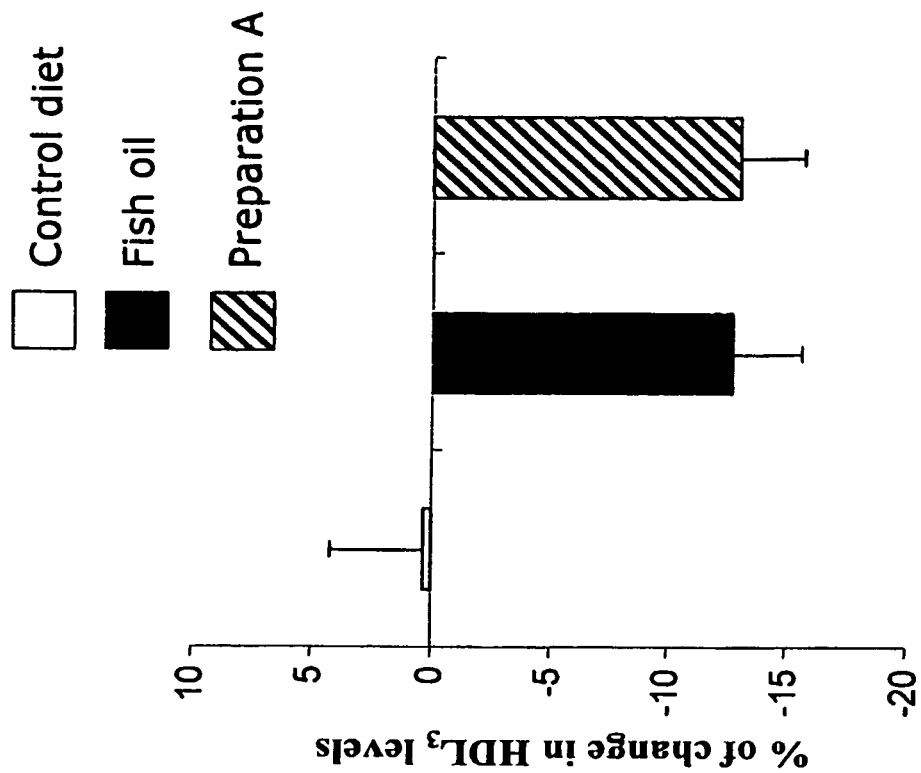
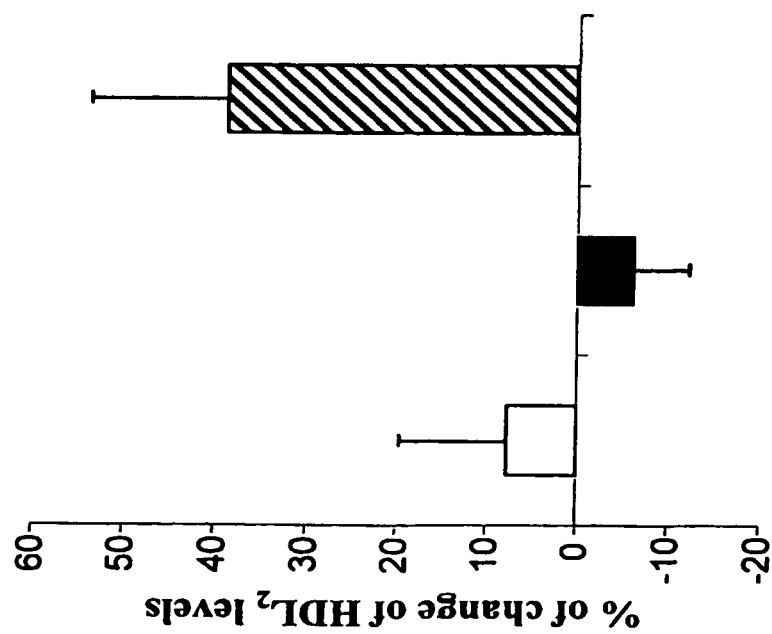
Fig. 21A
Fig. 21B

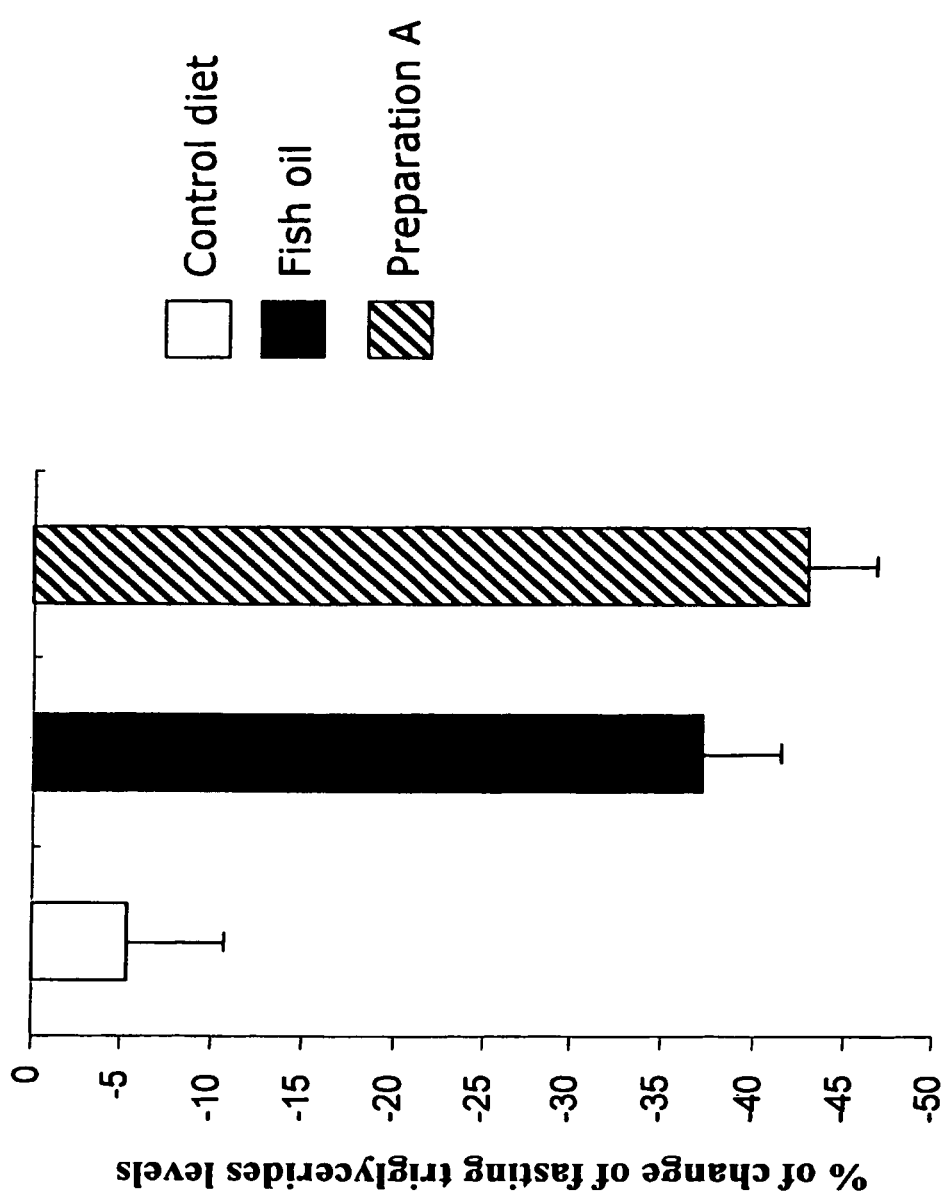

OILS ENRICHED WITH DIACYLGLYCEROLS AND PHYTOSTEROL ESTERS AND UNIT DOSAGE FORMS THEREOF FOR USE IN THERAPY

CROSS REFERENCE TO RELATED APPLICATION

This application is a continuation of U.S. Ser. No. 11/396,257, filed Mar. 31, 2006 now abandoned, which is a continuation-in-part of U.S. Ser. No. 11/199,584, filed Aug. 8, 2005, which is a continuation-in-part of PCT International Application No. PCT/IL2004/000131, filed Feb. 10, 2004, which claims priority of Israeli Patent Application Nos. 167818, filed Apr. 1, 2005; 155136, filed Mar. 27, 2003; and 154381, filed Feb. 10, 2003; the contents of each of which is hereby incorporated by reference in its entirety into this application.

FIELD OF THE INVENTION

The present invention relates to various lipid mixtures, more particularly special mixtures of fatty acids esters, which may be phytosterol esters and/or glyceride esters, as well as compositions, dietary nutrients, food supplements and nutraceuticals comprising thereof, intended for the treatment and prevention of diseases and conditions associated with lipid metabolism.

BACKGROUND OF THE INVENTION

All publications mentioned throughout this application are fully incorporated herein by reference, including all references cited therein.

Coronary Artery Disease (like atherosclerosis) is the major cause of morbidity and mortality in the Western world and its pathogenesis involves complicated interactions between cells of the arterial wall, blood cells, and plasma lipoproteins [Ross R. (1993) *Nature* 362: 801-809; Glass C. K. and Witztum J. L. (2001) *Cell* 104:503-516]. Today, it is common knowledge that lowering cholesterol levels reduces the risk of heart attacks, strokes and other forms of atherosclerotic vascular disease. In addition, many recent studies have shown that oxidative stress is a mechanism with a central role in the pathogenesis of atherosclerosis, cancer, and other chronic diseases, e.g. diabetes. In this scenario, a key role is played by macrophages in the sub-endothelial space, which are activated by oxidized low-density lipoproteins (ox-LDL). Recently, endothelial dysfunction due to oxidative stress was identified as a priming factor in the course of the development of atherosclerotic plaques.

LDL-cholesterol (LDL-C) levels are currently recommended as the primary target for lipid lowering therapy for prevention of CVD. The role of LDL-C in the development of atherosclerosis, the relation between blood LDL-C levels and risk of CVD, and the beneficial effects of LDL-C lowering therapy are well established. Similarly, it is well known that low levels of HDL cholesterol (HDL-C) are associated with an increased risk for CVD independent of LDL-C levels, and that raising HDL-C has been shown to significantly lower CVD risk. Total cholesterol/HDL-C ratio is most predictive of CHD as was demonstrated in several retrospective clinical trials. However, other factors may significantly affect the risk for CHD, and there is a growing body of evidence strongly suggesting a role of plasma triglycerides concentrations as an independent risk factor of CHD [Assmann G., et al. (1996) *Am. J. Cardiol.* 77(14):1179-1184]. Omega-3 fatty acids influence CVD risk in a multifactorial manner. Numerous findings, including evidence from randomized controlled trials, demonstrated the beneficial effects of Omega-3 long-chain polyunsaturated fatty acids (LC-PUFA) on CVD risk in patients with preexisting CVD as well as in healthy individuals. Large-scale epidemiological studies suggest that individuals at risk for CHD benefit from the consumption of plant- and marine derived Omega-3 fatty acids. Evidence from prospective secondary prevention studies and randomized controlled trials indicate that Omega-3 fatty acids supplements can reduce cardiac events (e.g., death, non-fatal myocardial infarct, non-fatal stroke) and decrease progression of atherosclerosis in coronary patients [Kris-Etherton P M., et al. (2002) *Circulation* 106(21):2747-2757] Omega-3 fatty acids reduce very-low density lipoprotein (VLDL) secretion, lower triglycerides transport and enhance VLDL clearance, and reduce circulating triglycerides. Omega-3 fatty acids have markedly anti-inflammatory, anti-thrombotic and immuno-modulatory properties that may be beneficial in CVD.

EPA and DHA may alter HDL cholesterol subclasses. Increases in the $HDL_2$ subfraction have been reported with supplementation of 4 g DHA/d in hyperlipidemic men and type 2 diabetic patients [Mori, T. A. et al. (2000) *Am. J. Clin. Nutr.* 2000; 71: 1085-94]. The effect of EPA on $HDL_2$ subclasses is less clear; a lowering effect on $HDL_3$ concentrations, with no effect on $HDL_2$ have been observed. When supplemented simultaneously, 1.48 mg DHA and 1.88 mg EPA/d were shown to increase $HDL_2$ concentrations in subjects with familial combined hyperlipidemia, a disorder characterised by low $HDL_2$ concentrations [Calabresi, L. et al. (2004) *Metabolism* 53:153-8]. HDL cholesterol concentrations are usually not significantly affected by plant sterols, but a slight increase has been reported in a few studies [Gylling, H. and Miettinen, T. A. (1999) *Metabolism* 48: 575-80].

Subjects identified as having low density lipoprotein (LDL) cholesterol concentrations above 130 mg/dl are routinely counselled to modify their diet with respect to saturated fat and cholesterol intake. At present the dietary guidelines are relatively broad; total fat 20-25% of energy (<10% of energy saturated fatty acids [SFA], 5-15% of energy monounsaturated fatty acids [MUFA], up to 10% of energy polyunsaturated fatty acids [PUFA], <300 mg cholesterol per day). In addition to the aforementioned dietary recommendations, the use of plant sterols and stanols to optimize blood lipid levels has gained increased importance through the year 2001, with the new recommendation released from the National Cholesterol Education Program advising the public to consume 2 g per day of plant sterols or stanols in addition to the Therapeutic Lifestyle Change Diet to lower elevated LDL cholesterol levels. Plant sterols and stanols are now widely available in many countries across the world as functional foods possessing government-approved health claims.

Paraoxonase (PON1) is an esterase, transported in the plasma as a component of HDL, associated to ApoAI and ApoJ. It has been shown in vitro that purified PON1 and HDL-associated PON1 inhibit the oxidative modification of LDL. Thus, the presence of PON1 in HDL may account for a proportion of the anti-oxidant properties of these lipoproteins [Tsuzura, S., et al. (2004) *Metabolism.* 53:297-302]. Interestingly, several investigators have shown that serum paraoxonase activity is lower in diabetic patients and is lower yet in those with diabetic complications, independent of PON1 gene polymorphisms. These observations are consistent with in vivo increased oxidative stress levels in diabetic patients.

The LDL oxidation hypothesis of atherosclerosis raised an extensive investigation into the role of anti-oxidants against LDL oxidation as a possible preventive treatment of atherosclerosis. Although increased resistance of LDL to oxidation was observed after treatment with various synthetic pharmaceutical agents, an effort has been made to identify natural food products, which offer anti-oxidant defense against LDL oxidation.

Olive oil has been shown to inhibit LDL oxidation and this effect could be related to its high oleic acid content, as well as to some phenolics (hydroxytoluene, oleoropein) and phytosterols such as sitosterol [Aviram M. and Kasem E. (1993) Ann. Nutr. Metabol. 37:75-84; Visioli F. et al. (1995) Atherosclerosis 117:25-32].

In addition to LDL oxidation, a known risk factor for coronary heart disease (CHD)—the result of atherosclerosis in the coronary arteries—includes high serum LDL cholesterol concentration. There is a positive linear relationship between serum total cholesterol and LDL cholesterol concentrations, and risk of, or mortality from CHD [Jousilahtu et al. (1998) Circulation 97:1084-1094]. High concentrations of serum triacylglycerols may also contribute to CHD [Austin, M. A. (1989) Am. J. Epidemiol. 129:249-259], but the evidence is less clear. Diacylglycerols (DAG) have been shown to lower the postprandial elevation of serum triacylglycerols levels compared with triacylglycerols in healthy humans [Taguchi, H et al. (2000) J. Am. Coll. Nutr. 19:789-796].

Phytosterols and CHD

The term "phytosterols" covers plant sterols and plant stanols, including beta-sitosterol, campesterol and stigmasterol. Plant sterols are naturally occurring substances present in the diet as minor components of vegetable oils. Plant sterols have a role in plants similar to that of cholesterol in mammals, e.g. forming cell membrane structures. In human nutrition, both plant sterols and plant stanols are effective in lowering total plasma cholesterol levels and LDL-cholesterol.

The consumption of plant sterols and plant stanols lowers blood cholesterol levels by inhibiting the absorption of dietary and endogenously-produced cholesterol from the small intestine. The plant sterols/stanols are very poorly absorbable compounds. This inhibition is related to the similarity in physico-chemical properties of plant sterols and stanols to cholesterol.

In addition, both plant sterols and plant stanols have been subjected to rigorous toxicological evaluation. Studies on the absorption, distribution, metabolism and excretion have shown that plant sterols are poorly absorbed from the intestine (1-10%).

The specific plant sterols that are currently incorporated into foods for their hypocholesterolemic effects are extracts of soybean or tall (pine tree) oils. In most cases these plant sterols are esterified to unsaturated fatty acids (creating sterol esters) to increase miscibility within the foods they are normally matrixed into. Some plant sterols currently in use are hydrogenated prior to esterification, resulting in saturated stanol derivatives, or plant stanols, such as beta-sitostanol and campestanol. Additional sources of plant sterols that are now becoming available are derived directly from corn fiber and not further modified, microcrystallinized in a way that obviates the need for esterification, or esterified to specific fatty acids that may have independent biological activity such as omega-3 fatty acids.

In the early 1950's plant derived sterols were first observed to decrease serum cholesterol levels and were marketed by Eli Lilly as Cytellin™.

Plant sterols consumption at 2-3 g/day has been demonstrated to lower circulating LDL cholesterol levels by 10-15% in humans with hyperlipidemia, offering a useful dietary strategy to risk management for heart disease. The mechanism of action of plant sterols in lowering LDL levels remains to be fully explained, however, it has been demonstrated that plant sterols act by excluding dietary and biliary cholesterol from micelles in the intestine during the process of absorption. Plant sterols, due to their chemical structure, prevent cholesterol from entering the outer micellar zone, thereby restricting the passage of cholesterol from the intestinal lumen across into the mucosal cell of the intestinal wall. Recently, it has been demonstrated that certain types of compounds, such as ascorbic acid, attached to the hydroxyl group of plant sterols such as sitosterol and campesterol as esters, increase the efficacy of cholesterol lowering in animal experiments, likely through more aggressive exclusion of cholesterol from the micelle.

In the United States, a panel of independent experts has concluded that vegetable oil sterol esters, meeting appropriate food-grade specifications and produced by current good manufacturing practice (21 C.F.R. §182.1(b)), are safe for use as an ingredient in vegetable oil spreads, in amounts which do not exceed 20% of plant sterol esters. It was the Panel's opinion, together with qualified experts in the field, that vegetable oil sterol esters are safe for use, i.e. vegetable oil sterol esters were granted the GRAS status (Generally Recognized As Safe). Based on the GRAS recognition, the US Food and Drug Administration (FDA) has cleared to use a spread containing up to 20% of plant sterol esters and another one containing plant stanol ester. Similar approvals were given in different European countries as well as in Asia and Australia.

A recent review teaches that in recent years, with the growing interest in functional foods, the use of phytosterols for reducing serum cholesterol levels has gained considerable momentum [Stark, A. H. et al. (2002) Nutrition Reviews 60(6):170-176]. This should be attributed, inter alia, to the esterification of phytostanol with fatty acids (stanyl esters), providing commercial scale production of phytosterol-containing foods, such as margarines. Like stanyl esters, phytosteryl esters (steryl esters) have been shown in clinical studies to consistently lower serum LDL-cholesterol (LDL-C) levels (reducing by up to about 10% or more), with no change seen in HDL-cholesterol (HDL-C) values. The review suggests that properly formulated free phytosterols and stanols may be as effective as stanyl and steryl esters in lowering LDL-C levels in humans.

WO 01/32035 teaches olive oil-based products, based on especially higher grades of olive oils (such as virgin olive oils), comprising plant stanol esters and/or plant sterol esters.

U.S. Pat. No. 5,843,499 discloses oil extractable from corn fiber that contains ferulate esters (phytosterol esters which are esterified to ferulic acid), in particular sitostanyl ester, which has been shown to have cholesterol-lowering activity. It is mentioned that corn fiber oil (containing about 73% fat (triacylglycerol), 8% sterol (fatty acyl) esters, 4% free sterols, 6% diacylglycerols and 6% ferulate (sterol esters)) is used as an additive to supplementary food for reducing cholesterol level.

U.S. Pat. No. 6,326,050 discloses a composition consisting of oil or fat, a diacylglycerol, a free phytosterol and tocopherol, dissolved or dispersed in the oil or fat. This composition plays a role in lowering blood cholesterol of hypercholesterolemic individuals.

However, none of the above mentioned publications describes reduction of both cholesterol and triglycerides serum levels.

Olive oil, in contrast to other mentioned vegetable oils (such as corn fiber oil, table cooking oil, soybean oil, rapeseed oil, rice bran oil, and palm oil) is composed, inter alia, of 55 to 85% monounsaturated fatty acids (MUFA), in particular oleic acid, which contribute to the high nutritional value of this oil. There are some distinct advantages of using olive oil over other vegetable oils. Diets rich in olive oil have been shown to be more effective in lowering total cholesterol and LDL-cholesterol than conventional dietary treatments not containing high levels of MUFA [Brown M. S and Goldstein J. L. (1983) *Ann. Rev. Biochem.* 52:223-261].

Furthermore, olive oil is an integral ingredient of the Mediterranean diet and accumulating data suggests that it may have health benefits that include reduction of risk factors of coronary artery disease, prevention of several types of cancer, and modification of immune and inflammatory response [Brown and Goldstein (1983) id ibid.].

WO01/15552 describes a nutritional supplement comprising purified esters of omega-3 fatty acids with phytosterols, for lowering triglyceride and cholesterol blood levels. This publication does not describe mixtures of such esters with a fat base, such as fish oil. Moreover, this publication does not describe any effect of the disclosed esters on blood lipids sub-fractions.

U.S. Pat. No. 6,589,588 discloses a sterol or stanol composition, wherein the fatty acid moiety comprises a blend of less that 7% of saturated fatty acids and more than 50% of polyunsaturated fatty acids, for lowering absorption of cholesterol for the digestive tract. Also this publication does not describe mixtures of the esters with fish oil, or any other fat, oil or lipid, and does not present any results as to the cholesterol reducing activity of the esters, neither any other activity, such as lowering triglycerides, controlling HDL subfractions, or the like.

Co-owned WO03/064444 describes a composition of matter comprising diacylglycerol(s), mainly 1,3-diacylglycerols (DAG) and phytosterol and/or phytostanol ester(s) (PSE), dispersed in oil and/or fat.

In the parent application, U.S. Ser. No. 11/199,584, the inventors report that said combination of diacylglycerol(s), mainly 1,3-DAGs, and PSEs, preferably dissolved or dispersed in oil and/or fat, has a synergistic effect and decreases both LDL-cholesterol and triglycerides levels in the blood. This combination further exhibited increased serum and macrophage anti-oxidative properties, and in particular LDL anti-oxidative properties, resulting in reduction of the risk for CHD and arteriovascular diseases.

In the parent application, an effect in reducing both cholesterol and triglycerides serum levels, together with increased anti-oxidative properties, was observed even when a combination containing only 11 wt % DAG and 20 wt % phytosterol esters (in oil) was employed.

It is an object of the present invention to provide mixtures of omega-3 fatty acids, preferably DHA and EPA, esterified to other lipids with improved activity in, e.g. reducing levels of as apolipoprotein B, decreasing levels of HDL subfraction $HDL_3$, whilst elevating the level of $HDL_2$.

These and other objects of the invention will become apparent as the description proceeds.

SUMMARY OF THE INVENTION

In a first aspect the present invention provides an edible mixture of esters of long chain polyunsaturated fatty acids (LC-PUFA), wherein said mixture comprises esters of LC-PUFA with phytosterols and/or phytostanols and esters of LC-PUFA with glycerol, optionally also comprising free phytosterols and/or phytostanols, wherein the weight ratio of said LC-PUFA glycerol esters to their esters with phytosterol or phytostanol is from about 19:1 to about 1.5:1. In one preferred embodiment, said esters of LC-PUFA with glycerol are mono-, di- and/or triglycerides.

In a second aspect the present invention provides an edible composition of matter comprising a mixture of esters of LC-PUFA with glycerol, enriched with a mixture of esters of LC-PUFA with phytosterols and/or phytostanols, wherein said mixture of esters LC-PUFA with glycerol is derived from: an animal source, particularly fish oil, a plant, algae or microorganisms; and wherein the weight ratio of said LC-PUFA glycerol esters to their esters with phytosterol or phytostanol is from about 1.5:1 to about 1:9.

The mixture described herein, or the edible composition of matter comprising thereof, is intended for various uses, including:

(a) reducing the risk of developing metabolic disorder and/or insulin resistance syndrome;
(b) reducing circulating atherogenic small-dense LDL particles, while maintaining a high proportion of HDL/LDL ratio;
(c) shifting the HDL profile in the direction of larger and less dense particles, particularly reducing the $HDL_3$ sub-fraction while increasing the level of $HDL_2$ sub-fraction;
(d) reducing and/or preventing the progression of the metabolic disorder and/or insulin resistance syndrome and/or atherosclerotic deleterious processes;
(e) attenuating or counteracting any adverse effects of use of omega-3 fatty acids in the form of oils, wherein said adverse effect may be elevating LDL cholesterol or increasing the total/HDL cholesterol ration, related to a decrease in HDL cholesterol levels.

In a further aspect the present invention provides an orally administrable pharmaceutical or nutraceutical unit dosage form comprising an edible mixture of esters LC-PUFA with glycerol, enriched with a mixture of esters of LC-PUFA with phytosterols and/or phytostanols, wherein said unit dosage form contains about 1.4-1.6 g of said phytosterol/phytostanol LC-PUFA esters, said dosage form being capable of providing at least 50% of the recommended daily intake (RDI) of phytosterols and the recommended daily intake of LC-PUFA. Preferably, said RDI of phytosterols is from about 0.4 g to about 0.8 g and said RDI of LC-PUFA, specifically, DHA and EPA, is from about 0.3 g to about 0.65 g.

In one preferred embodiment said pharmaceutical dosage form is in the form of a capsule, preferably a soft gel capsule.

Similarly, said pharmaceutical dosage form is intended for the same uses as described above for the mixture of the invention, i.e., in reducing the risk of developing metabolic disorder and/or insulin resistance syndrome; in reducing circulating atherogenic small-dense LDL particles, while maintaining a high proportion of HDL/LDL ratio; in shifting HDL profile in the direction of larger and less dense particles, particularly reducing the $HDL_3$ subfraction while increasing the level of $HDL_2$ subfraction; in reducing and/or preventing the progression of the metabolic disorder and/or insulin resistance syndrome and/or atherosclerotic deleterious processes; in attenuating or counteracting any adverse effects of use of omega-3 fatty acids in the form of oils, wherein said adverse effect may be elevating LDL cholesterol or increasing the total/HDL cholesterol ration, related to a decrease in HDL cholesterol levels.

In a further most preferred embodiment, the pharmaceutical dosage form described herein above is for twice daily administration.

In a yet further aspect, the present invention provides a method of treatment of metabolic syndrome and related conditions, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

In an even further aspect, the present invention provides a method of reducing circulating atherogenic small-dense LDL particles, while maintaining a high proportion of HDL/LDL ratio, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

In a final aspect the present invention provides a method of shifting the HDL profile in the direction of larger and less dense particles, particularly reducing the $HDL_3$ subfraction while increasing the level of $HDL_2$ subfraction, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

Common to all methods described above, said effective dose is preferably comprised in a soft gelatine capsule, while said method comprises administering said capsule to said patient twice daily.

In addition, it is to be understood that the weight ratio of said LC-PUFA glycerol esters to their esters with phytosterol or phytostanol comprised in the mixture used in the methods described above may also be in the range between 9:1 to 1:9, or from 9:1 to 1:3, or more preferably from 3:1 to 1.5:1.

The invention will be described in more detail on hand of the accompanying Figures.

BRIEF DESCRIPTION OF THE FIGURES

FIG. 1A: Macrophage peroxide levels determined by the cells mean fluorescence (emitted by DCF) intensity.

FIG. 1B: Macrophage peroxide levels determined by the percentage of fluorescent positive cells.

Abbreviations: PS-E, Plant sterols esters; DAG, diacylglycerol, cont., control; Ol. O., olive oil.

Figure 1A:
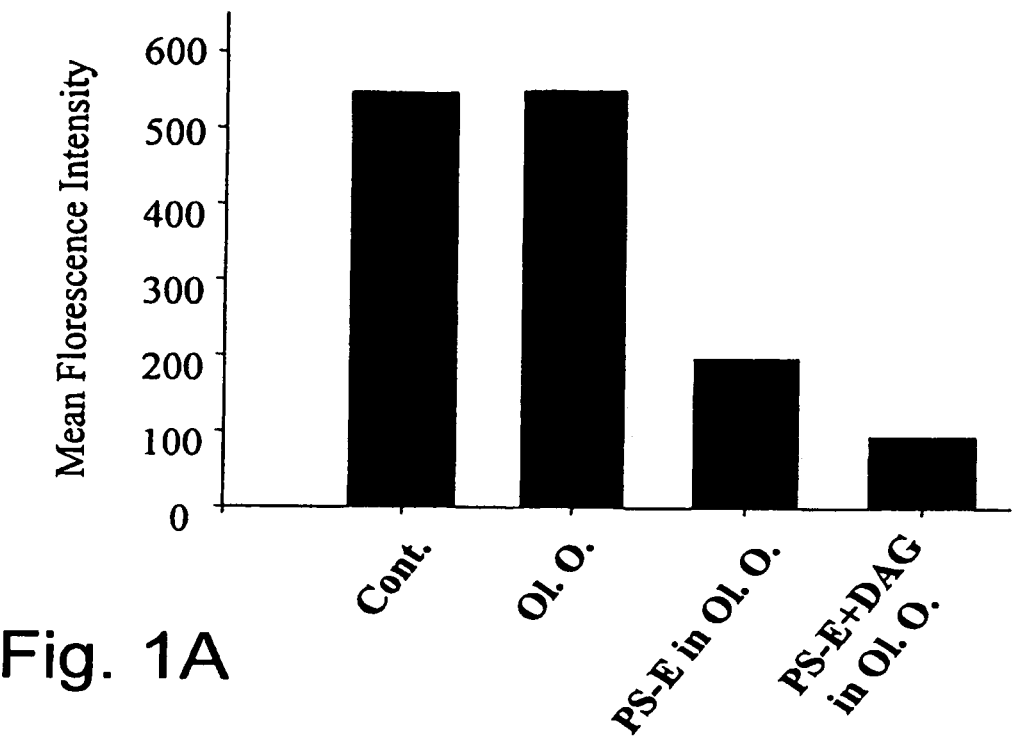
FIG. 1A-B: The effect of olive oil, olive oil+phytosterols, and PSE+DAG in olive oil on macrophage cellular peroxides content
Figure 1B:
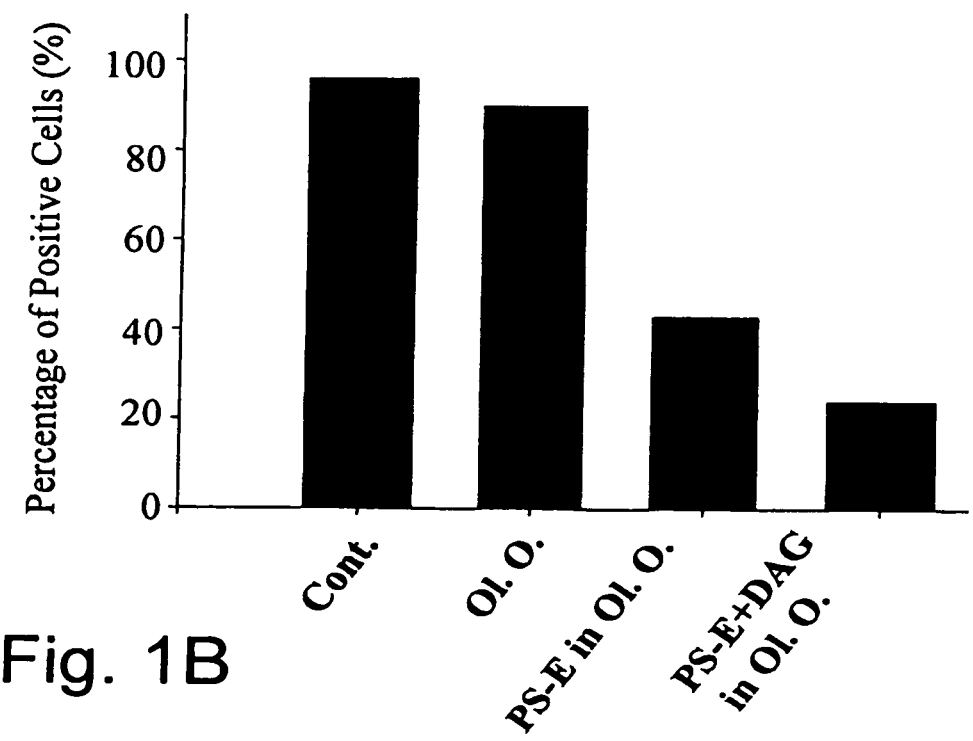
Figure 2:
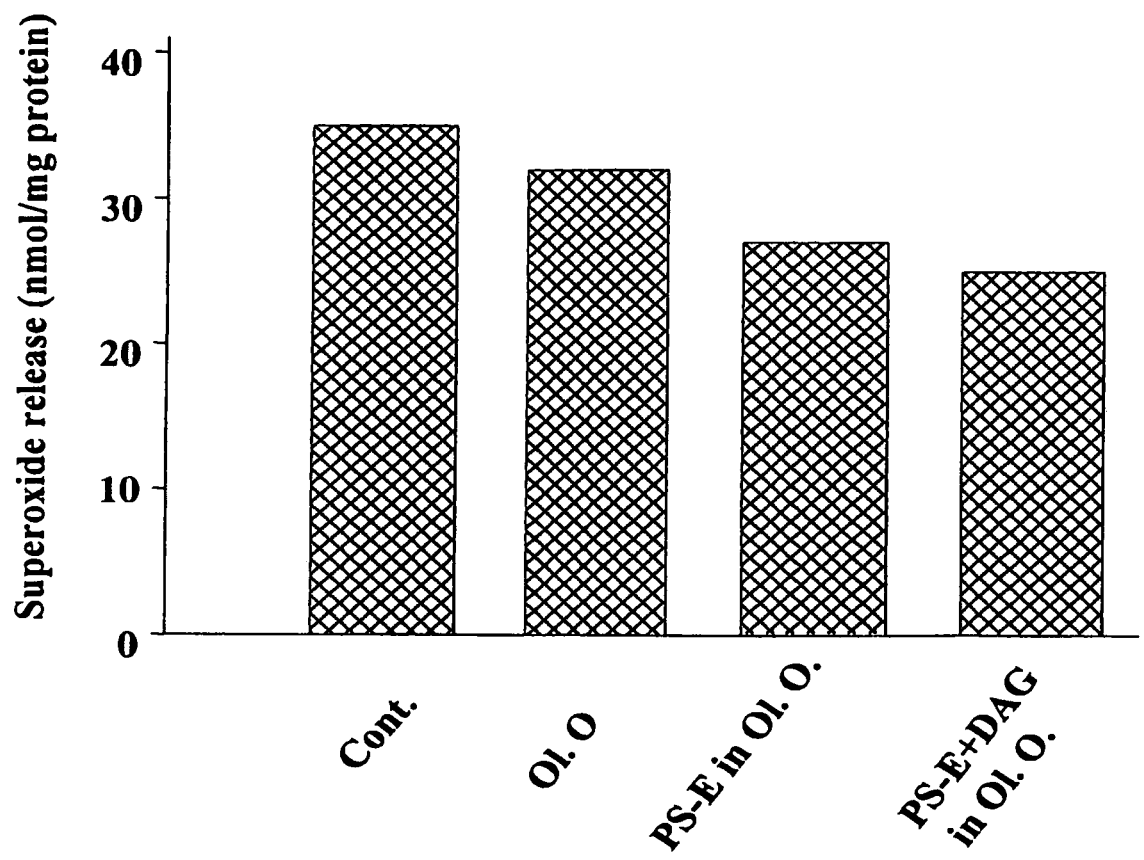

FIG. 2: The effect of olive oil, olive oil+phytosterols, and PSE+DAG in olive oil on macrophage superoxides anions release Macrophage superoxide ions release was determined by the superoxide dismutase-inhibitable reduction of cytochrome C.

Abbreviations: PS-E, Plant sterols esters; DAG, diacylglycerol, cont., control; Ol. O., olive oil.

Figure 3:
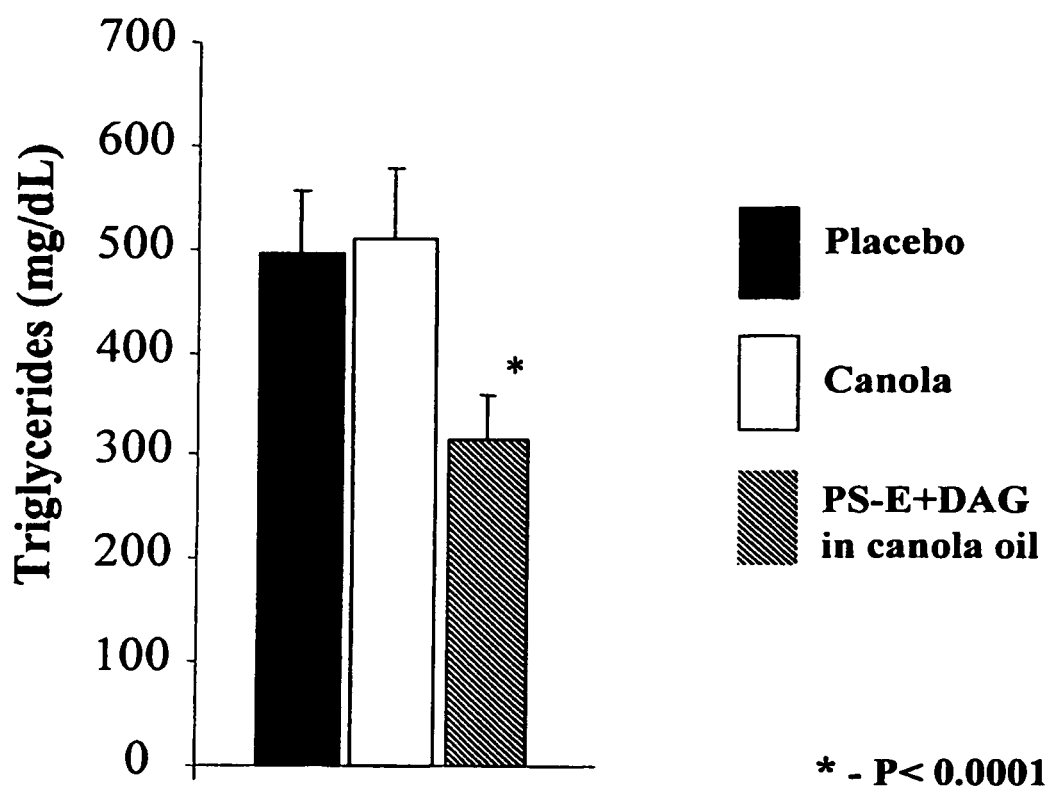

FIG. 3: Effect of PSE+DAG in canola oil consumption on serum triglycerides profile FIG. 4: Effect of PSE+DAG in canola oil consumption on serum total cholesterol profile FIG. 5: Effect of PSE+DAG in canola oil and PSE+DAG in fish oil consumption on serum oxidative stress FIG. 6: Effect of PSE+DAG in canola oil and PSE+DAG in fish oil consumption on serum PON1 activity Abbreviations: Ser. PON1 act., serum PON1 activity; Plac., placebo; Can., canola.

Figure 7:
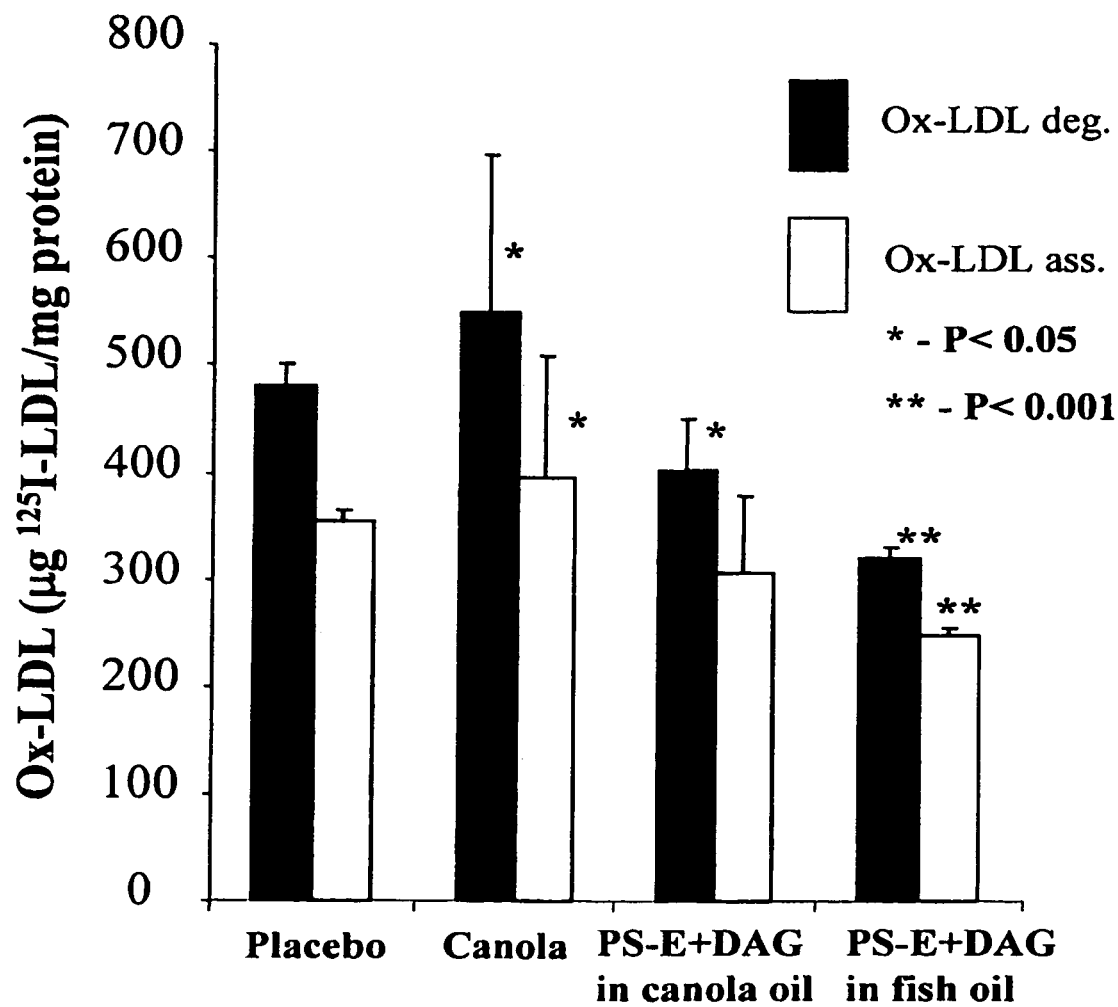

FIG. 7: Effect of PSE+DAG in canola oil and PSE+DAG in fish oil consumption on ox-LDL uptake by peritoneal macrophages Abbreviations: deg., degradation; ass., association.

Figure 8:
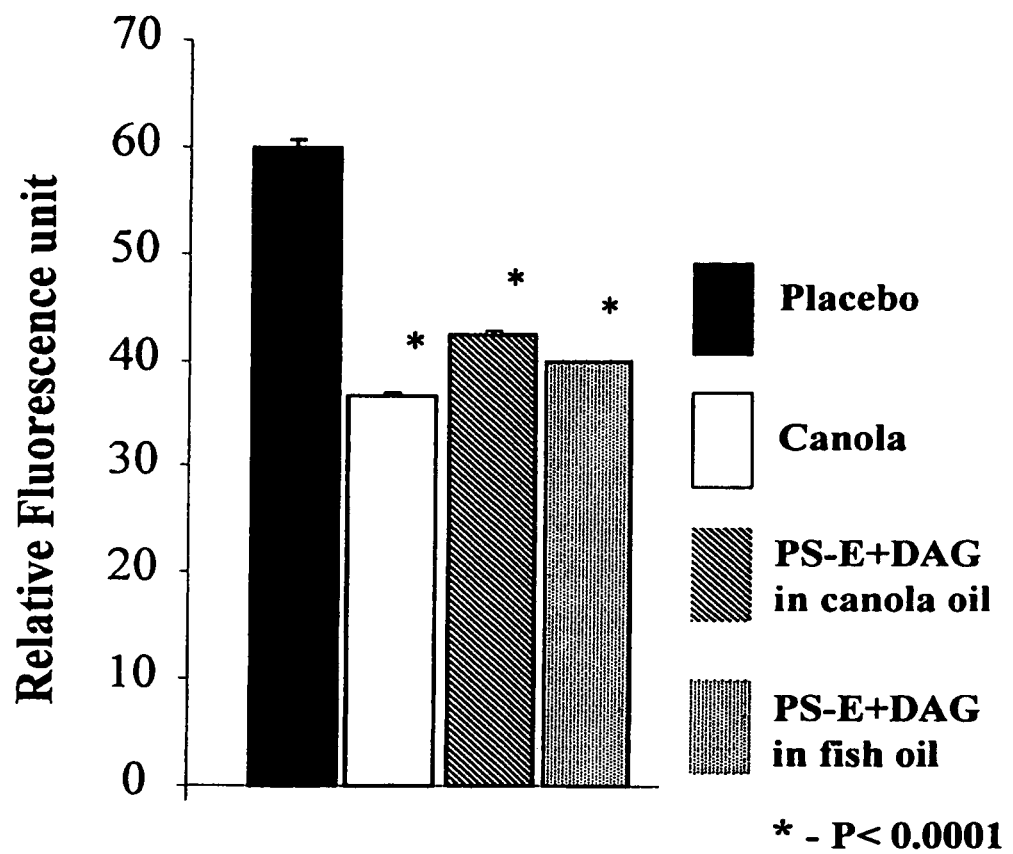
Figure 9:
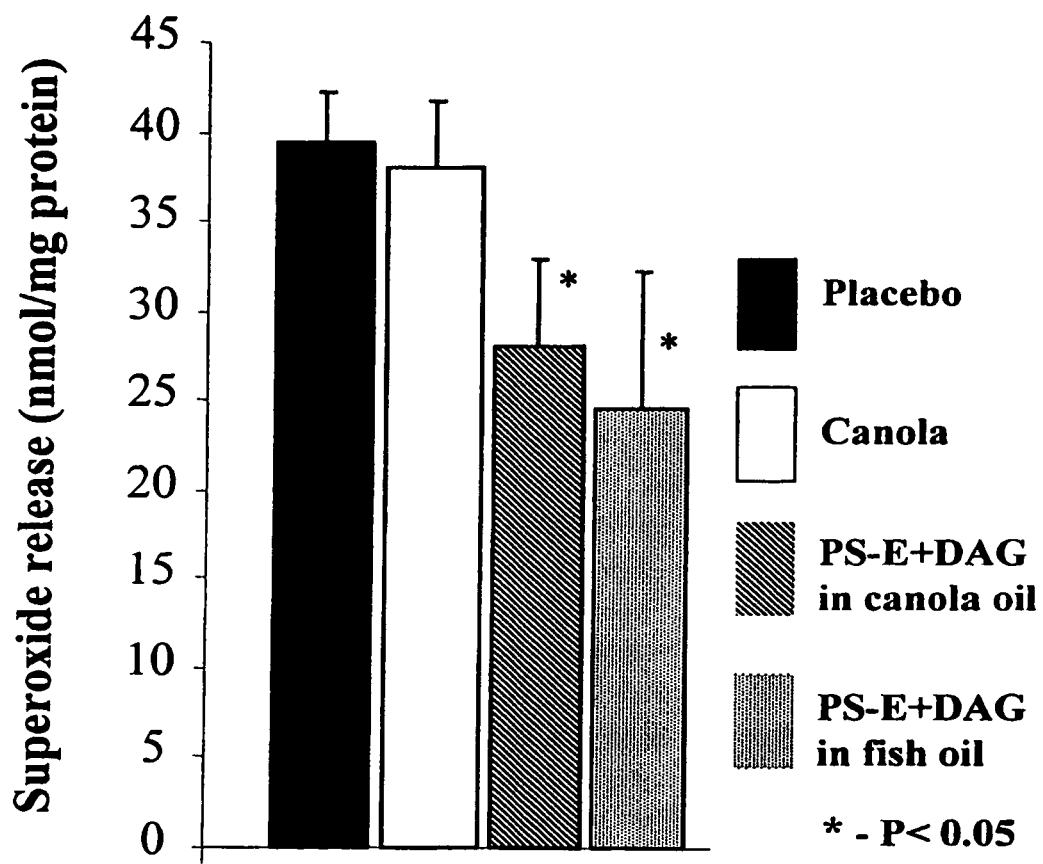

FIG. 8: Effect of PSE+DAG in canola oil and PSE+DAG in fish oil consumption on macrophage oxidative status FIG. 9: Effect of PSE+DAG in canola oil and PSE+DAG in fish oil consumption on PMA-induced superoxide anions release in macrophages FIG. 10: Change in total cholesterol concentrations Hypercholesterolemic overweight volunteers were fed for four weeks with control olive oil diet or PS-E+DAG in olive oil followed by four weeks of washout and counter supplementation. Total cholesterol levels were tested at the beginning (open squares) and at the termination (closed squares) of each phase as described in methods. Values represent mean±SEM of the total cholesterol concentrations in 21 patients. Statistical significance between baseline and endpoint values as found by Student's t-test is * $P<0.05$ or ** $P<0.001$.

Figure 11:
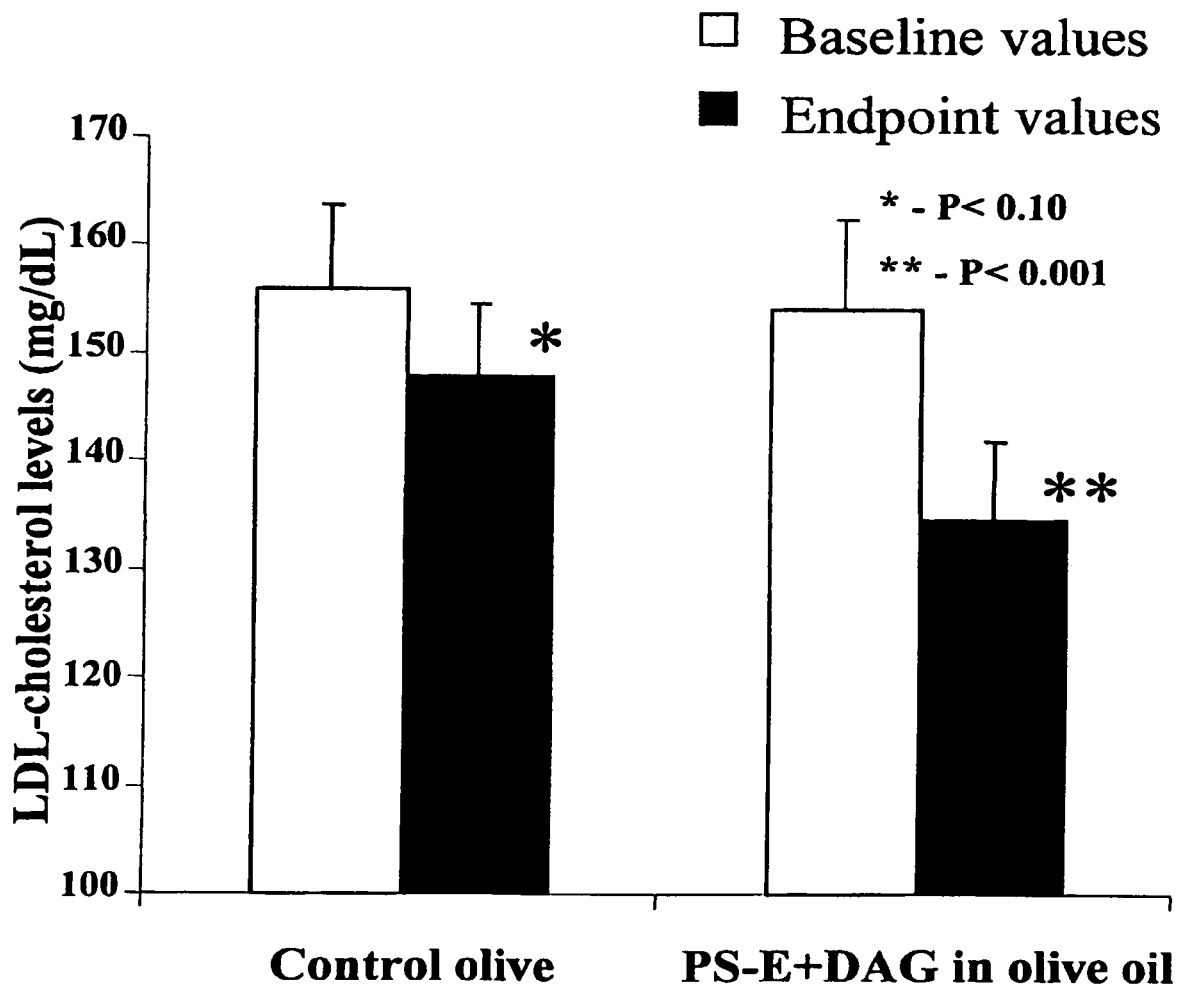

FIG. 11: Change in LDL cholesterol concentrations

Hypercholesterolemic overweight volunteers were fed for four weeks with control olive oil diet or PS-E+DAG in olive oil followed by four weeks of washout and counter supplementation. LDL cholesterol levels were tested at the beginning (open squares) and at the termination (closed squares) of each phase as described in methods. Values represent mean±SEM of the LDL cholesterol concentrations in 21 patients. Statistical significance between baseline and endpoint values as found by Student's t-test is * $P<0.10$ or ** $P<0.001$.

Figure 12:
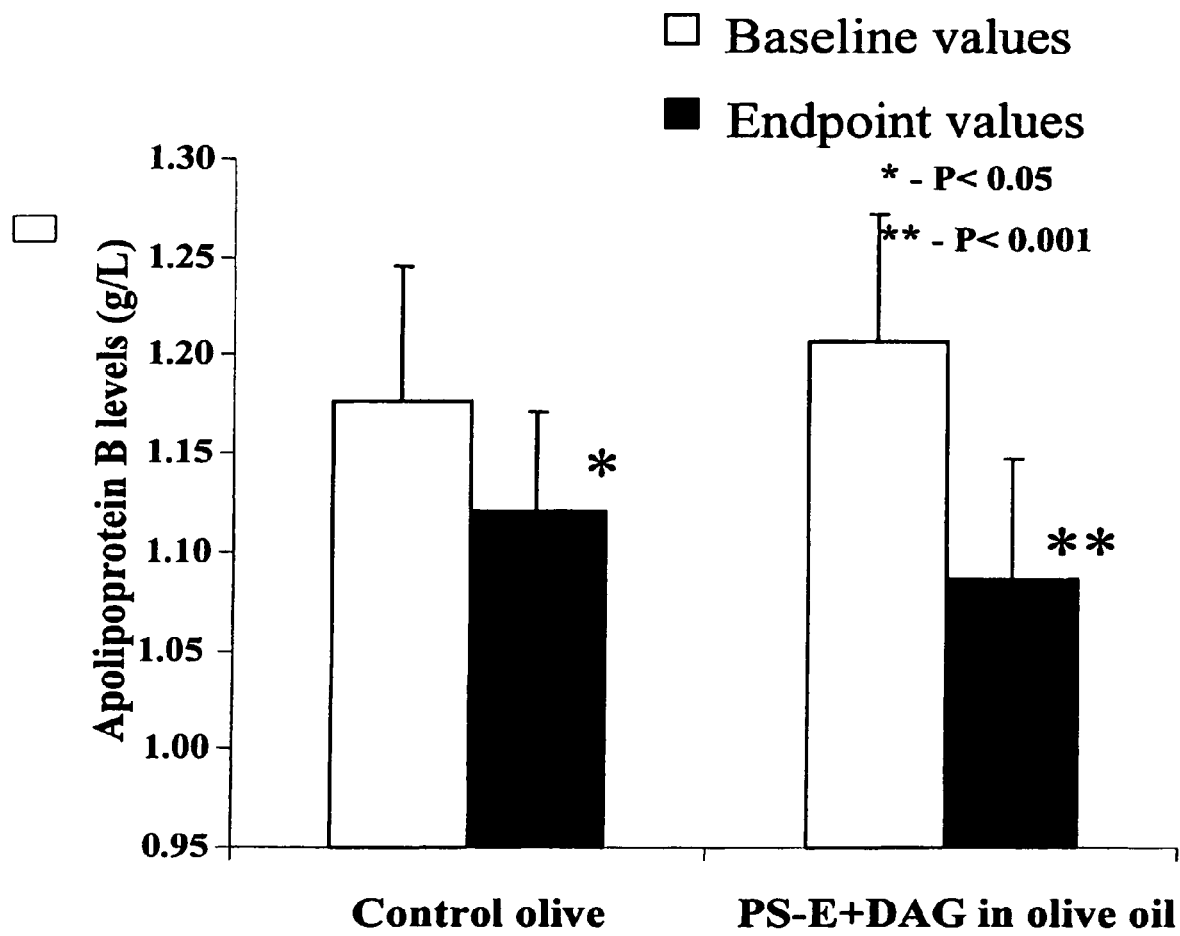

FIG. 12: Change in Apolipoprotein B concentrations

Hypercholesterolemic overweight volunteers were fed for four weeks with control olive oil diet or PS-E+DAG in olive oil followed by four weeks of washout and counter supplementation. ApoB levels were tested at the beginning (open squares) and at the termination (closed squares) of each phase as described in methods. Values represent mean±SEM of the apoB concentrations in 21 patients. Statistical significance between baseline and endpoint values as found by Student's t-test is * $P<0.05$ or ** $P<0.001$.

Figure 13:
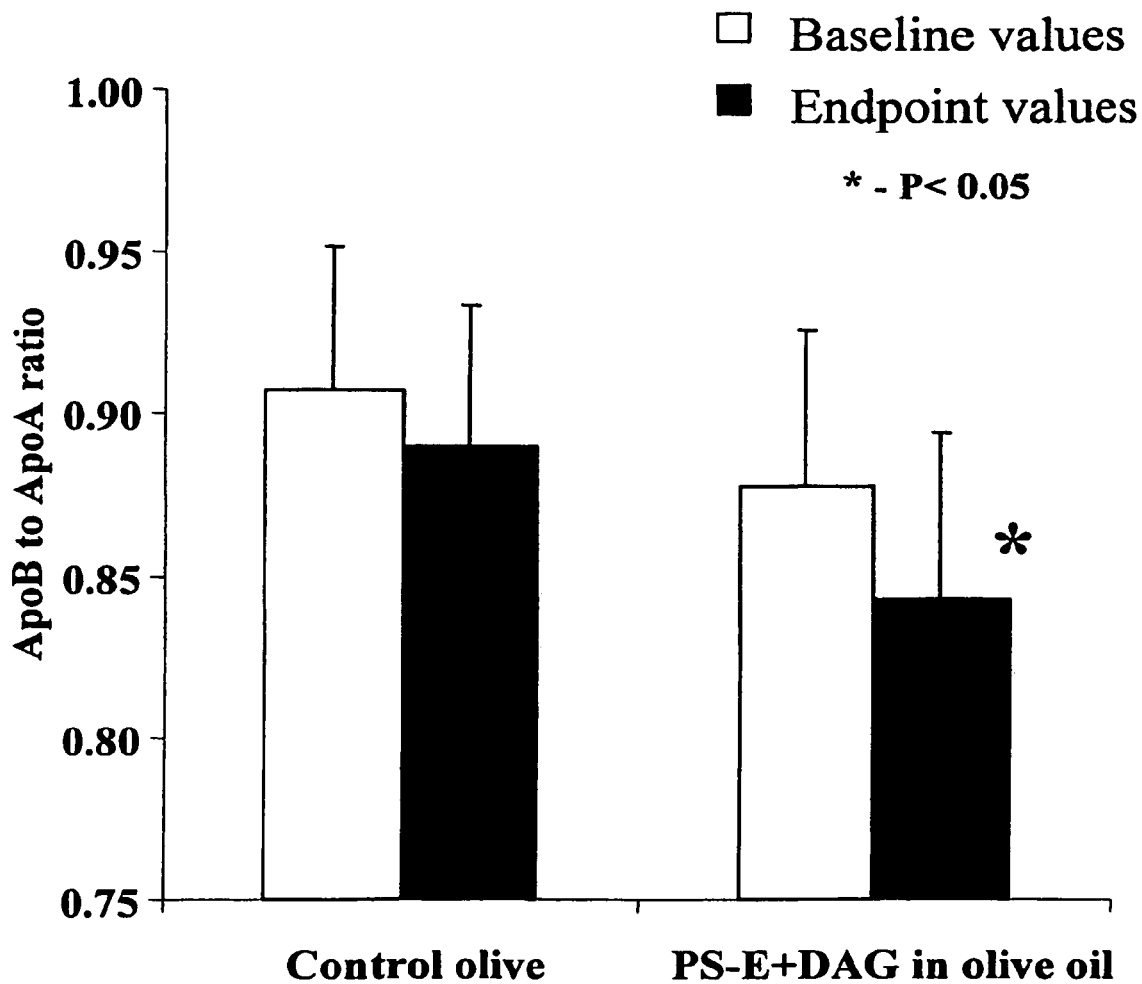

FIG. 13: Change in ApoB to ApoA ratio

Hypercholesterolemic overweight volunteers were fed for four weeks with control olive oil diet or PS-E+DAG in olive oil followed by four weeks of washout and counter supplementation. ApoB/ApoA ratios were tested at the beginning (open squares) and at the termination (closed squares) of each phase as described in methods. Values represent mean±SEM of the ApoB/ApoA ratios in 21 patients. Statistical significance between baseline and endpoint values as found by Student's t-test is * $P<0.05$.

Figure 14:
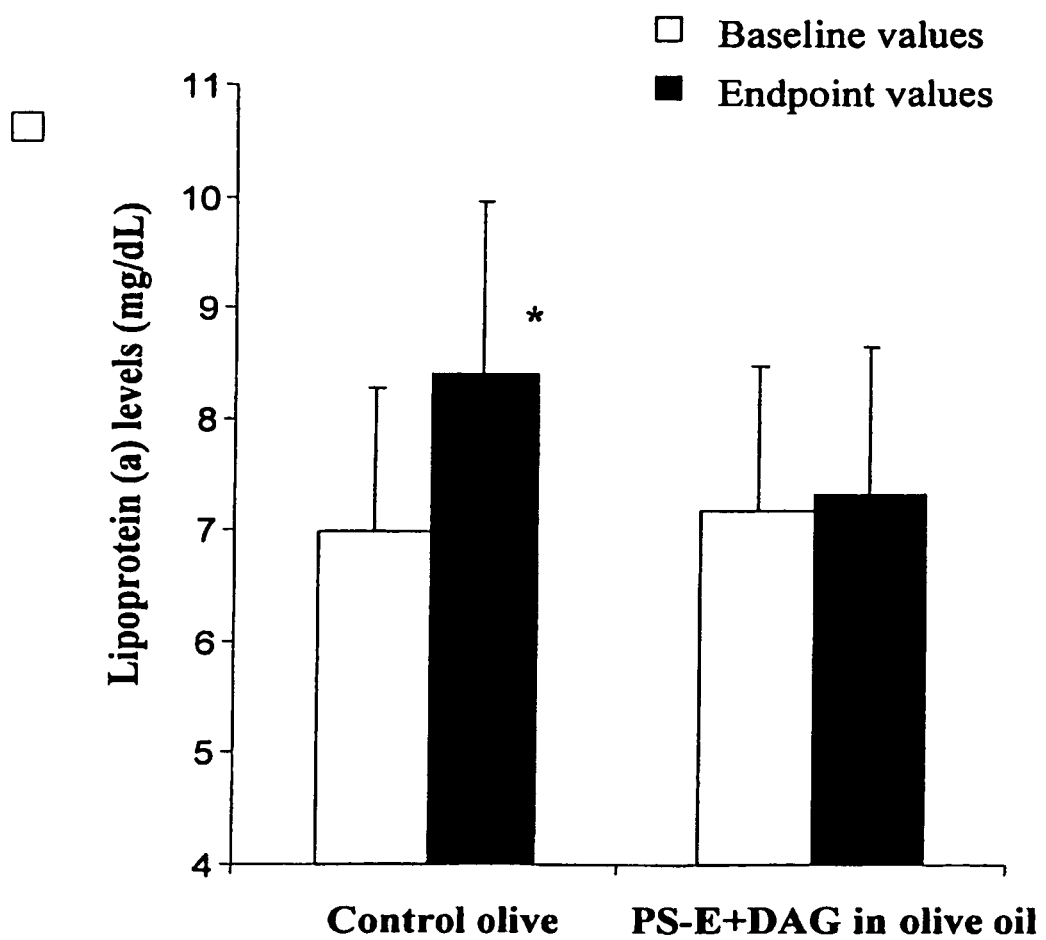

FIG. 14: Change in lipoprotein(a) concentrations

Hypercholesterolemic overweight volunteers were fed for four weeks with control olive oil diet or PS-E+DAG in olive oil followed by four weeks of washout and counter supplementation. Lp(a) levels were tested at the beginning (open squares) and at the termination (closed squares) of each phase as described in methods. Values represent mean±SEM of the Lp(a) concentrations in 21 patients. Statistical significance between baseline and endpoint values as found by Student's t-test is * $P<0.01$.

Figure 15:
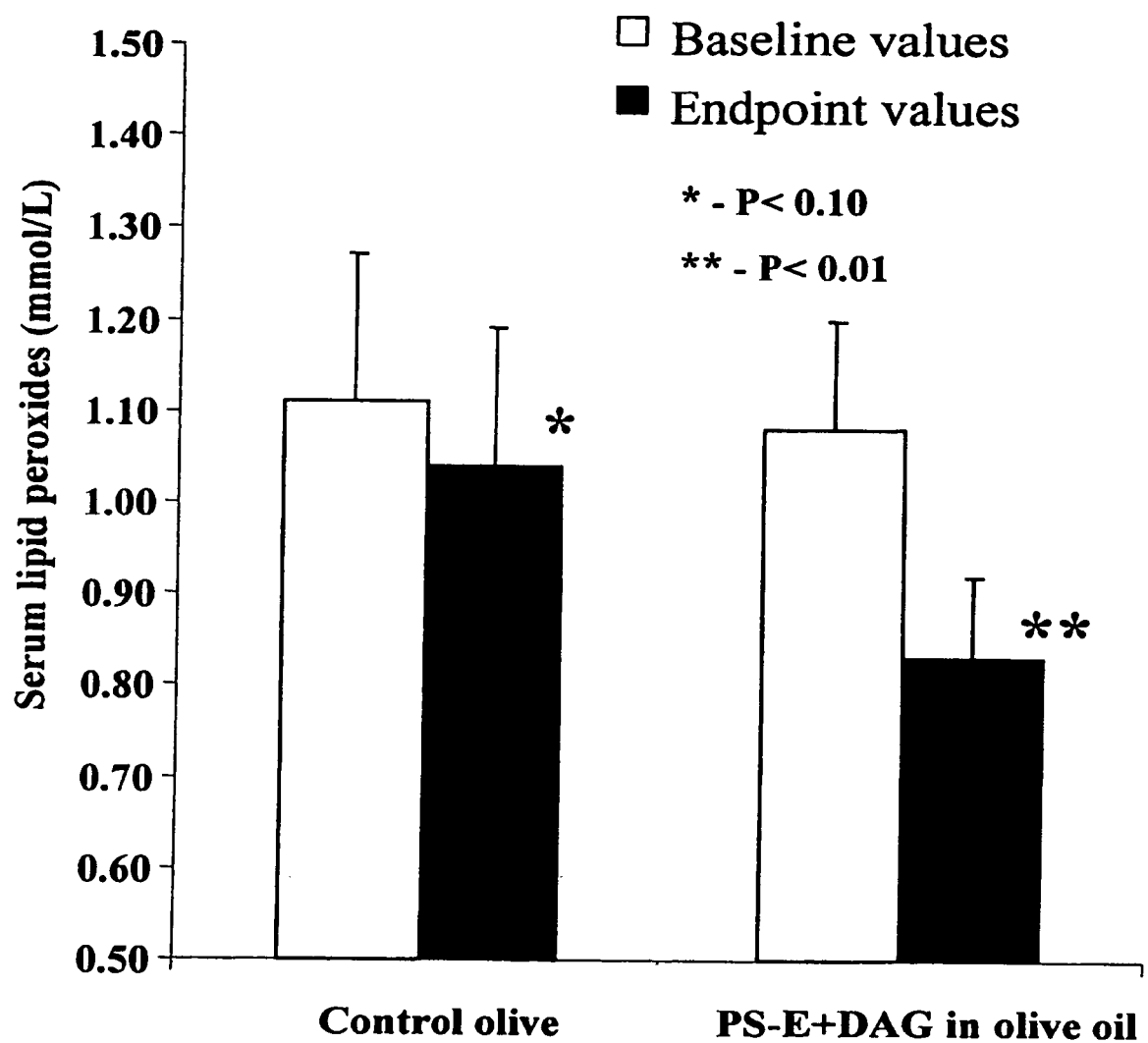

FIG. 15: Change in serum lipid peroxides concentrations

Hypercholesterolemic overweight volunteers were fed for four weeks with control olive oil diet or PS-E+DAG in olive oil followed by four weeks of washout and counter supplementation. TBARS levels were tested at the beginning (open squares) and at the termination (closed squares) of each phase as described in methods. Values represent mean±SEM of the TBARS concentrations in 21 patients. Statistical significance between baseline and endpoint values as found by Student's t-test is * P<0.10 or **P<0.01.

Figure 16:
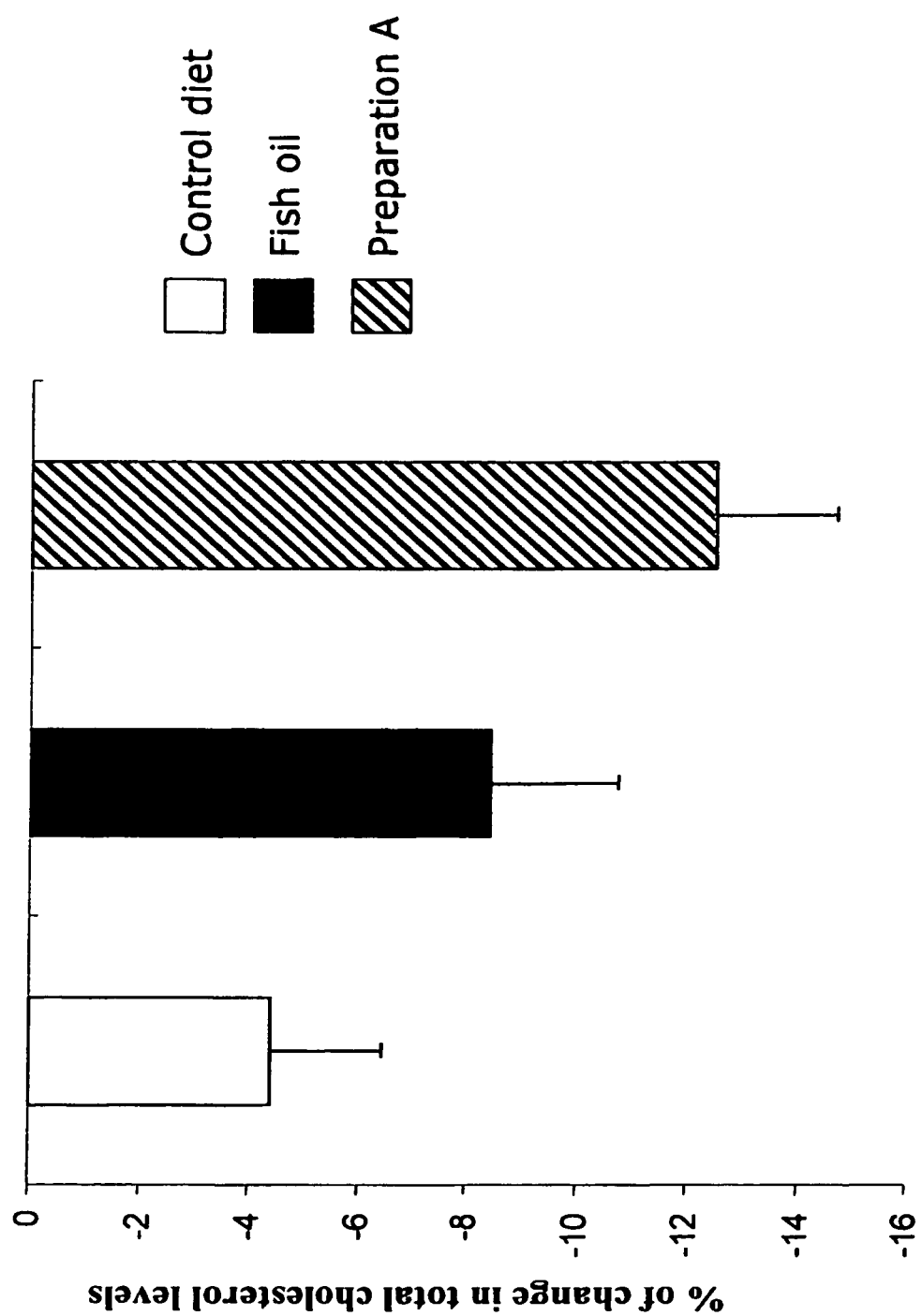
Figure 17:
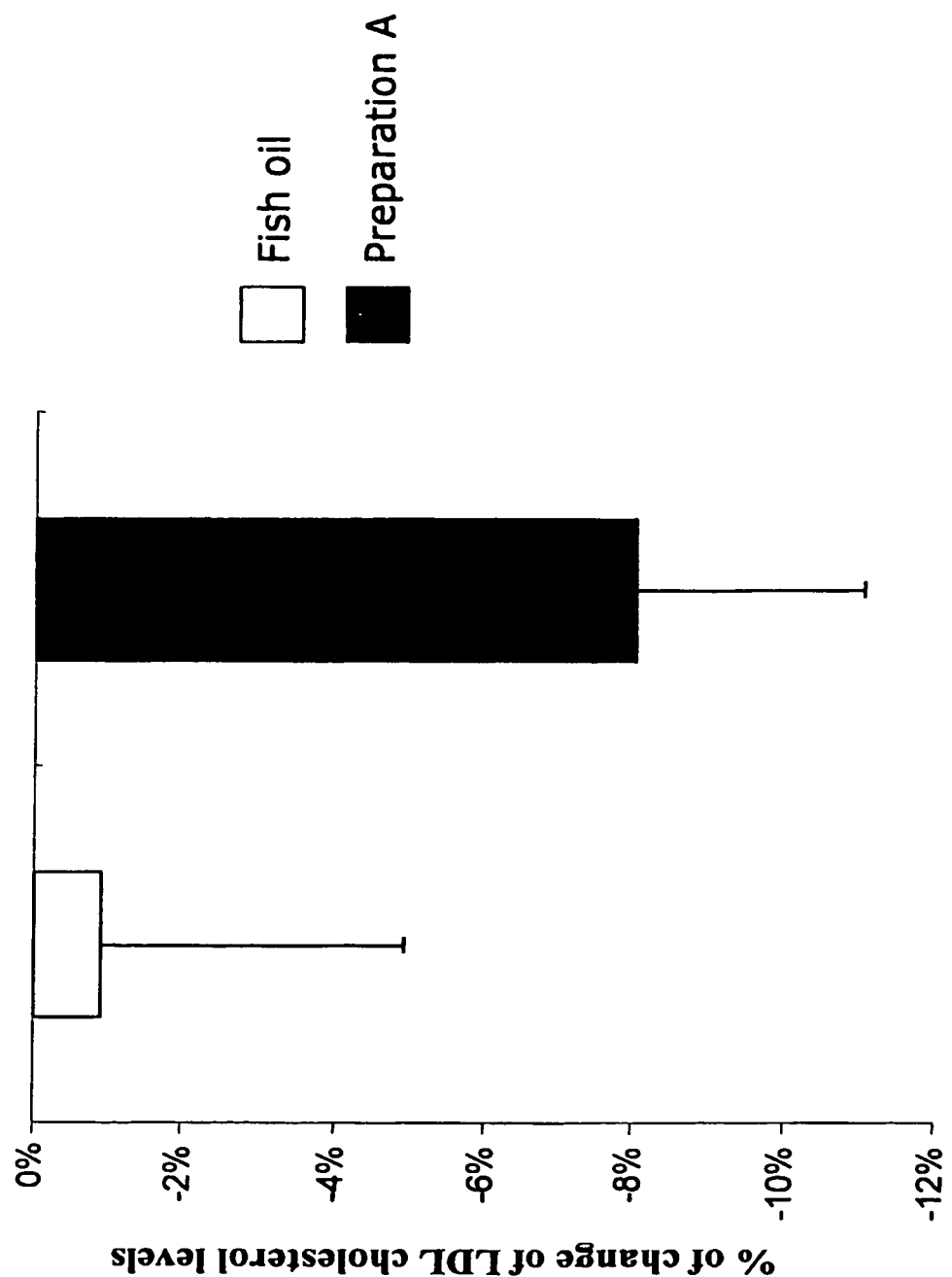
Figure 18:
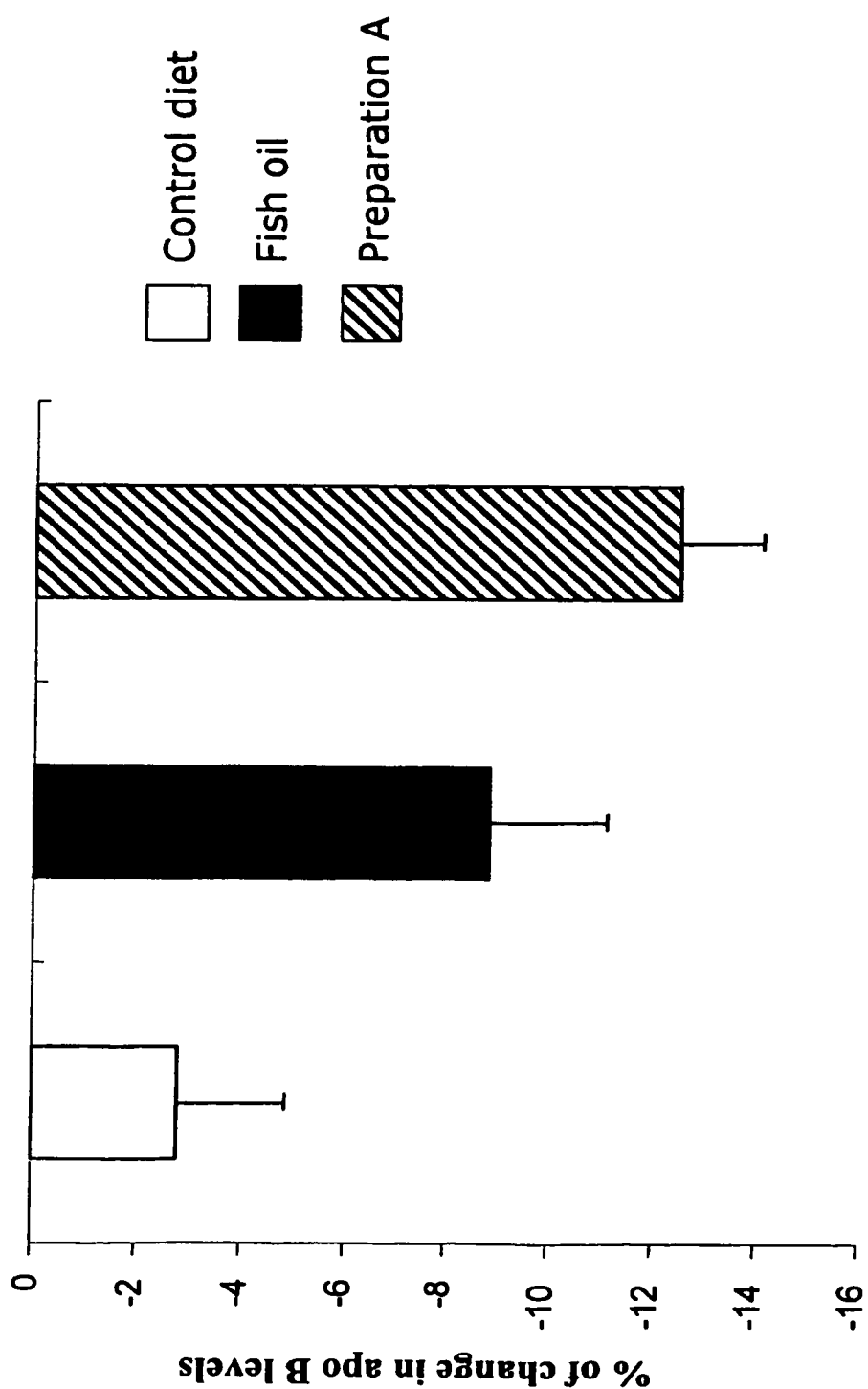
Figure 19:
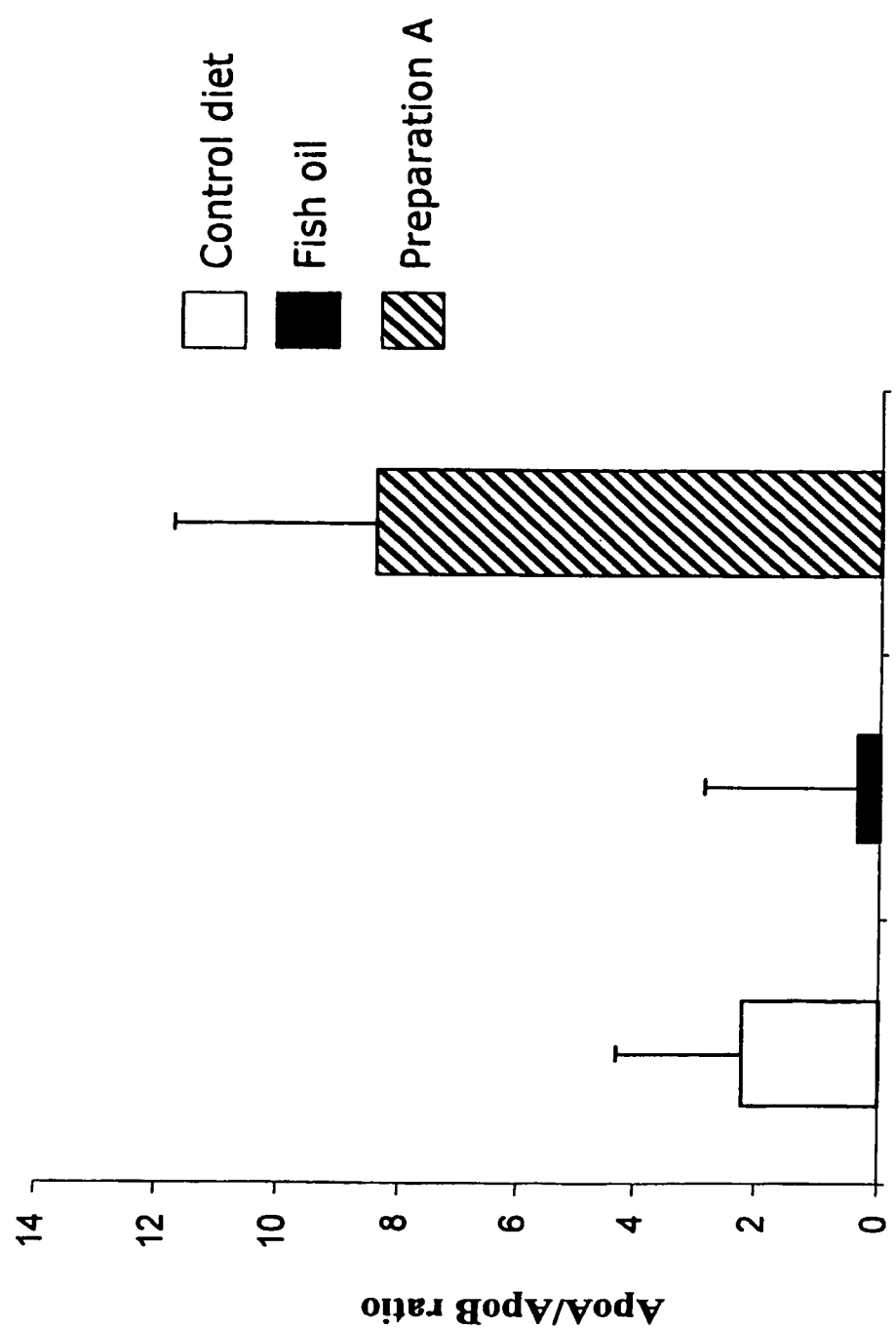
Figure 23:
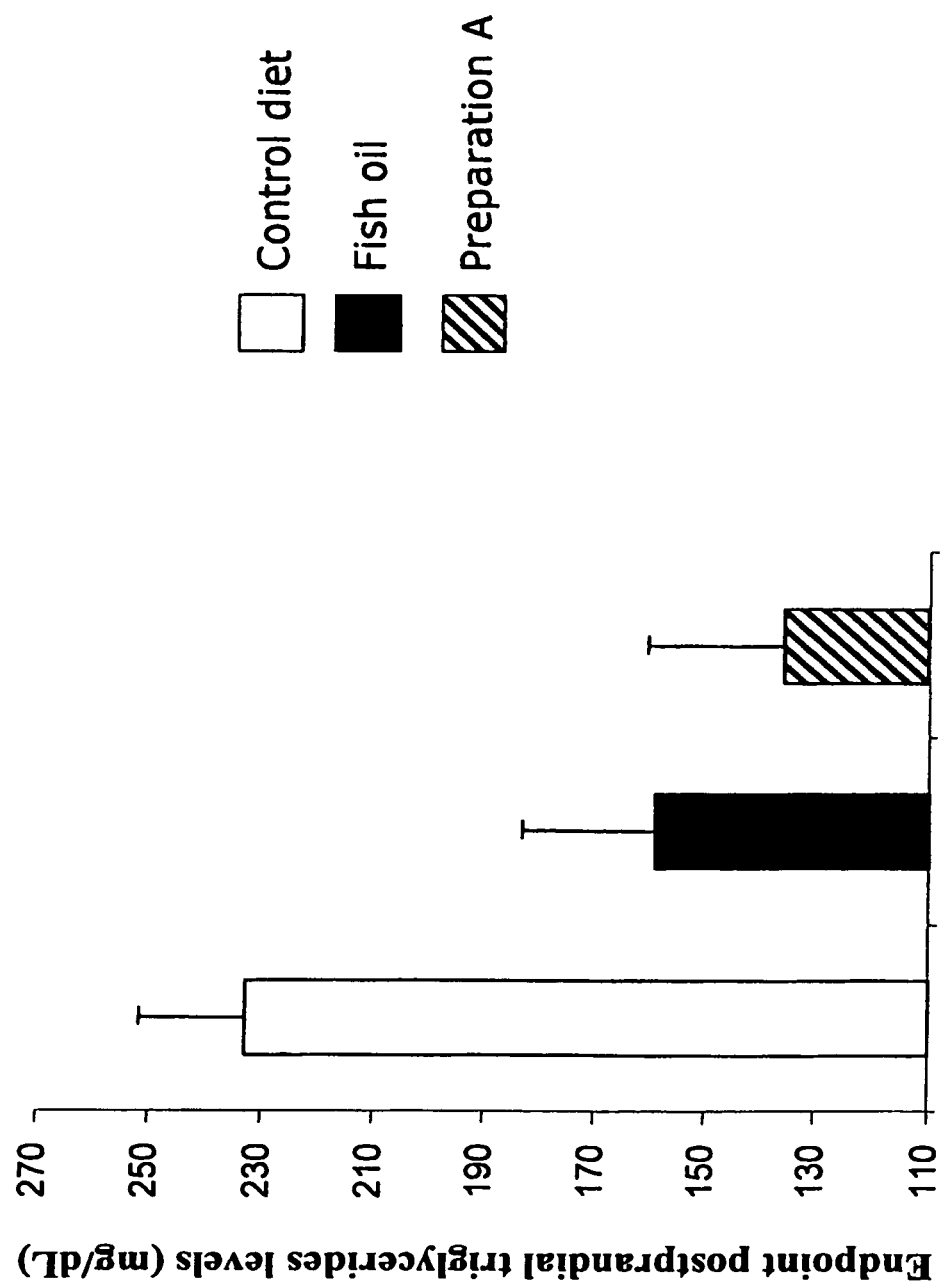
Figure 24:
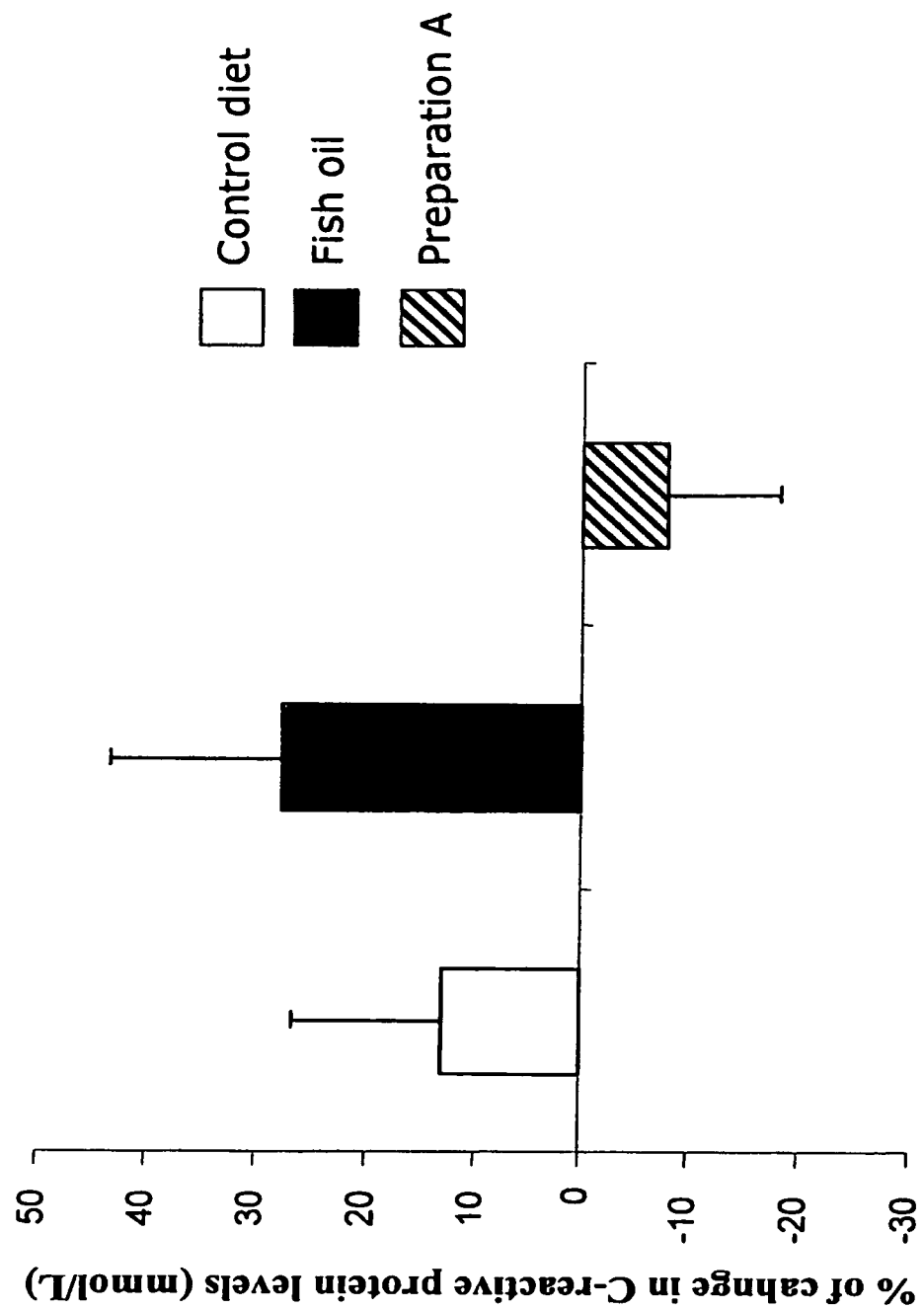
Figure 25:
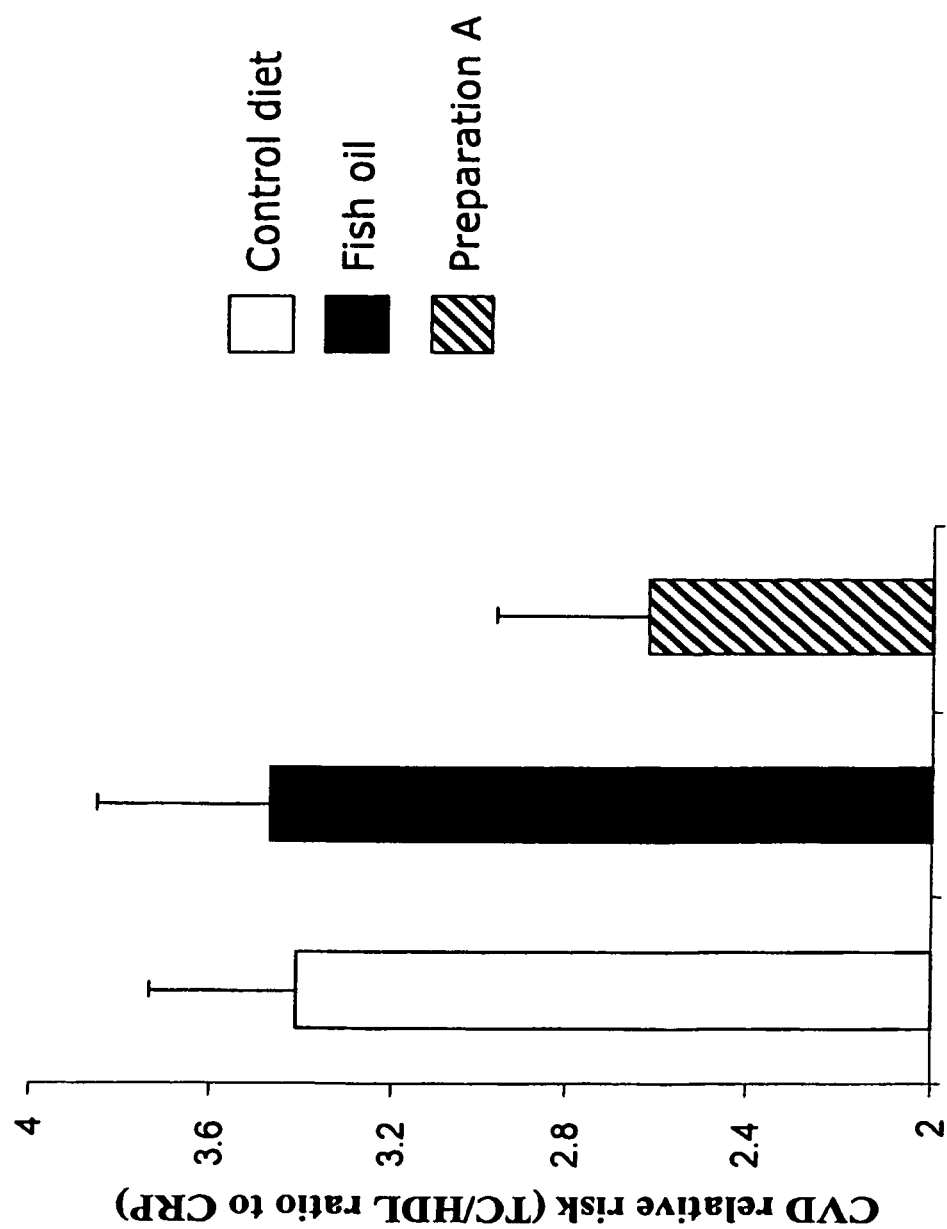

FIG. 16: Change in total cholesterol concentrations.
Preparation a vs. Fish oil vs. control.
FIG. 17: Change in LDL-cholesterol concentrations.
Preparation A vs. Fish oil.
FIG. 18: Change in apoB concentrations.
Preparation A vs. Fish oil vs. control.
FIG. 19: Change in apoA/apoB ratio.
Preparation A vs. Fish oil vs. control.
FIG. 20: Change in total to HDL cholesterol ratio.
Preparation A vs. Fish oil vs. control.
FIG. 21: Changes in HDL cholesterol sub-fractions.
Preparation A vs. Fish oil vs. control.
FIG. 22: Change in fasting triglycerides concentrations.
Preparation A vs. Fish oil vs. control.
FIG. 23: Endpoint postprandial triglycerides concentrations.
Preparation A vs. Fish oil vs. control.
FIG. 24: Change in CRP concentrations.
Preparation A vs. Fish oil vs. control.
FIG. 25: Endpoint relative risk according to Total/HDL cholesterol and CRP concentrations.
Preparation A vs. Fish oil vs. control.

DETAILED DESCRIPTION OF THE INVENTION

The following abbreviations and definitions are used along the specification:

| | |
|---|---|
| AI: | Acceptable intake |
| ATP III: | Adult Treatment Panel III (also appears as ATP 3) |
| Canola composition: | PSE + DAG in a canola oil base. |
| CHD: | Coronary heart disease |
| CRP: | C-reactive protein |
| CVD: | Cardiovascular disease |
| DAG: | Diacylglycerol(s), mainly 1,3-diacylglycerols |
| DCF | Dichlorofluorescin |
| DHA: | Docosahexaenoic acid |
| EPA: | Eicosapentaenoic acid |
| Fish oil composition: | PSE + DAG in a fish oil base. |
| HBSS: | Hanks' Balanced Salts Solution |
| HDL: | High density lipoproteins |
| HDL-C: | HDL cholesterol |
| IHD: | Ischemic heart disease |
| LC-PUFA: | Long chain PUFA |
| LDL: | Low density lipoproteins |
| LDL-C: | LDL cholesterol |
| MPM: | Mouse peritoneal macrophages |
| MUFA: | Monounsaturated fatty acid |
| Olive oil composition: | PSE + DAG combination in an olive oil base. |
| Ox-LDL: | Oxidized LDL |
| PBS: | Phosphate Buffered Saline |
| PE: | Phytosterol ester |
| PMA: | Phorbol myristate acetate |
| PSE: | Phytosterol or phytostanol ester(s) |
| PSE + DAG combination: | A combination of diacylglycerol(s) (DAG), mainly 1,3-diacylglycerol(s) and phytosterol and/or phytosterol esters (PSE) |
| PSE + DAG composition: | A composition of diacylglycerol(s) (DAG), mainly 1,3-diacylglycerol(s) and phytosterol and/or phytosterol esters (PSE) in an oil and/or fat base. |
| PUFA: | Polyunsaturated fatty acids |
| RDA: | Recommended daily allowance. |
| RDI: | Recommended daily intake |
| TG: | Triglyceride/s |
| VLDL: | Very low density lipoproteins |

The present invention relates to various lipid-soluble agents, dietary nutrients, food supplements and nutraceuticals, intended for the treatment and prevention of diseases and conditions associated with lipid metabolism.

In the present invention, the active agents are primarily mixtures of esters of LC-PUFA, the esters being phytosterol and/or phytostanol esters, together with esters of the LC-PUFA with glycerol, which may be LC-PUFA mono-, di- and/or triglycerides.

The present inventors used the animal model system apoE$^0$ mice, in which severe hypercholesterolemia and atherosclerotic plaques are generated at an early age to evaluate the anti-atherosclerotic properties of novel edible compositions, herein referred to as PSE+DAG-(olive), PSE+DAG-(canola) and PSE+DAG-(fish), in comparison with placebo and/or with canola oil.

As mentioned above, the inventors found that a combination of DAGs, mainly 1,3-DAGs and PSE in oil and/or fat, provides an enhanced effect, by decreasing both LDL-cholesterol and triglycerides levels in the blood. This combination, and compositions comprising the same, further exhibits increased serum, serum LDL and macrophage anti-oxidative properties, as well as inhibiting the formation of foam cells and/or preventing the deleterious effects generated by lipid-induced oxidative stress, which result in reduction of the risk for CHD and arteriovascular-related diseases, like, e.g., diabetes. These results were confirmed in a human study, as presented below.

While some mixtures of the kind have been described before, the present inventors have now found that such known mixtures have specific finely tuned activity in lowering the blood levels of various particular lipids, and can thus be used for the treatment or prevention of medical and physiological conditions associated with pathologically or abnormally increased levels of such lipids, or elevate levels of other lipids, and thus be used in the treatment or prevention associated with pathologically or abnormally reduced levels of such lipids. These novel uses will be described in detail below.

In addition, the present invention relates to some novel compositions of matter being lipid mixtures, essentially mixtures of esters of LC-PUFA with glycerol, which may be LC-PUFA mono-, di- and/or triglycerides, which may be derived from any suitable animal, plant, algae or microorganism source, with increased content of phytosterol or phytostanol esters, which can be used for lowering blood cholesterol and triglycerides levels, as well as for the novel uses to be described below.

Thus, the present invention relates to various therapeutic uses of the above mixtures, as well as to some such novel mixtures. The novel mixtures of the invention also have particular advantages in delivering relatively high quantities of phytosterols and LC-PUFAs, and can be used in specific dosage unit forms.

The mixtures used in the present invention consist essentially of phytosterol and/or phytostanol ester(s) of LC-PUFAs in mixture with acylglycerol(s), which may be mono-, di- or triacylglycerols. The glycerides are preferably mainly 1,3-diacylglycerols and triglycerides. The mixtures can also contain free sterols. The content of triglyceride esters of LC-PUFA in the mixtures of the invention is higher than that of diglyceride esters of LC-PUFA. It is to be noted that the fraction of glyceride esters of LC-PUFA (omega-3 fatty acids), may also contain esters of fatty acids other than omega-3 fatty acids. Usually, the glyceride esters mixtures used by the present invention are of high concentrations of DHA/EPA, and most of the LC-PUFA glyceride esters are of these acids. The same applies to the phytosterol ester fraction, which although predominantly comprises esters of LC-PUFA, may contain esters of other fatty acids.

The mixture preferably comprises at least 10 wt % LC-PUFA acylglycerol(s), of which at least 5% are diacylglycerols, and at least 5 wt % phytosterol and/or phytostanol ester(s) dissolved or dispersed in said oil and/or fat. It is to be mentioned that throughout this application, whenever referring to % of PUFA in the composition of the invention or in fish oils, it is to be taken to mean % of LC-PUFA from total fatty acids, and not weight percent from total weight of composition.

The amount of diacylglycerol(s) contained in the mixtures may range from 2 wt % to about 40 wt %, preferably from about 4 wt % to about 25 wt % and most preferably from about 6 wt % to about 22 wt %.

The amount of phytosterol and/or phytostanol ester(s) contained in the oil may range from 5 wt % to about 85 wt %, preferably from about 20 wt % to about 70 wt % and most preferably from about 25 wt % to about 65 wt %.

The diacylglycerol(s) consist substantially of 1,3-diacylglycerol(s) which mainly contain omega-3 unsaturated fatty acid residues. The structure of the diacylglycerol(s) depends on the particular oil or oil concentrate used for mixing with the phytosterol ester(s) or for producing the phytosterol esters. Preferably, fish oil concentrates containing more than 30%, preferably more than 50%, more preferably 60-80% LC-PUFA, particularly DHA and EPA, may be used. Other oils rich in omega-3 fatty acids, preferably EPA and DHA, from another source, such as other animal, plants, algae or microorganisms are suitable.

The phytosterol and/or phytostanol ester(s) may be any phytosterol and/or phytostanol ester. Examples of such esters are stigmasteryl, sitosteryl and beta-sitosteryl esters of DHA and EPA.

The ratio between the glyceride esters and the sterol esters can vary from about 19:1 to 1:9, preferably from 9:1 to 1:9, more preferably from 9:1 to 1:3, even more preferably from 3:1 to 1.5:1.

The ratio between the diacylglycerol(s) and the sterol esters can vary from about 1:40 to 1.5:1, preferably from 1:11 to 1:1.5, more preferably from 1:9 to 1:3.

Thus, the principal candidates for inclusion as an ester attached to, e.g., sitosterol and campesterol, are the fish oil fatty acids EPA and DHA. It is proposed that esterification of plant sterols with EPA and DHA not only improves the efficacy of the plant sterols by more aggressive exclusion of cholesterol from the micelle in the intestine, but also delivers to body cells fatty acids of the omega-3 class, which are considered to possess several health benefits over and above their function in lowering circulating triglyceride levels. Such beneficial effects include improvement of immune function and risk reduction for diseases including cancer, diabetes and arthritis. As will be discussed in detail, the multifunction mixtures of the invention confer therefore a portfolio of beneficial effects to health and well being.

The mixtures of the invention can be prepared by reacting fish oil with free phytosterols using enzyme catalysis to affect the in situ esterification of the phytosterols with fatty acids of the fish oil. The enzyme can be a lipase enzyme, preferably immobilized and/or preferably coated, as described in Applicant's WO00/56869. Specific procedures are described in WO03/064444. The phytosterols can be of plant source, preferably soybean phytosterols or wood sterols. The sterols can be either sterols or stanols (the terms phytosterol and phytostanols are used herein interchangeably). The fish oil can be of various grades and concentrations of EPA and DHA. Preferably the fish oil is rich in DHA/EPA, preferably higher than 30%, preferably higher even than 50%. The fish oil can contain just EPA or just DHA or a mixture of these fatty acids at different ratios. Preferably the fish oil contains higher levels of DHA than EPA. The omega-3 fatty acids containing oil can also be any oil rich in these fatty acids, such as microbial or algae oils rich in EPA and DHA. Other plant or animal sources of such oils are also within the scope of the invention.

Generally, the immobilized enzyme is added to a stirred mixture of free sterols and fish oil at room temperature or at elevated temperature, preferably above 30° C., more preferably between 30 and 60° C. The reaction mixture is stirred continuously for several hours. The reaction is followed by standard and appropriate analytical tools, such as HPLC, GC, TLC, NMR, MS, etc. Upon completion of the reaction, the reaction mixture is filtered to remove the catalyst. The filtrate can be used as the active mixture. Preferably the filtrate is treated by standard oil processing techniques to remove free fatty acids, to maintain satisfactory peroxide value, to improve color, etc. Treatment may include distillation, steam deodorization, molecular distillation, bleaching, etc. Additives, such as antioxidants can be added to the final mixture to maintain its stability and quality.

Alternatively the active mixture of the invention, i.e. the Omega-3-esters mixture, can be prepared chemically by catalyzing the above mentioned reaction with metal alkoxides, preferably with sodium methoxide. This basic catalyst also confers transesterification that yields phytosterol esters where the fatty acids of said esters are from the fish oil. In this route, the reaction, upon its completion, is neutralized by standard techniques, preferably by washings with an acidic aqueous solution. These washings can be further followed by washings with water to maintain neutral pH levels. The active mixture is then further processed as above.

In both procedures the level of phytosterol esters in the final mixture can be controlled by the amount or percentage of free sterols added to the fish oil. Levels of up to 70% can be easily obtained by these methods.

These in situ procedures yield as a by-product diglycerides, which are also ingredients of said mixture. The level of diglycerides is also controlled by the level of sterols used since the transesterification reaction yields stoichiometric amounts of partial glycerides.

The active ingredient can also be prepared by esterifying free sterols with a source of omega-3 fatty acids, preferably DHA and EPA. This source can be alkyl esters of omega-3 fatty acids, preferably ethyl or methyl esters. The reaction is carried out enzymatically or chemically, as described above. The resulting phytosterol esters are purified from the alkyl esters by conventional methods and then mixed with fish oils or other DHA/EPA-rich oils, which preferably may contain partial glycerides, particularly diglycerides.

Another aspect of the invention relates to a novel use of a combination comprising diacylglycerols and phytosterol and/or phytostanol ester(s) as an agent capable of reducing blood levels of both cholesterol and triglycerides and/or for lowering serum, serum LDL and macrophage oxidation levels, inhibiting the formation of foam cells and/or preventing the deleterious effects generated by lipid-induced oxidative stress.

The combination described in Examples 1-3 consists essentially of phytosterol and/or phytostanol ester(s) and diacylglycerol(s), mainly 1,3-diacylglycerols, preferably dispersed in an edible oil and/or fat, wherein the ratio of PSE to DAG is at least 1. More particularly, the combination comprises at least 1 wt % diacylglycerol(s) and at least 1 wt % phytosterol and/or phytostanol ester(s) dissolved or dispersed in said oil and/or fat.

The amount of diacylglycerol(s) contained in the oil and or fat may range from 1 wt % to about 99 wt %, preferably from about 7 wt % to about 48 wt % and most preferably from about 10 wt % to about 22 wt %.

The amount of phytosterol and/or phytostanol ester(s) contained in the oil may range from about 1 to about 99 wt %, preferably from about 5 to about 70 wt %, more particularly from about 7 to about 60 wt %, specifically from about 10 to about 60 wt %, more particularly from about 7 to about 35 wt % and more specifically from about 20 to about 35 wt %.

The diacylglycerol(s) consist substantially of 1,3-diacylglycerol(s). The fatty acid profile of the diacylglycerol(s) depends on the particular oil and/or fat used for producing the PSE and DAG combination. For example, when olive oil is used, the diacylglycerols mainly consists of 1,3-dioleyl glycerol. Generally speaking, fatty acid moieties of the DAG may include, for example, caproic, caprylic, myristic, oleic, palmitic, palmitoleic, stearic, linoleic, linolenic, eicosanoic fatty acids and docosanoic fatty acids, but may contain other fatty acyls.

The phytosterol and/or phytostanol moiety of the corresponding esters of the combination of the invention may be any phytosterol or phytostanol derivative. These phytosterols and/or phytostanols can be from soy, wood, algae, and other plants, as well as from animal or microbial sources that contain phytosterols and/or phytostanols. Examples of phytosterols and/or phytostanols include but are not limited to beta-sitosterol, stigmasterol, campesterol, brassicasterol, beta-sitostanol, campestanol, and stigmastanol.

With regards to the fatty acid moiety of the fatty acid phytosterol and/or phytostanol esters of the PSE+DSG combination, it may include any fatty acid and more preferably different fatty acids characterizing the source of the fatty acids. Such source may be a natural, synthetic, or fractionated oil or fat used in the interesterification of said phytosterols and/or phytostanols. In other examples the source of the fatty acids may be any other esters of fatty acids, such as alkyl esters of fatty acids, preferably ethyl or methyl esters, or free fatty acids. The fatty acids may include, but are not limited to, caproic, caprylic, myristic, oleic, palmitic, palmitoleic, stearic, linoleic, linolenic, eicosanoic fatty acids and docosanoic fatty acids. It should be emphasized that in a preferred embodiment the combination of the invention is produced by the in situ esterification, chemical or enzymatic, of a preferred oil and/or fat with a source of phytosterols and/or phytostanols, simultaneously yielding diglycerides (DAG) and thus obtaining the combination of the invention in which the fatty acid profile of the DAG and the fatty acids of the sterol or stanol esters corresponds to the fatty acid profile of the preferred oil and/or fat used for the interesterification. In this process, the resulting combination is dissolved or dispersed in the source oil and/or fat and can optionally be further purified. The combination of the invention may also be obtained by separately producing phytosterol and/or phytostanol esters with a preferred source of fatty acids and combining said phytosterol and/or phytostanol esters with DAG. The latter can be commercially available or produced by conventional chemical or enzymatic processes, including hydrolysis, alcoholysis, transesterifications or interesterification processes. The fatty acid profile of the DAG of the combination of the invention corresponds to the fatty acid profile of the source oil and/or fat used in their preparation.

The weight ratio of phytosterol and/or phytostanol ester(s) to diacylglycerol(s) in the combination or composition of the invention is at least 1:1. This weight ratio may be from about 15:1 to about 1:1, preferably about 10:1 to about 1:1, more preferably 5:1 to 1:1 and particularly about 2:1. As used in the context of this application, ratios between various constituents are to be taken as weight ratios, unless specified otherwise.

The oil comprised in the PSE+DAG composition of the invention may be any edible oil, including, but not limited to olive oil, soybean oil, sunflower oil, safflower oil, canola oil, sesame oil, palm oil, avocado oil or fish oil. Preferably the oil is at least one of olive oil, canola oil or fish oil. The fat contained in the composition of the invention may be any suitable fat, such as, e.g., butter fat, anhydrous milk fat, cocoa butter, as well as animal fat such as lard or a fish oil concentrate.

The diacylglycerol(s) may be obtained by any conventional enzymatic or non-enzymatic procedure. Preferably, they are obtained by inter-esterification reaction between phytosterol(s) and triglyceride(s) present in the oil and/or fat. The phytosterol and/or phytostanol ester(s) may be obtained by any conventional enzymatic or non-enzymatic procedure. Preferably, these constituents are obtained by interesterification reaction between phytosterol(s) and/or phytostanol and triglyceride(s) present in an edible oil or fat. A process for obtaining the combinations used by the present invention is described in detail in WO03/064444, fully incorporated herein by reference.

As shown in the following examples, a significant effect of the tested compositions in preventing and/or reducing serum ox-LDL, as well as macrophage oxidation was obtained. Thus, in addition to having an effect in reduction of blood LDL-cholesterol and triglycerides levels, the said combination, and compositions comprising the same, exhibit serum LDL and macrophage anti-oxidative properties. The examples further show that preparation of PSE+DAG in olive oil, canola oil and/or fish oil exhibited significant anti-oxidative properties, inhibiting the formation of foam cells, and/or preventing the deleterious effects generated by lipid-induced oxidative stress.

Specifically, FIGS. 5, 7, 8 and 9 demonstrate how the different PSE+DAG preparations lowered the following oxidative stress parameters: serum oxidative stress, ox-LDL uptake by peritoneal macrophages, macrophage oxidative status, and PMA-induced superoxide anions release from macrophages.

Figure 6:
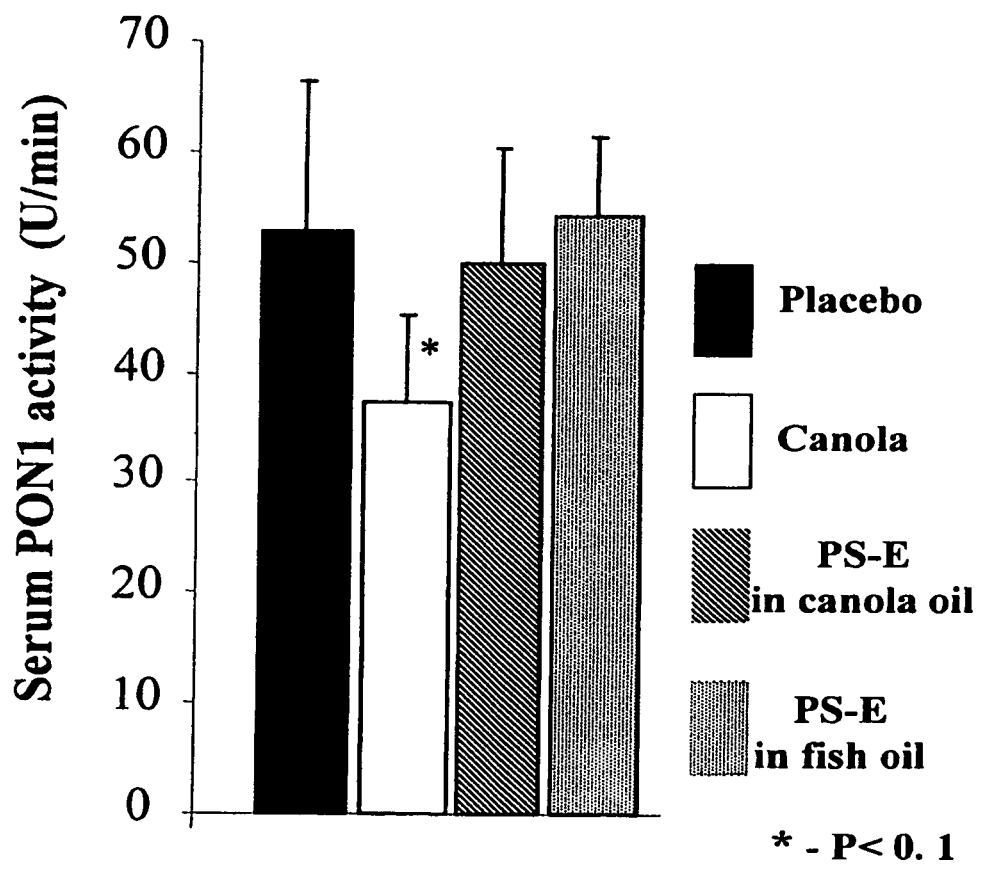

PON1 activity in the serum was also measured. PON1 is an HDL-associated esterase that can eliminate ox-LDL. Interestingly, the results of FIG. 6 show that while canola oil reduces PON1 activity, the PSE+DAG combinations of the invention were able to maintain PON1 higher levels, suggesting that the combination of the present invention may protect PON1 activity in a pro-atherosclerotic environment.

The combinations/compositions of PSE+DAG were most effective in reducing total cholesterol (see FIG. 10) and LDL cholesterol plasma levels (see FIG. 11) as well as fasting triglycerides levels (see text below and Example 3).

In addition, subjects who consumed the combination/composition of the invention showed a pronounced reduction of apo B values (FIG. 12). Consequently, there was also a positive change, i.e. decrease, in apoB/apoA ratio. Apo B, apo A-I and the apo B/apo A-I ratio have been reported as efficient predictors of cardiovascular events than LDL-C and as may be seen from FIG. 13, in addition to the aforementioned reduction in apo B levels, introducing PSE+DAG to the base MUFA-enriched diet consumed by the volunteers resulted in significantly reduced levels of apoB/apoA ratios.

Lipoprotein(a) (Lp(a)) is an LDL-like particle to which apo A is attached through a disulfide bond to apo B. Increased plasma levels of Lp(a) are an independent predictor of the presence of angiographically documented and clinical CAD, particularly in patients with hypercholesterolemia [Danesh J., et al. (2000) *Circulation* 102:1082-1085]. In the present human study, hypercholesterolemic volunteers fed with control diet presented significantly elevated levels of Lp(a) (FIG. 14).

The present human study also demonstrates a pronounced and significant reduction in plasma oxidative stress levels (FIG. 15).

In Example 4, the inventors have now established various activities of the Omega-3-esters mixture of the invention (Preparation A).

Cholesterol and Lipoproteins

As shown in FIG. 16, a substantial decrease in total cholesterol concentrations was observed following the fish oil treatment, while control diet consumption induced a significant though smaller hypocholesterolemic effect. In terms of reduction of absolute cholesterol concentrations, the volunteers that consumed these diets reduced 21 mg/dL and 13 mg/dL; from initial average level of 241 mg/dL and 240 mg/dL to a final average levels of 220 mg/dL and 228 mg/dL, respectively. With respect to the American Heart Association (AHA) recommendations, as were expressed in the Third Report of the Expert panel on Detection, Evaluation, and Treatment of High Blood Cholesterol in Adults (Adult Treatment Panel III or ATP III) released in 2001, the desirable total cholesterol levels in healthy individuals should be below 200 mg/dL. Remarkably, treatment with Preparation A of the invention resulted in the largest change in total cholesterol compared to diets containing no supplemented plant sterols (−12.52% versus −8.45% and −4.40%; P-Value=0.039). Importantly, the decreases in total cholesterol levels induced by Preparation A could be regarded as reducing 72% of the total cholesterol levels towards the recommended ATPIII guidelines (from 243 mg/dL to 212 mg/dL).

These effects are interesting from a physiological point of view and in accordance with the existing data on the hypocholesterolemic effect of plant sterols. Indeed, plant sterols, at a dose ranging from 1.5 to 2.5 g/day, have been reported to decrease total cholesterolemia, due mainly to a 10% decrease in LDL cholesterol levels [Katan et al. (2003) *Mayo Clin. Proc.;* 78:965-78]. Moreover, in a recent review of fish oil supplementation effect on lipids levels in diabetic type 2 patients [Montori et al. (2000) *Diabetes Care;* 23:1407-1415] a fairly minor effect was demonstrated for altering total cholesterol levels (+0.4 mg/dL [95% CI −50 to +5.8]). Interestingly, when comparing patients with plasma cholesterol levels above 265 mg/dL at entrance to the study (n=6) that consumed fish oil to Preparation A, a significant beneficial effect of the Preparation A diet was observed on absolute or % of change (P=0.04) in total cholesterol levels. Thus, the mixtures of the invention, and particularly Preparation A, are Useful in Lowering Cholesterol Levels.

As shown in FIG. 17, this hypocholesterolemic effect of Preparation A was more prominent, as expected, in the reduction of LDL cholesterol plasma levels, while fish oil consumption resulted in an elevation of LDL cholesterol concentrations, compared to the reduction in LDL cholesterol obtained by the control diet. Fish oil has been previously shown to induce an increase in LDL cholesterol concentrations [Harris et al. (1991) *J Am Coll Nutr.;* 10(3):220-7]. This increase in LDL cholesterol levels may be associated with larger LDL molecules of lower density. In the present study, Preparation A attenuated the increasing effect of fish oil on LDL cholesterol (from 158 mg/dL to 144 mg/dL; P-Value=0.006). Indeed, the changes in the LDL-cholesterol concentrations after supplementation with Preparation A were statistically different from those observed after fish oil supplementation (−8.04% versus −0.93%, respectively; P<0.05). However, the multiple comparison of Preparation A and fish oil with the control diet resulted in a fairly mild tendency (P=0.322), most probably due to the variation within the treatments groups. Nonetheless, a paired analysis of the effect of Preparation A on LDL-cholesterol compared to the control diet had demonstrated a marked tendency (8.04% versus 4.13%; P-value=0.15). In terms of ATPIII recommendations for LDL-cholesterol, which are set, for subjects who do not have coronary heart disease or diabetes, to be less than 130 mg/dL, treatment with Preparation A resulted in 49% reduction of the amounts of LDL cholesterol required to reach this goal, while the control diet and the fish oil treatment induced 31% and 15% reduction, respectively. The mixtures of the invention are thus not only useful in lowering total cholesterol, but advantageously reduce levels of LDL cholesterol.

Moreover, type 2 diabetes is frequently associated with dyslipidemia. Recently, it was found that small dense LDL particles are often present in type 2 diabetes [Sniderman et al. (2001) *Ann. Int. Med.* 135:447-459]. Although abnormal LDL composition has gained notice, much less attention has been paid to the issue of LDL particle number. This gap in knowledge is important because it was suggested that in diabetics there are increased numbers of small dense LDL particles in association with hypertriglycerides. This combination constitutes of hypertriglyceridemic and hyper-apoB, is one of the most common dyslipidemias associated with premature vascular disease.

As shown in FIG. 18, the mixture of the invention had a more pronounced reduction effect on endpoint apolipoprotein $B_{100}$ (apoB) concentrations (−12.52%), compared to the effect obtained by un-reacted fish oil (−8.84%) or control diet (−2.27%). The compositions of the invention, where the preferred embodiment is preparation A, may thus be useful in reducing apoB concentration. The effect of fish oil on apoB concentrations is still unclear. Previous studies have shown decreased [Sanchez-Muniz et al. (1999) *Eur J. Nutr.;* 38(1): 20-7) or increased apoB levels after fish oil supplementation [Calabresi et al. (2004) *Metabolism;* 53(2):153-8]. The present results suggest that the omega-3 esters mixture of the invention may decrease the number of circulating atherogenic apoB-containing lipoproteins after one month of supplementation as a combined effect of the plant sterols and fish oil. The mixture could be particularly important to diabetics, as $apoB_{100}$ levels were shown to be associated with the metabolic syndrome and, possibly, to insulin-insensitivity in Type 2 diabetes patients [Relimpio et al. (2002) *Diabetes Res. Clin. Practice;* 57(3): 199-207].

As shown in FIG. 19, when the omega-3 esters mixture of the invention (Preparation A) was compared to the fish oil and control diets, significant differences were observed between the effects of treatment on apoA/apoB ratios absolute changes (0.09, −0.01 and 0.02, respectively; P=0.039) and % change (8.45%, 0.35% and 2.20%, respectively; P=0.09). This effect could be attributed to the relative maintenance of apoA concentrations while generating a significant decrease in apoB levels as a result of supplementation with mixtures of omega-3 esters. Interestingly, a paired analysis between the mixture of omega-3 esters and the fish oil consumption had suggested a distinct difference between the effects of these supplements (P-Value=0.005). Apo B, apo A-I and the apo B/apo A-I ratio have been reported as better predictors of cardiovascular events than LDL-C and they even retain their predictive power in patients receiving lipid-modifying therapy [Walldius et al. (2004) *J Intern Med.;* 255 (2): 188-205].

When fish oil was trans-esterified with plant sterols (Preparation A) and compared to the consumption of the control diet, a significantly decreased total/HDL cholesterol ratio was demonstrated (compared to fish oil and control diet; see FIG. 20). These results suggest that the trans-esterification with plant sterols not only counteracts the increase in total/HDL cholesterol ratio, but may confer to omega-3 LC-PUFA a beneficial impact on cholesterol profile, which is not observed with un-reacted fish oil. This reduction in total cholesterol/HDL cholesterol ratio with the omega-3 esters mixture of the invention may be of particular interest for patients presenting both elevated triglyceride levels and total/HDL cholesterol ratios. The importance of this parameter was demonstrated in the Quebec cardiovascular study [Lemieux et al. (2001) *Arch Intern Med.;* 161(22):2685-92], in which it was concluded that the variation in the total/HDL cholesterol ratio may be associated with more substantial alterations in metabolic indices predictive of ischemic heart disease risk (IHD) and related to the insulin resistance syndrome than variation in the LDL-C/HDL-C ratio. Given the beneficial impact of the mixtures of omega-3 esters on reducing the total/HDL cholesterol ratio and apoB concentrations, the omega-3 esters mixture of the invention seems to be a promising alternative to fish oil treatment in hypertriglyceridemic patients with elevated cholesterol levels.

As demonstrated in the present study, feeding hypercholesterolemic subjects for a limited period with either control diet or fish oil had no effect on the $HDL_2$ subfraction levels. However, supplementation with the omega-3 esters mixture of the invention (Preparation A) resulted in a marked elevation in $HDL_2$ levels, which was shown to be significantly different than the control diet or fish oil treatment effects (FIG. 21A). The $HDL_3$ levels were reduced similarly by either the fish oil, but were not affected by the control diet consumption, as shown in FIG. 21B. Thus, the omega-3 esters mixture of the invention (Preparation A) was shown to have a potent effect on HDL subfractions. This is an important feature of the invention, which provides for use of the mixtures in the elevation of $HDL_2$, whilst reducing levels of $HDL_3$. The protective role of HDL against the development of IHD is well accepted; several prospective studies have confirmed the early observations of Barr and colleagues [Barr et al. (1951) *Am J Med.;* 11:480-493] who first suggested more than 50 years ago that individuals with elevated plasma concentrations of HDL cholesterol were at lower risk for IHD.

Generally, the HDL consists of a heterogeneous group of particles defined either by size or by apolipoprotein content. Subfractions of HDL appear to have distinct but interrelated metabolic functions, including facilitation of cholesteryl ester transfer to LDL and VLDL, modulation of triglyceride-rich particle catabolism, and, possibly, removal of cholesterol from peripheral tissues. Like HDL cholesterol, HDL subfractions are widely affected by a variety of factors. HDL subfractions augmented levels are also markers for epidemiologic risk for coronary artery disease. Specifically, results from both the Kuopio IHD Risk Factor Study and the aforementioned Quebec study have suggested that the cardioprotective effect of elevated HDL cholesterol levels may be attributed to the $HDL_2$ subfraction. Because they provide information about the physiologic processes of cholesterol metabolism, HDL subfractions are emerging as an increasingly important tool in the study of the relationship between lipids and CVD. Indeed, it was shown that obesity [Laakso et al. (1990) *Metabolism;* 39:117-22] and insulin resistance [Tilly-Kiesi et al. (1996) *Lipid Res.;* 37:1569-78] are associated with low total HDL and $HDL_2$ and a higher proportion of $HDL_3$. The reductions in HDL associated with type 2 diabetes and insulin resistance are multi-factorial, but a major factor appears to be increased transfer of cholesterol from HDL to triglyceride rich lipoproteins, with reciprocal transfer of triglyceride to HDL. Triglyceride-rich HDL particles are hydrolyzed by hepatic lipase and, as a result, are rapidly catabolized and cleared from plasma [Hopkins and Barter (1986) *J Lipid Res.;* 27:1265-77]. Krauss [Krauss (2004) *Diabetes Care;* 27:1496-1504] had indicated that typically the reduced HDL levels in plasma of patients with type 2 diabetes are manifested as reductions in the $HDL_{2b}$ subspecies and relative or absolute increases in smaller denser $HDL_{3b}$ and $HDL_{3c}$. In normolipidemic human subjects there are just a few indications on fish oil consumption resulting with HDL subfraction alterations. However, dyslipidemic diabetic subjects were reported to benefit of fish oil supplementation in a specific $HDL_2$ rising levels while $HDL_3$ shown tendency to decline, suggesting a shift in the HDL profile in the direction of larger and less dense particles [Dunstan et al. (1997) *Diabetes Care;* 20:913-921; Fashing et al. (1996) *Horm Metab Res.;* 28:230-6; Lou et al. (1998) *Diabetes Care;* 21:717-24]. Nevertheless, none of these studies in dyslipidemic patients had demonstrated comparable alterations as described in FIG. 21.

Triglycerides and Fatty Acids

The mixtures of the invention also have beneficial effects on triglycerides and fatty acid level. As shown in FIG. 22, un-reacted fish oil decreased plasma fasting triglycerides by 37.1%, while the comparable effect of the omega-3 esters mixture of the invention (Preparation A) was 42.9%. Comparing the effects of these supplements on fasting triglycerides levels to the rather mild effect of the control diet resulted in a statistically significant difference between the consumption of fish oil to olive oil. A recent meta-analysis, however, suggests that a 8.8 mg/dL increase in triglyceride concentration is associated with an increase in the frequency of CVD in both men and women [Austin et al. (1998) *Am. J. Cardiol.;* 81:7 B]. Indeed, the Adult Treatment Panel III identifies elevated serum TG concentrations as an independent risk factor [ATP III]. Clinical studies of fish oil supplementation with a parallel or cross-over study design have reported a dose-dependent triglyceride lowering effect for omega-3 fatty acids in both normolipidemic [Blonk et al. (1990) *Am. J. Clin. Nutr.* 52:120] and hyperlipidemic subjects [Davidson et al. (1997) *J. Am. Coll. Nutr.;* 16:236]. As shown in the results presented herein, consumption of the omega-3 esters mixture of the invention (Preparation A) generated a triglyceride reduction, as depicted in FIG. 22.

Similar effects, but with a higher tendency, were observed on postprandial triglyceride levels (FIG. 23), where the lowest plasma triglyceride concentrations after consumption of a meal were detected in the subjects fed with the omega-3 esters mixture of the invention compared with fish oil and control diet supplements. Interestingly, the paired analysis between the un-reacted fish oil and the omega-3 esters mixture of the invention (Preparation A) demonstrated a notable tendency between these two supplements, though the levels of the EPA and DHA were identical. It has been suggested that postprandial triglyceride concentrations are a better marker as compared to the fasting levels of triglyceride for determination of risk factor for CHD. This analysis may show a state of fat tolerance which cannot be detected by fasting triglyceride measurements [Karpe (1999) *Intern. Med.,* 246:341]. Moreover, Hansen and colleagues [Hansen et al. (1998) *Lipids;* 33:131-8] reported that healthy volunteers fed by either EPA or DHA shown that the postprandial triglyceridemia was suppressed by 19 and 49% after prolonged intake of EPA and DHA, respectively, indicating that prolonged intake of DHA is equivalent to or even more efficient than that of EPA in lowering postprandial triglyceridemia. Taking both the fasting and the postprandial triglycerides levels alterations as presented in FIGS. 22 and 23 suggest that the hypotriglyceridemic effect of fish oil fatty acids is not only retained when they are esterified to plant sterols but generates a more prominent impact on circulating lipids.

Plasma fatty acid analysis clearly indicates that following the omega-3 esters mixture of the invention (Preparation A) consumption, the level of DHA is significantly higher than that present in a subject which consumed equivalent amounts of fish oil. These levels in both omega-3 based treatments are, of course, significantly elevated compared to the control diet. As the administered levels of DHA were identical in both fish oil based treatments, these notable observations could imply a superior bioavailability of DHA esterified to plant sterols comparing to triglycerides. This suggested mode of action is further backed by the analysis of blood plant sterols levels. The increase in campesterol concentrations was more pronounced than the increase in beta-sitosterol levels, reflecting a higher absorption of campesterol. However, the omega-3 esters mixture of the invention increased sitosterol concentrations more than non-esterified sterols, suggesting a higher bioavailability of sitosterol when supplied as fish oil esters than as unesterified sterols. Diabetes was shown to impair essential fatty acid metabolism by decreasing activities of Δ6- and Δ5-desaturases, enzymes that convert dietary linoleic acid and γ-linolenic acid to long-chain polyunsaturated fatty acids (LC-PUFA), including γ-linolenic acid, arachidonic acid (AA), EPA, and DHA [Horrobin (1998) *Prostaglandins Leukot Essent Fatty Acids;* 31:181-97]. As a result, AA and DHA levels are reduced in membrane phospholipids of several tissues, including erythrocyte and sciatic nerve, in patients with type 1 diabetes and in diabetic animals [Ruiz-Gutierrez et al. (1993) *Diabetologia;* 36:850-6]. It was demonstrated recently that dietary supplementation with fish oil, containing EPA and DHA [Gerbi et al. (1999) *J. Nutr.;* 129: 207-13], partially prevented the diabetes-induced decrease in nerve conduction velocity, a physiological marker of diabetic neuropathy. This was further correlated in a recent report [Coste et al. (2003) *Diabetes;* 52(10):2578-85] that presented evidence for a marked neuro-protective effect of DHA on diabetic neuropathy.

Inflammatory Markers

Furthermore, the mixtures of the invention may have a beneficiary effect in the control of inflammatory process. C-reactive protein (CRP) is a phylogenetically highly conserved plasma protein that participates in the systemic response to inflammation. Its plasma concentration increases during inflammatory states, a characteristic that has long been employed for clinical purposes. Recent studies have demonstrated that intensive treatment like statin produced greater reductions in both LDL cholesterol and CRP, suggesting a relationship between these two biomarkers and CVD progression [Nissen et al. (2005) *N. Eng. J. Med.;* 352:29-38]. Indeed, several studies have demonstrated that increased CRP concentrations are predictive of vascular events even among those without hyperlipidemia. In fact, CRP monitoring, among other analyses, was recommended by Naghavi and colleagues review on vulnerable plaques [Naghavi et al. (2003) *Circulation;* 108:1664-72] as a key parameter. Accordingly, Rifai and Ridker have proposed an algorithm for cardiovascular risk prediction using both CRP and Total/HDL-Cholesterol ratio [Rifai and Ridker (2001) *Clin. Chem.;* 47:28-30]. In the present study the comparison of short-term consumption of control diet with or without fish oil or the omega-3 esters mixture of the invention (Preparation A) exhibited only a mild tendency towards altered effects (FIG. 24). However, in a paired analysis it was distinctly shown that CRP levels following the omega-3 esters mixture of the invention (Preparation A) treatment were significantly reduced, compared with control diet (P-value=0.058) and fish oil (P-value=0.042). Further correlations between the total to HDL-cholesterol ratio and CRP-levels had remarkably indicated a reduced relative risk of CVD event prospective in the following ten years for the subjects who consumed the omega-3 esters mixture of the invention (FIG. 25).

In parallel to the aforementioned suggestion that elevated plants sterol levels could serve as reinforcement to the superior bioavailability of fish oil attached to the plant sterols, it could play a role in a different biological process. The action of plant sterols as anticancer dietary components has been recently extensively reviewed [Awad et al. (2000) *J. Nutr.;* 130:2127-30]. Plant sterols can suppress tumor cell growth (LNCaP and HT-29) [Awad et al. (2000) *Nutr Cancer;* 36:74-8]. Compared to cholesterol, beta-sitosterol caused a 24% decrease in cell growth and a 4-fold increase in apoptosis. Finding in SCID mice xenografted with the human breast cancer cell line implied the possibility that plant sterols may retard the growth and spread of breast cancer cells [Awad et al. (2000) *Anticancer Res.;* 20:821-4]. In addition to retarding the growth of breast cancer cells by plant sterols, there is some evidence that plant sterols can affect the development of prostate cancer [Wilt et al. (2000) *Cochrane Database Syst* 2]. In a meta-analysis, 519 men were studied in 4 randomized, placebo-controlled, double-blind trials. Beta-sitosterol improved urinary symptom scores and flow measures, suggesting that non-glucosidic forms of beta-sitosterol improve urinary symptoms and flow measures.

In the present study there was indeed a mild tendency of prostate specific antigen (PSA) reduction (−5.2%) comparing to the control diet (0.22%). The low statistical significant could be attributed to the relative low levels of PSA detected in the subjects and the high variability.

TNF-α and IL-6

While the n-6 polyunsaturated fatty acid (PUFA), arachidonic acid (AA), is a precursor of prostaglandins, leukotrienes and related compounds that have important roles as mediators and regulators of inflammation, consuming increased amounts of long chain n-3 PUFA (found in oily fish and fish oils) results in a partial replacement of the AA in cell membranes by DHA and EPA. This leads to decreased production of AA-derived mediators. This alone is a potentially beneficial anti-inflammatory effect of n-3 fatty acids. Moreover, animal studies have provided a great deal of evidence that feeding plant or fish oils rich in n-3 PUFAs does alter the ex vivo production of tumor necrosis factor (TNF), interleukin 1 (IL-1), IL-6 and IL-2, but many contradictory observations have been made; it is most likely that the discrepancies in the literature result from differences in the cell types and experimental protocols used. Human studies provide more consistent data; several studies have shown that supplementation of the diet of healthy volunteers results in reduced ex vivo production of IL-1, IL-6, TNF and IL-2 by peripheral blood mononuclear cells [Calder (1997) *Ann Nutr Metab.;* 41(4):203-34]. Recently, studies conducted in obese [Jellema et al. (2004) *Eur J Clin Invest.;* 34(11):766-73] and diabetic patients [Mori et al. (2003) *Free Radic Biol Med.;* 35(7):772-81] administrating moderate to high dosage of purified EPA and/or DHA failed to demonstrate a comparable alterations in these subjects blood inflammation markers levels. In the present study it was shown that as expected, the control diet had no effect on TNF-α and IL-6 levels, while similar feeding period with fish oil resulted with augmented levels of these markers. However, the omega-3 esters mixture of the invention (Preparation A) treatment had generated the largest effect on these inflammation markers levels.

In a further aspect, the invention relates to unique dosage unit form, for the delivery of an effective dose, preferably the RDI (recommended daily intake), of both phytosterols and DHA/EPA.

Different active dietary ingredients, such as vitamins, have a recommended daily allowance (RDA), provided by different health authorities, such as the US Food and Drug Administration (FDA). The RDI of sterols, according to the US FDA is 0.8 g/day. This RDI is supposed to provide the cholesterol reduction effects attributed to phytosterols. The International Society for the Study of Fatty Acids and Lipids had recommended in April 1999 following the "Workshop on the essentiality of and recommended dietary intakes for omega-6 and omega-3 fatty acids" an adequate intake of 650 mg of EPA+DHA per day in connection to cardio-protective effects. Since both phytosterols and omega-3 fatty acids such as DHA and EPA are linked to heart health it may be desirable to create mixtures of these two ingredients. In order to create a homogenous blend of these two ingredients, the use of the oil-soluble phytosterol-esters is necessary. When attempting to prepare a mixture of commercial phytosterol-esters and EPA/DHA omega-3 fatty acids one may be required to consume high dosages per day, for example of up to 4-5 g of mixture.

The RDI of plant sterol esters is 1.4 g/day, correlated to 0.8 g/day of the free phytosterols. Relatively pure (90-95% wt) plant sterol esters are commercially available. The most common source of DHA and EPA is fish oils, of which the most popular are those containing about 25 g/100 g of EPA/DHA, usually in a ratio of 18:12. Thus, by using these two sources of phytosterols and EPA/DHA, in order to achieve the recommended levels described above, one would need to consume 4.2 g per day. This amount, provided in softgel capsules, taking into account the limitation of capsule size, may be divided to about 4-5 capsules. Such large number of capsules per day is tedious to the health-conscious end consumer. Even when using more concentrated fish oil, such as containing about 55% wt of EPA/DHA, one would still need to consume about 2.75 g of the mixture. This again results in 3 large capsules per day. However, market research has shown that consumers prefer to consume dietary supplements or pharmaceutical preparations by a maximum of 2 unit forms per day.

The present invention provides a solution to this problem by introducing a pharmaceutical dosage form of esters of LC-PUFA with phytosterols and/or phytostanols, wherein said RDI of sterols is from about 0.4 g to about 1.0 g, preferably from about 0.6 g to about 0.8 g. Said RDI of LC-PUFA, specifically DHA and EPA is from about 0.3 g to about 0.8 g, preferably from about 0.5 g to about 0.65 g.

Since in the omega-3 esters mixture of the invention, and particularly Preparation A, the Phytosterol Esters Fraction Also Contains EPA and DHA fatty acids, the mixture of the invention can deliver the RDIs mentioned above in a total amount of about 2 g per day. This amount can be easily delivered by two (2), user friendly, capsules per day. This mixture contains about 1.5-1.6 g of phytosterol esters, of which about 60% are esterified to EPA/DHA. Hence, the amount of phytosterol esters corresponds to the RDA 0.8 g/day of phytosterols and 420 to 480 mg of EPA/DHA. It is to be noted that phytosterol esters of LC-PUFAs weigh more than vegetable-oil derived fatty acids esterified to plant sterol, since LC-PUFAs are characterized by a higher molecular weight compared to vegetable-oil derived fatty acids, usually containing only 16-18 carbons. By mixing the above amount of LC-PUFA phytosterol esters with about 400 mg of LC-PUFA rich oil, such as fish oil, containing about 60% EPA/DHA, one can easily obtain 660-720 mg of EPA/DHA in the final mixture. Thus, this mixture contains both the recommended levels of omega-3 LC-PUFAs and phytosterols in a total amount of up to 2 g, easily provided by 2 capsules. It is to be further noted that the omega-3 mixture of the invention has omega-3 fatty acid moieties on both the phytosterol and the glyceridic fractions, thus being inherently capable of providing high quantities of phytosterol. This is a further advantage of the mixtures of the invention, particularly Preparation A.

Alternatively, the omega-3-esters mixtures may be the active ingredient of a pharmaceutical or nutraceutical composition for reducing blood levels of both cholesterol and triglycerides and/or for lowering circulating small-dense LDL particles. In particular, these compositions may be used for reducing blood levels of $HDL_3$ whilst elevating levels of $HDL_2$ lipid sub-fractions, and maintaining a high ratio of HDL/LDL. Thus, use of the mixtures and compositions of the invention may be advantageous in reducing the relative risk of coronary events, in both males and females. In addition, the mixtures and compositions of the invention may be useful in reducing risk of developing IHD, atherosclerosis and hypertension. A further important use is in the prevention and treatment of the metabolic syndrome (Syndrome X) and related conditions such as insulin resistance. Another use of the mixtures and compositions of the present invention is in the treatment of cancer.

In addition, pharmaceutical compositions comprising the PSE+DAG combination as the active or auxiliary ingredient may be used for reducing blood levels of both cholesterol and triglycerides and/or for lowering oxidation levels of serum, serum LDL and macrophage oxidation, inhibiting the formation of foam cells and/or preventing the deleterious effects generated by lipid-induced oxidative stress.

The dosage of the PSE+DAG combination of the invention may depend upon the condition to be treated, the patient's age, sex and bodyweight, and will be determined by the attending physician or dietician. A preferred dosage for an adult may be from about 1.5 to about 6 g of PSE+DAG in oil dispersion (in accordance with the invention) per day, preferably 2-5 g, which shall comprise approximately 1300 mg of PSEs and up to 800 mg of DAGs.

Other formulations which may be in unit dosage forms may be as follows:

A combination of PSE and DAG dissolved in canola oil where the fatty acids of the sterol esters and the DAG resemble the fatty acid profile of canola oil, comprising including 31.5% wt PSE and 10% wt DAG. Each 4.5 g of this combination will contain at least 1300-1400 mg PSE (RDA) and 450 mg of DAG.

A combination of PSE and DAG dissolved in soybean oil, where the fatty acids of the sterol esters and the DAG resemble the fatty acid profile of soybean oil, comprising 31% wt PSE and 15.9% wt DAG. Each 4.5 g of this formulation will contain at least 1300-1400 mg PSE (RDA) and 700 mg of DAG.

A combination of PSE and DAG dissolved in canola oil comprising 61% wt PSE and 10% wt DAG. Each 2 g will contain at least 1300-1400 mg PSE (RDA) and 200 mg of DAG.

A combination of PSE and DAG dissolved in fish oil where the fatty acids of the sterol esters and the DAG resemble the fatty acid profile of fish oil, comprising 61% wt PSE and 8.3% wt DAG. Each 2 g will contain at least 1300-1400 mg PSE (RDA) and 150 mg of DAG.

A combination of PSE and DAG dissolved in canola oil where the fatty acids of the sterol esters and the DAG resemble the fatty acid profile of canola oil, comprising 23% wt PSE and 8% wt DAG. Each 6 g will contain at least 1300-1400 mg PSE (RDA) and 450 mg of DAG.

Other PSE and DAG formulations as well as dilutions of all formulations are within the scope of the invention.

The preparation of pharmaceutical compositions is well known in the art, see e.g., U.S. Pat. Nos. 5,736,519, 5,733,877, 5,554,378, 5,439,688, 5,418,219, 5,354,900, 5,298,246, 5,164,372, 4,900,549, 4,755,383, 4,639,435, 4,457,917, and 4,064,236. The omega-3-esters mixture used by the present invention may be preferably mixed with an additive, excipient, carrier and/or diluent, and optionally, a preservative or the like pharmacologically acceptable vehicles as known in the art, see e.g., the above US patents. Examples of excipients include glucose, mannitol, inositol, sucrose, lactose, fructose, starch, corn starch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like.

The pharmaceutical composition is preferably provided in liquid, solid or semi-solid form. The liquid preparation is provided preferably as an oil suspension or microcapsule composition. A semi-solid composition is provided preferably as oily gel or cream.

Tablets, hard tablets, caplets, capsules and particularly soft gelatin capsules, containing the omega-3-esters mixture of the invention may be preferred, either as dietary supplements or as pharmaceutical dosage forms. In essence, any pharmaceutical dosage form suitable for oral administration may be used for delivering the combination of the invention.

The dosage of the active mixtures of the invention may depend upon the condition to be treated, the patient's age, sex and bodyweight, and shall be determined by the attending physician or dietician. A preferred dosage for an adult may be from about 2 to about 6 g of omega-3 mixtures per day, e.g. 4 to about 6 g of Preparation A per day, preferably 5 g, which comprise approximately 1300 mg of PSEs and 800 mg of diglyceridic esters of LC-PUFA, preferably of DHA/EPA.

As described above, the present invention also provides mixtures which are highly concentrated, and can deliver high doses of phytosterol and of DHA/EPA in dosage unit forms. Evidently when using the concentrated forms, lower doses may be used, depending mainly on the amount of phytosterol esters.

The omega-3 mixtures, or the PSE+DAG combination or composition of the invention may be used per se, as a food article. Such food article may be any conventional food, and also a functional food or beverage. Alternatively, they may be an ingredient of a food article or supplement, which may further optionally contain conventional additives used in the food industry, such as preserving agents, colorants, flavoring agents, fragrances, antioxidative and hardening agents, vitamins, calcium, other minerals, trace elements, probiotic agents, isoflavones, caloric agents and the like.

In addition, the food supplements of the invention may be used in the manufacture of any one of functional foods, functional drinks or dietary supplements. Said food supplement may be introduced into said food, drink or dietary supplement by admixing, adding or incorporating it during manufacture thereof.

The terms dietary nutrient and food supplement may be used herein exchangeably, and are to be taken to mean any edible supplements, particularly dietary supplements to edible products, preferably food articles, including functional foods and functional beverages.

As mentioned above, the mixtures and compositions of the invention may be useful in reducing the risk of developing IHD, atherosclerosis and hypertension, as well as in the prevention and treatment of the metabolic syndrome (Syndrome X) and related conditions such as insulin resistance, and in the treatment of cancer. Thus, the present invention also refers to a method of treating and/or preventing any of the above conditions, by orally administering a therapeutically effective dosage of the active mixtures, food supplement or compositions of the invention to a subject in need. Consequently, the method is also effective for the treatment of cardiovascular disorders, coronary heart disease, atherosclerosis, as well as cardiovascular disorders induced or manifested by other diseases such as diabetes mellitus, particularly Type II diabetes.

The present invention is particularly directed at a method of treating and/or preventing conditions related to any one of high cholesterol and triglycerides blood levels, serum oxidative stress, ox-LDL uptake by macrophages, macrophage oxidative status, foam cells formation and lipid-induced oxidative stress, said method consisting of orally administering a therapeutically effective dosage of the combination or composition of the invention, in the form of a food supplement, nutraceutical or pharmaceutical composition to a subject in need. Consequently, the method is also effective for the treatment of cardiovascular disorders, coronary heart disease, atherosclerosis, as well as cardiovascular disorders induced or manifested by other diseases such as diabetes mellitus, particularly Type II diabetes.

Alternatively, such conditions are to be prevented by consumption of the dietary products in accordance with the invention.

Lastly, the present invention presents a method for improving health, consisting of administering a therapeutically effective dosage of the dietary nutrient comprising the omega-3-esters mixture of the invention, or the pharmaceutical or nutraceutical composition thereof to a subject in need.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Materials

Olive oil: commercial extra virgin olive oil, manufactured by Meshek Eger (Yokeneam HaMoshava, Israel).
Canola oil: commercial canola oil, manufactured by Shemen Taasiot (Haifa, Israel).
Fish oil: commercial fish oil, manufactured by Pronova (Lysaker, Norway).

TABLE 1

Composition of the PSE + DAG oils

| Oil components % (w/w) | PSE + DAG in Canola oil | PSE + DAG in Olive oil (Enzymotec FG S7/1.75) | PSE + DAG in Fish oil | Olive oil enriched with phytosterol esters |
|---|---|---|---|---|
| Phytosterol esters | 26 | 28.5 | 22.12 | 18 |
| Monoglycerides | 2.1 | 1.48 | 4.72 | 0.31 |
| Diglycerides | 14.9 | 14.62 | 20.02 | 0.81 |
| Triglycerides | 46.9 | 48.9 | 40.3 | |
| Free sterols | 3.1 | 1.5 | 5.2 | 0.2 |
| FFA | 7 | 5 | 5 | 3 |
| Glycerol | N.D. | N.D. | 2.6 | N.D. |
| Brassicasterol* | 0.54 | 0.46 | 0.82 | N.D. |
| Campasterol* | 5.43 | 4.58 | 4.93 | 0.009 |
| Stigmasterol* | 2.84 | 3.86 | 3.25 | 0.00142 |
| Betasitosterol* | 8.9 | 8.41 | 8.1 | 0.166 |

*levels of the different sterols, which can be either esterified or non-esterified.

All materials were protected from light and odorous products at a temperature not exceeding 25° C.

Tri- and di-glyceride Esters of Omega-3 LC-PUFAs (Fish Oil)

The following Tables 2A, 2B and 2C give the fatty acid and glycerides composition of the commercial fish oil used in the LC-PUFA control groups in the Examples 1-3 presented below.

TABLE 2A

| Fatty acid composition summary (%) | |
|---|---|
| DHA | 51.1 |
| EPA | 23.3 |
| Omega-3 | 81.6 |
| Oleic acid | 3.8 |

TABLE 2B

| Fatty Acid Composition (mg/g) | |
|---|---|
| C14 | 2.8 |
| C15 | 0.3 |
| C16 | 6.1 |
| C16:1 | 3.8 |
| C17 | 0.7 |
| C18 | 1.7 |
| C18:1 | 36.4 |
| C18:2 | 5.8 |
| C18:3n3 | 6.3 |
| C18:4 | 13.3 |
| C20 | 0.4 |
| C20:1 | 25.1 |
| C20:2 | 4.5 |

TABLE 2B-continued

| Fatty Acid Composition (mg/g) | |
|---|---|
| C20:4n6 | 10.4 |
| C20:4n3 | 15.5 |
| C20:5n3 | 220.7 |
| C22 | 0.3 |
| C22:1 | 6.5 |
| C22:5n3 | 47.4 |
| C22:6n3 | 484.1 |
| C24 | |
| C24:1 | 2.8 |
| Others | 53.3 |

TABLE 2C

| Glyceride composition | |
|---|---|
| Monoglycerides, % w/w | 2.52 |
| Digylcerides, % w/w | 28.36 |
| Ratio 1,3/1,2 diglycerides | 2.9 |

Phytosterol, tri, di- and monoglyceride esters of Omega-3 LC-PUFAs

The following Tables 3A to 3F give the composition of the omega 3-phytosterol esters mixture (composition of the invention) used in Example 4 presented below. This preparation is referred to herein as Preparation A.

TABLE 3A

| Total Fatty acid composition summary (%) | |
|---|---|
| DHA | 50.3 |
| EPA | 23.9 |
| Omega 3 | 81.6 |
| Oleic acid | 3.9 |

TABLE 3B

| Total fatty Acid Composition (mg/g) | |
|---|---|
| C14 | 2.0 |
| C15 | 0.2 |
| C16 | 4.5 |
| C16:1 | 2.9 |
| C17 | 0.5 |
| C18 | 2.0 |

TABLE 3B-continued

| Total fatty Acid Composition (mg/g) | |
|---|---|
| C18:1 | 29.7 |
| C18:2 | 4.6 |
| C18:3n3 | 4.7 |
| C18:4 | 10.6 |
| C20 | 0.5 |
| C20:1 | 18.7 |
| C20:2 | 3.3 |
| C20:4n6 | 8.9 |
| C20:4n3 | 12.1 |
| C20:5n3 | 180.9 |
| C22 | 0.2 |
| C22:1 | 6.5 |
| C22:5n3 | 39.0 |
| C22:6n3 | 381.8 |
| C24 | |
| C24:1 | 2.3 |
| Others | 42.4 |

TABLE 3C

| Total Sterols, % w/w | |
|---|---|
| Brassicasterol | 0.821 |
| Campesterol | 4.93 |
| Stigmasterol | 3.25 |
| Beta-sitosterol | 8.1 |
| Others | 1.11 |
| Total | 18.211 |
| Free phytosterol, % w/w | 5.2 |
| Phytosterol esters % w/w | 22.12 |

Values calculated according to average MW of sterols and FA

TABLE 3D

| Glycerides composition | |
|---|---|
| Monoglycerides, % w/w | 4.73 |
| Digylcerides, % w/w | 20.02 |
| Ratio 1,3/1,2 diglycerides | 3.5 |

TABLE 3E

| Fatty Acid composition of PE (%) | |
|---|---|
| DHA | 49.0 |
| EPA | 14.8 |
| Omega 3 | 72.3 |
| Oleic acid | 7.5 |
| Total unsaturated | 91.0 |
| Total saturated | 2.4 |

TABLE 3F

| Fatty Acid Composition of Phytosterol esters, mg/g phytosterol esters: | |
|---|---|
| C14 | 1.7 |
| C15 | 0.2 |
| C16 | 4.1 |
| C16:1 | 2.6 |
| C17 | 0.6 |
| C18 | 2.0 |
| C18:1 | 28.6 |
| C18:2 | 4.6 |
| C18:3n3 | 5.1 |
| C18:4 | 15.0 |
| C20 | 0.4 |
| C20:1 | 11.8 |

TABLE 3F-continued

| Fatty Acid Composition of Phytosterol esters, mg/g phytosterol esters: | |
|---|---|
| C20:2 | 2.3 |
| C20:4n6 | 2.6 |
| C20:4n3 | 9.7 |
| C20:5n3 | 56.1 |
| C22 | |
| C22:1 | 2.6 |
| C22:5n3 | 17.5 |
| C22:6n3 | 186.5 |
| C24 | |
| C24:1 | 0.9 |
| others | 25.4 |

Chemical Preparation of Omega-3 Esters Mixture of Glycerides and Sterols 900 g of fish oil (EPAX 20:50, Pronova) and 200 g of soybean phytosterols (ChoLevel, Fenchem) were mixed together and dried by heating to 110° C. under vacuum. 3.7 g of sodium methoxide were added after pressure was carefully brought to atmospheric by nitrogen addition and temperature was reduced to 100° C. After addition of sodium methoxide, vacuum conditions were restored. Reaction was followed by measuring the content of free phytosterols. When free phytosterol level dropped below 2% w/w, the reaction was stopped by the addition of 4% citric acid solution (50% concentration). Water was removed under the reaction condition and the resulting mixture is filtered. Filtered oil mixture is further bleached to remove soap residues and the bleached product is molecular distilled (170° C., 0.01 mbar), cooled and the product (residue) is supplemented with antioxidants.

The composition of the chemically produced preparation is summarized in Table 4.

TABLE 4

| | | |
|---|---|---|
| Monoglycerides, % w/w | | 1.3 |
| Diglycerides, % w/w | | 17.5 |
| Ratio 1,3/1,2 diglycerides | | 3.5 |
| Sterols, mg/g: | | |
| | campesterol | 46.8 |
| | stigmasterol | 38.9 |
| | β-sitosterol | 84.4 |
| | others | 9.1 |
| Total sterols % w/w | | 17.9 |
| Free phytosterols | | 1.7 |
| Phytosterol esters | | 28.4 |
| Sodium, ppm | | 3.1 |

Preparation of Omega-3 Esters Mixture of Glycerides and Sterols (Concentrated)

500 g of fish oil ethyl esters (EE 20:50, ONC) and 500 g of soybean phytosterols (ChoLevel, Fenchem, Nanjing, China) were mixed together and dried by heating to 110° C. under vacuum. 5 g of sodium methoxide were added after pressure was carefully brought to atmospheric by nitrogen addition and the temperature was reduced to 100° C. After catalyst addition, vacuum conditions were restored. Reaction was followed by measuring the content of free phytosterols. When the free phytosterol level dropped below 4% w/w the reaction was stopped by the addition of 4% water. Water is further removed by centrifugation and the resulting sterol esters are treated with silica (Trysil) and filtered. The filtered esters are further bleached to remove soap residues and the bleached product is steam deodorized (200° C., 1 hr) cooled and supplemented with antioxidants. The sodium is measured in final product and is below 5 ppm. 810 gr of the obtained deodorized phytosterol esters are added to 190 g of fish oil (TG 48:25, ONC), to give fish oil enriched with phytosterol esters. The composition of the final mixture is summarized in Table 5.

TABLE 5

| | |
|---|---|
| Diglycerides, % w/w | 6.7 |
| Monoglycerides, % w/w | 0.7 |
| Sterols, mg/g: | |
| Brassicasterol | 1.44 |
| Campesterol | 111.76 |
| Stigmasterol | 90.66 |
| β-sitosterol | 185.31 |
| Others | 11.01 |
| Total Phytosterols, % w/w | 40.2 |
| Free phytosterols, % w/w | 3.5 |
| Phytosterol esters, % w/w | 64 |
| Fatty Acid Compostion, mg/g: | |
| C14 | 1.19 |
| C16 | 4.00 |
| C16:1 | 1.75 |
| C18 | 4.26 |
| C18:1 | 10.23 |
| C18:2 | 1.49 |
| C18:3n3 | 0.73 |
| C18:4n3 | 1.55 |
| C20 | 2.97 |
| C20:1 | 17.25 |
| C20:2 | 2.00 |
| C20:4n6 | 7.01 |
| C20:4n3 | 9.28 |
| C20:5n3 | 143.85 |
| C22 | 1.39 |
| C22:1 | 15.01 |
| C22:5n3 | 33.78 |
| C22:6n3 | 204.41 |
| C24:1 | 7.00 |
| Others | 38.10 |

Methods

Animal Studies

Free Radical Scavenging Capacity

The free radical-scavenging capacity of olive oil, olive oil+phytosterols, and PSE+DAG in olive oil was analyzed by the DPPH assay. DPPH (1,1-diphenyl-2-picryl-hydrazyl) is a radical-generating substance that is widely used to monitor the free radical scavenging abilities (the ability of a compound to donate an electron) of various anti-oxidants [Belinky, P. A. et al. (1998) *Free Radic. Biol. Med.* 24: 1419-29]. The DPPH radical has a deep violet color due to its impaired electron, and radical scavenging can be followed spectrophotometrically by the loss of absorbance at 517 nm, as the pale yellow non-radical form is produced. 15 μl from stock solution of each sample were mixed with 1 mL of 0.1 mmol DPPH/L in ethanol and the change in optical density at 517 nm was continuously monitored.

Isolation of Mouse Peritoneal Macrophages

Mouse peritoneal macrophages (MPM) were harvested from the peritoneal fluid of the E° mice (15-25 g) 4 days after intraperitoneal injection of thioglycolate (24 g/L) in saline (3 mL). Cells (10-20×10$^6$/mouse) were washed 3 times with PBS and re-suspended to 10$^6$/mL in DMEM containing 5% fetal calf serum (heat-inactivated at 56° C. for 30 min), 100 U penicillin/mL, 100 μg streptomycin/mL, and 2 mM glutamine. The cell suspension was plated into culture dishes and incubated in a humidified incubator (5% $CO_2$, 95% air) for 2 hours. The dishes were washed once with DMEM to remove non-adherent cells, and monolayers were incubated under similar conditions for 18 hours. Mouse peritoneal macrophages were isolated from 6 mice from each group, pooled and analyzed in duplicate or triplicate for each assay.

Macrophage Superoxide Release

The production of superoxide anion ($O_2^-$) by mouse peritoneal macrophages was measured as the superoxide dismutase-inhibitable reduction of cytochrome C [Yanagitani Y. et al. (1999) *Hypertension* 33:335-9]. Cells (1×10$^6$/well) were incubated in 1 mL of HBSS containing acetyl cytochrome C (80 μmol/L). Superoxide production by the cells was stimulated by the addition of phorbol myristate acetate (PMA; 0.5 μg/mL) for 1 hour. To some control samples, superoxide dismutase (SOD, 30 mg/L) was added. The amount of superoxide release was determined in the medium and was expressed as nmoles of superoxides/mg cell protein, using an extinction coefficient of $E_{550}$=21 mmol/L$^{-1}$ cm$^{-1}$.

Macrophage Peroxide Content

Cellular peroxide levels were determined by flow cytometry using Dichlorofluorescin-diacetate (DCFH-DA) [Goupy, P. et al. (2003) *Fr. Journal of Agricultural and Food Chemistry* 51(3):615-622]. DCFH-DA is a non-polar dye that diffuses into the cells. In the cells it is hydrolyzed into the nonfluorescent derivate 2',7'-DCFH, which is polar and trapped within the cells. Under oxidative stress, DCFH is oxidized to DCF (2',7'-dichlorofluorescein), which is a fluorescent compound. Peritoneal macrophages (2×10$^6$) were incubated with 2.5×10$^{-5}$ mol/L DCFH-DA for 30 minutes at 37° C. Reaction was stopped by washes with PBS at 4° C. Cellular fluorescence was determined with a flow cytometry apparatus (FACS-SCAN, Becton Dickinson, San Jose, Calif., USA). Measurements were done at 510 to 540 nm after excitation of cells at 488 nm with an argon ion laser.

Serum Lipids Profile

Serum samples were analyzed for their lipid profile including total cholesterol and triglycerides, by using commercially available kits (Roche Diagnostics, Penzberg, Germany).

Serum Lipids Peroxidation

Serum was diluted 1:4 in PBS. Serum susceptibility to oxidation was determined by incubating serum sample with 100 mM of the free radical generating compound, 2'-2'-azobis 2'-amidinopropane hydrochloride (AAPH), which is an aqueous soluble azo compound that thermally decomposes to produce peroxyl radicals at a constant rate. The formation of thiobarbituric reactive substances (TBARS) and of lipid peroxides was measured and compared to serum that was incubated under similar conditions, but without AAPH.

PON1 Activity Measurements

PON 1 activity in serum was determined by measuring arylesterase activity, using phenylacetate as the substrate. Initial rates of hydrolysis were determined spectrophotometrically at 270 nm. The assay mixture included 1.0 mM phenylacetate and 0.9 mM $CaCl_2$ in 20 mM Tris HCl, pH 8.0. Non-enzymatic hydrolysis of phenylacetate was subtracted from the total rate of hydrolysis. The $E_{270}$ for the reaction was 1,310 M$^{-1}$ cm$^{-1}$. One unit of arylesterase activity is equal to 1 μmol of phenylacetate hydrolyzed/min/ml. Purified enzyme has nearly 2000 units of arylesterase activity per mg protein.

Macrophage Oxidative Status

Cellular oxidative stress was examined in DCF-loaded macrophages by flow-cytometry using the conversion of non-fluorescent DCFH-DA to its fluorescent counterpart DCF as an index.

Macrophage-Mediated Oxidation of LDL

MPM were incubated with LDL (100 μg of protein/mL) for 18 hours, under oxidative stress (in the presence of 2 μmol/L of $CuSO_4$), after which the extent of LDL oxidation was determined by the TBARS assay.

Macrophage Uptake of Oxidized LDL

MPM were incubated with $^{125}$I-labeled oxidized LDL (10 μg of protein/ml), and lipoprotein cell-association and degradation by these cells was determined. Lipoprotein cellular degradation was measured in the collected medium as the trichloroacetic acid (TCA)-soluble, non-lipid radioactivity, which was not due to free iodide. Lipoprotein degradation in a cell-free system was measured under identical conditions, and was subtracted from the total degradation. The remaining cells were washed three times with cold PBS and dissolved in 0.1 N NaOH for protein and cell-associated lipoproteins determination.

Statistical Analyses

Student t-test was used for statistical analysis of the results.

Human Studies

These studies were designed as a randomized, single-blind, cross-over clinical intervention trial. These experiments involved testing the effects of dietary matrices containing specific fatty acid and/or plant sterol mixtures included in normal diets, compared to non-supplemented diets, on circulating lipid levels, in moderately overweight subjects with elevated serum lipid levels for whom dietary modification is the primary and at times only therapeutic recommendation.

Patients

Twenty-four (24) volunteers (11 male, 13 female, age 30-65 yr) with LDL-cholesterol concentrations >130 mg/dL were recruited for this study. Body mass indices (BMI) of subjects ranged from 23-32 $kg/m^2$, except for three subjects in which BMI was between 21.4 and 23 $kg/m^2$. Twenty-one volunteers completed the study (11 male, 10 female).

Diets

All volunteers underwent a feeding trial according to a semi-randomized Latin square cross-over design containing three dietary phases, each four week in duration. The control diet was provided first, then the other phases randomized. Each feeding period was separated by a 4-week washout interval, during which volunteers consumed their typical diets without restriction. The composition of the diets was similar with respect to the food and nutrient content. The basic diet contained 30% of energy as fat (see control diet), 80 mg cholesterol/1000 kcal, 12 g fiber/1000 kcal, 15% energy as protein and 55% as carbohydrates. The variable component was the treatment oil. Diets were designated as:

Control group: baseline plant sterol level of about 200 mg/day, where the dietary fat was comprised at 70% energy as oleic acid-enriched vegetable oil.

PSE+DAG group: 1.7 g/day soy sterols esterified to olive oil fatty acids (predominantly oleic acid), contained in a diglyceride (DAG) and triglyceride containing olive oil (total amount=9 g/d).

LC-PUFA group: 7.6 g/day of fish oil providing the same amount of EPA and DHA as the plant sterol-fish oil ester diet.

Omega-3-esters mixture group: 1.7 g/day soy sterols esterified to fish oil fatty acids (including EPA and DHA), contained in a diglyceride and triglyceride containing fish oil (total amount=9 g/d)

All meals were equicaloric and breakfast was consumed each day under supervision. The treatment oil was given within the breakfasts consumed every day at the clinic under supervision. Volunteers were instructed to eat and drink only materials given to them by the Clinical Nutrition Research Unit (McGill University, Montreal, Canada), except for water. Study volunteers were encouraged to maintain their usual level of physical activity. Energy requirements were estimated using the Mifflin equation and multiplied by an activity factor of 1.7%. Energy intakes were adjusted over the initial 2-week period to maintain constant body weight and kept constant for the remaining 4 weeks and the other treatment phases.

Blood Lipid Analyses

On days 1, 2, 28 and 29, blood samples were obtained in the fasting state. On day 28, subjects reported at the clinic 4 hours after they consumed their normal experimental breakfast so that a blood sample was obtained in the postprandial state. Plasma was immediately separated and stored at −80° C. until analysis. The general lipid profile (Total, HDL and LDL cholesterol as well as triglycerides) was measured in samples taken on days 1, 2, 28 and 29 of each phase. Plasma total cholesterol and triglyceride in plasma, and HDL sub-fractions were determined by automated methods in duplicate on an Abbott Spectrum CCX Analyzer (Abbott, Dallas, Tex.) utilizing enzymatic reagents (Abbott A-GENT). LDL cholesterol was calculated by the Friedewald equation. If triglycerides were higher than 400 mg/dL, then LDL cholesterol levels were directly measured in plasma samples (N-geneous LDL-C assay, Equal Diagnostics), using a method in which LDL precipitated by the dextran/magnesium sulfate method in order to separate them from HDL. Apolipoproteins A and B100 were measured by nephelometry in samples from days 1, 2, 28 and 29. Lipoprotein (a) was measured by nephelometry in samples from days 1 and 28.

Plasma thiobarbituric acid reactive substances (TBARS) content, as a marker of its susceptibility to oxidative stress was determined using a commercial kit (TBARS assay kit, OXI-tek).

Plasma leptin levels were determined at beginning and end of each phase using a radioimmunoassay. TNF-alpha and IL-6 levels determined using a radioimmunoassay with monoclonal antibodies. Plasmenogen Activator Inhibitor-1 (PAI-1) and fibrinogen analysis is carried out by two stage enzymatic assay and with use of a Behring BN-100 nephelometer. Levels of C-reactive protein (CRP) were assessed using a sensitive immunoassay with monoclonal antibodies coated to polystyrene beads. Prostate specific antigen (PSA) levels were determined using a radioimmunoassay. Plant sterol levels of plasma and red cells were determined by gas liquid chromatography. Fatty acids profiles of plasma triglycerides were assessed using gas liquid chromatography (GLC). Fat soluble vitamin levels were determined by high performance chromatography (HPLC).

Example 1

Antioxidative Effect of Olive Oil, Olive Oil+Phytosterols and PSE+DAG in Olive Oil Against Macrophage Lipid Peroxidation in E° Mice As mentioned above, oxidative stress is involved in the pathogenesis of atherosclerosis. Atherosclerosis is associated with lipids peroxidation of plasma LDL and in arterial cells, including macrophages [Aviram M. (2000) *Free. Radic. Res.* 33:S85-97]. Under oxidative stress, macrophage peroxide levels become increased, and macrophages generate reactive oxygen species, leading to their increased atherogenicity [Aviram M. (2000) id ibid].

The apolipoprotein E deficient (E°) mice are widely used as an animal model for atherosclerosis as they develop severe hypercholesterolemia and atherosclerotic lesions on a chow diet. Moreover, in E° mice, accelerated atherosclerosis is associated with increased lipid peroxidation of plasma lipoproteins and arterial cells [Keidar S. (1998) *Life Sci.* 63:1-11].

Angiotensin II (Ang-II), a vasoconstrictor produced by the renin-angiotensin system, has been implicated in atherosclerosis. Ang-II activates macrophage NAD(P)H-oxidases, leading to increased macrophage lipid peroxidation [Rajagopalan S. et al. (1996) *J. Clin. Invest.* 97:1916-1923; Johnston R. B. Jr. (1984) *Methods Enzymol.* 105:365-9].

In the present Example, the anti-oxidative effect of three preparations of olive oil, designated olive oil+phytosterols, PSE+DAG in olive oil and olive oil, against macrophage oxidative stress was analyzed.

The following oil samples were tested (all diluted in water 1/2 v/v, stock solution):
1. Olive oil+phytosterols
2. PSE+DAG in olive oil
3. Olive oil The antioxidative effect against macrophage oxidative stress of the PSE+DAG in olive oil in comparison to olive oil+phytosterols and olive oil alone was analyzed by two parameters: (i) the ability to decrease macrophage peroxide content; and (ii) macrophage ability to release superoxide ions.

Mouse peritoneal macrophages were incubated with 50 μl of stock solution/ml of either olive oil+phytosterols, PSE+DAG in olive oil and olive oil alone for 15 min, followed by a further incubation for 1 hour with Angiotensin II ($10^{-7}$ M) to induce oxidative stress. Control cells were incubated with Angiotensin II alone. Macrophages were then analyzed for their peroxides content using the DCFH assay and for their ability to release superoxide ions (FIG. 2A, B).

1) Effect of Olive Oil, Olive Oil+Phytosterols, and PSE+DAG in Olive Oil on Macrophage Peroxide Content Pre-incubation of the macrophages with both olive oil+phytosterols and PSE+DAG in olive oil but not with olive oil alone reduced the macrophage peroxide content compared to control macrophages incubated with Angiotensin II alone. The macrophage lipid peroxides content, using the DCFH assay, is assessed by two parameters; first, the mean fluorescence intensity emitted by DCF and second, the percentage of cells that are positive for fluorescence emission. Preincubation of macrophages with 50 μl/ml of olive oil+phytosterols or PSE+DAG in olive oil led to a reduction of 83% and 64% in macrophage mean fluorescence intensity compared to control cells, whereas olive oil at the same concentration had no effect on the macrophage mean fluorescence intensity compared to control cells (FIG. 2A). Similarly, preincubation of macrophages with 50 μl/ml of olive oil+Phytosterols or PSE+DAG in olive oil led to a reduction of 74% and 55% in percentage of positive cells for fluorescence compared to control cells, whereas olive oil at the same concentration had no effect on the percentage of positive cells for fluorescence compared to control cells (FIG. 2B).

2) Effect of Olive Oil, Olive Oil+Phytosterols and PSE+DAG in Olive Oil on Macrophages Superoxides Ions Release Mouse peritoneal macrophages isolated from $E^0$ mice were pre-incubated with 50 μl/ml of either PSE+DAG in olive oil, olive oil+phytosterols or olive oil alone for 15 minutes followed by a further incubation for 1 hour with Angiotensin II ($10^{-7}$ M) to induce oxidative stress. Control cells were incubated with Angiotensin II alone.

All three olive oils preparations analyzed in the present study inhibited to some extent, macrophage superoxide release induced by Angiotensin II. However, PSE+DAG in olive oil and olive oil+phytosterols were significantly more potent than olive oil alone. Pre-incubation of macrophages with 50 μl/ml of PSE+DAG in olive oil, olive oil+phytosterols or olive oil alone led to a reduction of 29%, 23% and only 9% respectively in macrophage superoxides anions release, compared to control cells incubated with Angiotensin II alone (FIG. 3).

Olive oil preparations enriched with phytosterols, in particular PSE+DAG in olive oil, exhibited significant anti-oxidative properties against macrophage lipid peroxidation. In contrast, whereas olive oil alone did not exhibit any effect. Most importantly, the PSE+DAG in olive oil composition was more potent than the olive oil+phytosterols preparation in its ability to reduce macrophage peroxide content and macrophage superoxide release.

These results suggest that olive oil and the additional components (phytosterols and diglycerides) can bind and internalize into the macrophages. In addition, olive oil enrichment with phytosterols enables the preparation of the invention to inhibit cellular oxidative systems (such as the NADPH oxidase and/or lypoxygenases) or to activate cellular anti-oxidant systems (such as the glutathione or superoxide dismutase systems). Furthermore, the addition of DAG to the olive oil+phytosterol preparation (resulting in the PSE+DAG in olive oil, in accordance with the invention) led to an additional antioxidative effect towards macrophage lipid peroxidation. The inventors thus speculate that DAG, which participates in numerous intracellular signal transduction pathways, could further affect the above cellular oxidative/antioxidative systems which are involved in Angiotensin II-mediated cellular oxidative stress, expressed as macrophage lipid peroxidation and superoxide release.

Example 2

The effect of PSE+DAG in canola oil and PSE+DAG in fish oil on the atherogenicity of lipoproteins and macrophages, and on atherosclerosis development in the atherosclerotic apolipoprotein E deficient ($E^0$) mice model was investigated. Apolipoprotein E deficient) (apoE°) mice at 8 weeks of age were assigned randomly to the following groups (5 mice each) as described below. The mice received regular chow diet, and in addition, they were fed (via gavage) the following, once every three days:

Group I:
1. Placebo group: did not receive any addition of oil.
2. Canola oil group (control): were fed with 60 μl of canola oil.
3. PSE+DAG in canola oil group: were fed with 60 μl of PSE+DAG in canola oil.

Group II:
1. Placebo group: did not receive any addition of oil.
2. PSE+DAG in fish oil: were fed with 60 μl of PSE+DAG in fish oil.

Each mouse consumed approximately 5 mL of water/day, and 5 g of chow/day.

Oil Preparation for Feeding

The amounts of PSE+DAG in canola oil and PSE+DAG in fish oil fed to the mice were based on the following:

The recommended phytosterols dosage for humans is 1.5 gr of phytosterols/day. Based on 18.1% phytosterols in each sample, the dosage for PSE+DAG in canola oil and PSE+DAG in fish oil for humans is therefore 1.5/0.18=8.33 gr/day/person. For mice, the body weight should be taken into consideration (60,000 gr human body weight/20 gr mouse body weight=3000), thus the daily dosage for mouse is 8.33 gr/3000=2.78 mg/day/mouse, which is equal to 2.78/0.93=2.99 mL/day/mouse. Since the experiment was done for a limited period, the dosage used was 5-fold higher. Thus, each mouse was administered 15 mL of oil/day (60 mL/4 days/mouse).

At the end of the experimental period, blood samples were collected from all mice for serum separation and analyses. Within each experimental group, the blood sample of each mouse was analyzed individually. The following parameters were analyzed in the serum:
1. Determination of lipids, including total cholesterol and triglycerides levels.
2. Determination of serum oxidative status.
3. Determination of paraoxonase, measured as arylesterase activity.

MPM were harvested prior to removal of the heart and aorta. The mice were anesthetized with ethyl ether in a local nasal container.

The experimental protocol (No. IL-066-10-2001) was approved by the Animal. Care and Use Committee of the Technion Israel Institute of Technology (Haifa, Israel).

FIG. 3 shows that the consumption of PSE+DAG in canola oil resulted in a remarkable and significant reduction in the levels of triglycerides in the serum (36%), in comparison with placebo ($p<0.001$).

Figure 4:
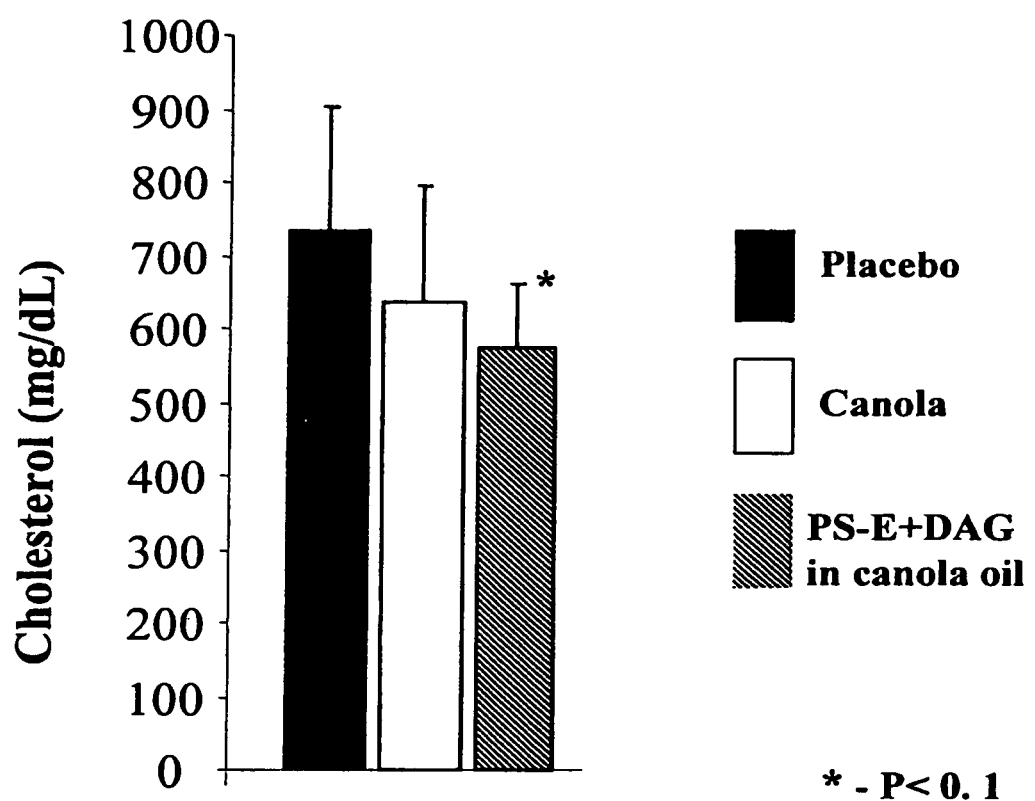

Similarly, FIG. 4 shows that particularly PSE+DAG in canola oil demonstrated a tendency to reduce total cholesterol levels in the serum ($p<0.1$).

Figure 5:
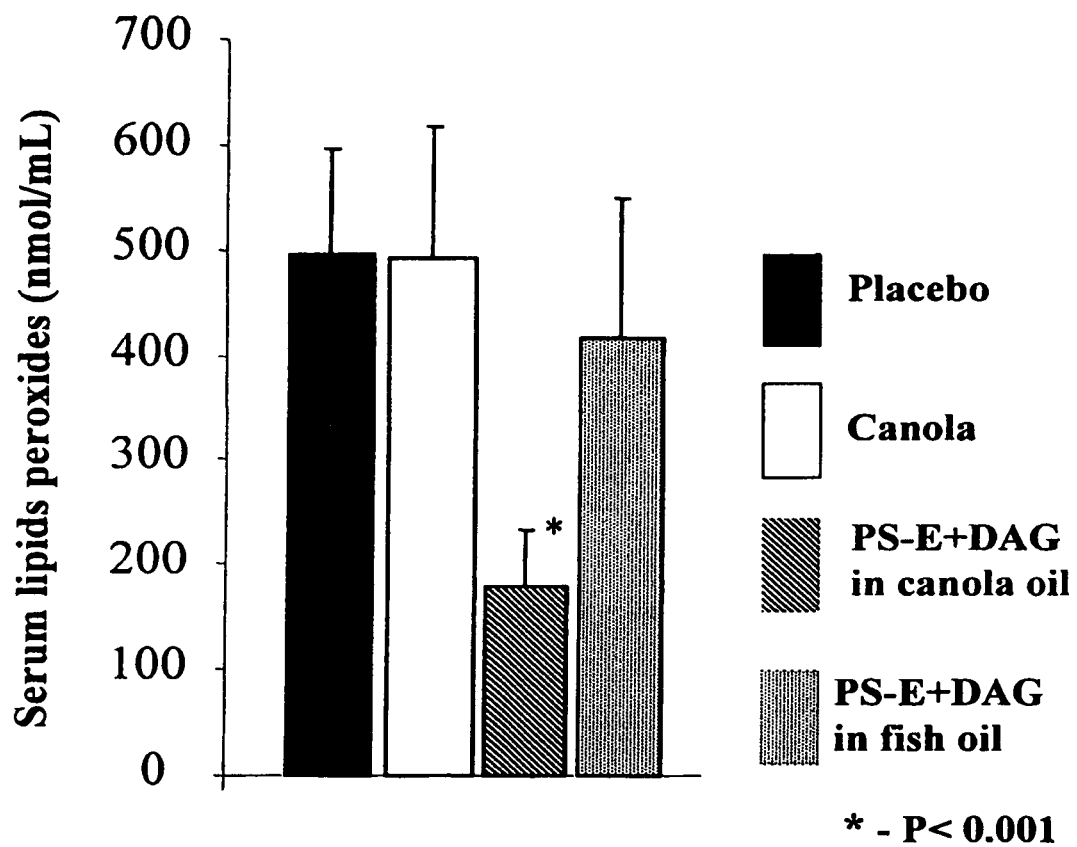

FIG. 5 shows that PSE+DAG in canola oil treatment resulted in a drastic and highly significant ($p<0.001$) reduction of the serum susceptibility to AAPH-induced oxidation by 63% (in comparison to placebo). PSE+DAG in fish oil demonstrated a similar tendency, reducing lipid peroxides by 16% in comparison with placebo. The different efficacy between these two matrices could be attributed, at least in part, to the well documented tendency of these polyunsaturated fatty acids towards generation of lipid peroxidation products.

FIG. 6 shows an interesting result. Whereas canola oil consumption induced a significant reduction in the levels of serum PON1 activity ($p<0.1$), which may be detrimental for atherosclerosis [Mackness, B. et al. [2003] *Circulation* 107: 2775-9], consumption of PSE+DAG in canola oil or in fish oil restored PON1 activity, to levels comparable of that of untreated (Placebo group) mice. Thus, consumption of PSE+DAG in canola oil and PSE+DAG in fish oil is beneficial for maintaining effective levels of PON1 activity.

FIG. 7 demonstrates that consumption of PSE+DAG in canola oil caused reduction of ox-LDL association (16%) and degradation (14%) ($p<0.05$), resulting in increased MPM abilities to sustain ox-LDL, which can be correlated to a decreased oxidation status, and to a larger extent, PSE+DAG in fish oil displayed a similar effect, also causing reduction of ox-LDL association (34%) and degradation (30%) ($p<0.001$). In contrast, canola oil consumption resulted in a slight increased (p value<0.05) of both ox-LDL association and degradation (4% and 11%, respectively, in comparison to placebo).

FIG. 8 shows that consumption of either PSE+DAG in canola oil or PSE+DAG in fish oil significantly reduced the oxidative status of $E^0$ mice macrophages ($p<0.0001$). PSE+DAG in fish oil reduced macrophages oxidative status by 34% in comparison to placebo, while PSE+DAG in canola oil reduced it by 29% in comparison to placebo. Thus, both PSE+DAG in fish oil and PSE+DAG in canola oil are effective in reducing the oxidative status of macrophages. Consistent with these results, in FIG. 9, the inventors show that, similarly, consumption of either PSE+DAG in fish oil or PSE+DAG in canola oil also significantly reduced the PMA-induced release of superoxide anions in macrophages ($p<0.05$).

Example 3

Human Study Comparing PSE+DAG Diet with Control

Change in Total Cholesterol Concentrations

Figure 10:
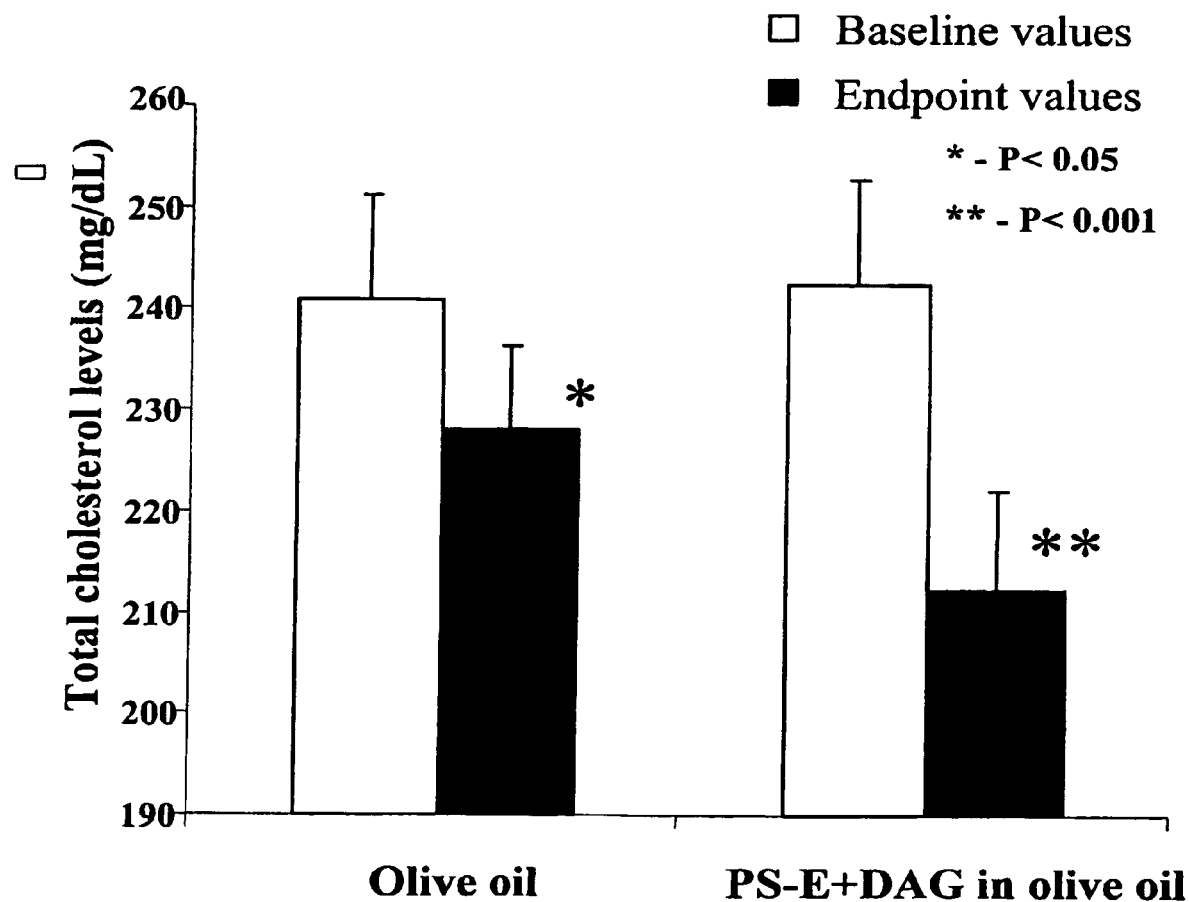

Supplementation of mildly overweight hypercholesterolemic subjects' diet with PSE+DAG demonstrated a distinct impact on total plasma cholesterol concentrations (P-value<0.0001; see FIG. 10). Compared to control MUFA based OA-enriched oil diet, PSE+DAG consumption induced a significantly higher hypocholesterolemia effect (−4% vs. −12%, respectively; P=0.03). In terms of absolute cholesterol concentrations reduction, the volunteers that consumed these diets reduced 13 mg/dL and 30 mg/dL; from initial average level of 240 mg/dL and 243 mg/dL to a final average levels of 228 mg/dL and 213 mg/dL, respectively. It must also be noted that this background diet, contained limited amount of cholesterol (not more than 80 mg/1000 kcal), which could also play part in the total cholesterol levels reduction effect. With respect to the American Heart Association (AHA) recommendations towards blood lipids levels [Expert Panel on Detection, Evaluation, and Treatment of High Blood Cholesterol in Adults (2001) *J.A.M.A.* 285:2486-2497], suggesting the desirable total cholesterol levels in healthy individuals to be below 200 mg/dL, the volunteers who consumed the vegetable-oil diet reduced 31% of the total cholesterol levels required to meet the target. However, following PS-E+DAG feeding the serum total cholesterol levels were markedly reduced towards these optimal level inasmuch as 71%.

Change in LDL-Cholesterol Concentrations

As shown in FIG. 11, the hypocholesterolemic effect of PS-E+DAG was more prominent, as expected, in the reduction of LDL cholesterol plasma levels (from baseline levels of 154±8 mg/dL to endpoint 135±7 mg/dL; P-value=0.0004; while control vegetable oil consumption resulted in a significant effect on reduction of LDL cholesterol concentrations; however to a somewhat lower extent (from baseline levels of 156±8 mg/dL to endpoint 148±7 mg/dL; P-value=0.051; see FIG. 11). Indeed, in a paired analysis of the percentages of change in the LDL-cholesterol concentrations after supplementation with the PSE+DAG mixture compared to those observed after control oil supplementation, a marked tendency was demonstrated (−11.91% versus −4.13%, respectively; P=0.058). These hypercholesterolemic overweight volunteers, fed for four weeks with control MUFA based OA-enriched oil diet or PSE+DAG followed by four weeks of washout and counter supplementation, reduced their blood LDL-c levels by 31% or 81%, respectively, with respect to AHA definition of LDL-C levels of 130 mg/dL as near to optimal levels.

Change in apoB Concentrations

Lipoproteins and their associated apolipoproteins, like LDL-c and apo B, reduction was reported following OA-enriched olive oil diet, as compared to high omega-6 enriched diet in diabetic type 2 patients [Madigan C., et al., (2000) *Diabetes care* 23:1472-1477]. Therefore, a significant reduction in these volunteers' apo B levels following base oil consumption was expected (from baseline values of 1.19±0.07 g/L to endpoint 1.13±0.05 g/L; P-value=0.016; FIG. 12). As previously shown for plant sterol esters spreads [Amundsen A L., et al. (2002) *Am. J. Clin. Nutr.* 76:338-344], a more pronounced effect was demonstrated following PS-E+DAG supplementation to these hypercholesterolemic volunteers (from baseline values of 1.21±0.06 g/L to endpoint 1.09±0.06 g/L; P-value=0.0002; FIG. 12). Moreover, a comparison of the reducing effect of PSE+DAG on endpoint apo B concentrations (−9.85%) to the one obtained by the control diet (−2.77%), suggested a statistically significant difference between these dietary treatments effects (P=0.022). Interestingly, Kondo and colleagues [Kondo A., et al. (2002) *J. Atheroscler. Thromb.* 9:280-287] suggested a strong correlation between oxidized-LDL and apo B concentrations, having a turning point at apo B levels above 1.15 g/L. Both diets, were shown to be beneficial in obtaining this anti-oxidant outcome, albeit PSE+DAG presenting a more potent effect.

Change in apoB/apoA Ratio

Apo B, apo A-I and the apo B/apo A-I ratio have been reported as better predictors of cardiovascular events than LDL-C and they even retain their predictive power in patients receiving lipid-modifying therapy [Walldius J. and Jungner I. (2004) *J. Intrn. Med.* 255:188-205]. As may be seen from FIG. 13, in addition to the aforementioned reduction in apo B levels, introducing PSE+DAG to the base MUFA-enriched diet resulted in marked and significantly reduced levels of apoB/apoA ratios (from baseline values of 0.89±0.05 to endpoint 0.84±0.05; P-value=0.047; while no comparable effect was obtained following control diet (from baseline values of 0.91±0.04 to endpoint 0.89±0.04; P-value=0.19; FIG. 13). No significant differences were observed between the effects of these treatments on apoB/apoA ratios in % change (−4.01% and −1.35%, respectively; P=0.22). Similar observations were reported following plant sterol or stanol esters spreads consumption [Amundsen A L., et al. (2002) id ibid; Hallikainen M A. et al. (2000) *J. Nutr.* 130:767-776].

Change in Lipoprotein (a) Levels

As shown in FIG. 14, hypercholesterolemic volunteers fed with control diet presented significantly elevated levels of Lp(a) (from baseline values of 0.18±0.03 g/L to endpoint 0.22±0.04 g/L; P-value=0.0003; FIG. 14). However, esterification of monounsaturated fatty acids to plant sterols in a DAG containing matrix (PS-E+DAG) maintained Lp(a) concentrations (from baseline values of 0.19±0.03 g/L to endpoint 0.19±0.03 g/L; P-value=0.41; FIG. 14).

Change in Triglycerides Levels

Recently, an elevated triglycerides concentration was suggested to be a univariate predictor of CVD. Specifically, 88 mg/dL increase in triglycerides levels was associated with a 14% increase in CVD risk in men and a 37% increase in women [Austin M A., et al. (1998) *Am. J. Cardiol.* 81:7B-12B]. Olive oil based diet was already demonstrated to induce a marked (10%) triglycerides levels reduction, comparing with an average American diet [Kris-Etherton P M., et al., (1999) *Am. J. Clin. Nutr.* 70:1009-1015]. Therefore, the reduction in the fasting triglycerides levels of the different diets was anticipated, as the base diet oil was OA-enriched (control diet from 191±32 mg/dL to 165±25 mg/dL, P-value=0.038 and PSE+DAG in olive oil 182±27 mg/dL to 155±22 mg/dL, P-value=0.031). The extent of the PSE+DAG effect on fasting triglycerides levels (−9.9%) was at least somewhat higher than what was obtained for control high oleic diet (−5.3%), which could also be appreciated from the difference in the median values of % of change (−10.4% and −3.7%, respectively). It should be also noted that the tested subjects were normolipidemic but presented elevated levels of LDL-C. It is well established [Normen L., et al. (2004) *Curr Med Chem Cardiovasc Hematol Agents* 2:1-12] that even potent dietary hypotriglyceridemic agents like fish oil demonstrate different effect in normolipidemic as opposed to hyperlipidemic subjects.

Change in Oxidative Stress Levels

Aviram and Eias [Aviram M. and Eias K. (1993) *Ann. Nutr. Metab.* 37:75-84] had demonstrated that in vitro incubation of LDL with copper ion in the presence of linoleic acid (LA) resulted with a 22% elevation of LDL oxidation, as opposed to marked dose-dependent inhibition of lipoprotein oxidation by pre-incubation with OA. Moreover, a recent study [Madigan C., et al., (2000) *Diabetes care* 23:1472-1477] suggested that, in type 2 diabetes, an OA-rich Mediterranean-type diet versus a LA-enriched diet may reduce the risk of atherosclerosis by decreasing the number of chylomicron remnant particles. In consistence, control diet, enriched with MUFA, demonstrated a mild tendency toward reducing the oxidative levels, as recorded using TBARS analysis (from baseline values of 1.11±0.48 mmol/L to endpoint 0.91±0.11 mmol/L; P-value=0.10; FIG. 15). Importantly, following PSE+DAG consumption there was a more pronounced and significant reduction in plasma oxidative stress levels (from baseline values of 1.01±0.21 mmol/L to endpoint 0.83±0.15 mmol/L; P-value=0.005; FIG. 15). These observations could be attributed in part to the aforementioned obtained indications for marked reduction of total cholesterol, LDL-C, apo B, and triglycerides while maintaining Lp(a) levels, which were previously shown to be correlated with elevated serum anti-oxidant capacity levels.

Example 4

Human Study Comparing Preparation A diet (Omega-3 Esters) with Fish Oil

Change in Total Cholesterol Concentrations

Hypercholesterolemic overweight volunteers were fed for four weeks with control diet (open squares) fish oil (closed squares) or Preparation A (hatched squares) followed by four weeks of washout and counter supplementation. Total cholesterol levels were tested at the beginning and at the termination of each phase as described in methods. Values represent mean±SEM of the percent of change in the total cholesterol concentrations in 21 patients. Statistical significance between the different treatments as found by ANOVA is P<0.05.

FIG. 16 presents the effects, of the dietary treatments on plasma total cholesterol concentrations in all patients (n=21) in the different phases. A substantial decrease (−8.45%; p-value=0.008) in total cholesterol concentrations was observed following the fish oil treatment, while control diet consumption induced a significant though smaller hypocholesterolemic effect (−4.40%; P-value=0.03). In terms of absolute cholesterol concentrations reduction, the volunteers that consumed these diets reduced 21 mg/dL and 13 mg/dL; from initial average level of 241 mg/dL and 240 mg/dL to a final average levels of 220 mg/dL and 228 mg/dL, respectively.

Change in LDL-Cholesterol Concentrations

Hypercholesterolemic overweight volunteers were fed for four weeks with fish oil (open squares) or Preparation A (closed squares) followed by four weeks of washout and counter supplementation. LDL-cholesterol levels were tested at the beginning and at the termination of each phase as described in methods, and the results are shown in FIG. 17. Values represent mean±SEM of the percent of change in LDL-cholesterol concentrations in 21 patients. Statistical significance between the fish oil and Preparation A as found by paired Student's t-test analysis is P<0.05.

As shown in FIG. 17, the hypocholesterolemic effect of Preparation A of the invention was more prominent, as expected, in the reduction of LDL cholesterol plasma levels (FIG. 17); while fish oil consumption resulted in an elevation of LDL cholesterol concentrations, compared to the reduction in LDL cholesterol obtained by the control diet. The esterification of fish oil with plant sterol esters attenuated the increasing effect of fish oil on LDL cholesterol (from 158 mg/dL to 144 mg/dL; P-Value=0.006). The percentages of change in the LDL-cholesterol concentrations after supplementation with the omega-3 esters mixture of the invention (Preparation A) were statistically different from those observed after fish oil supplementation (−8.04% versus −0.93%, respectively; P<0.05). A paired analysis of Preparation A effect on LDL-cholesterol compared to the control diet had demonstrated a marked tendency (8.04% versus 4.13%; P-value=0.15).

Change in apoB Concentrations

Hypercholesterolemic overweight volunteers were fed for four weeks with control diet (open squares) fish oil (closed squares) or Preparation A (hatched squares) followed by four weeks of washout and counter supplementation. Apolipoprotein B100 (apoB) levels were tested at the beginning and at the termination of each phase as described in methods. The results are shown in FIG. 18. Values represent mean±SEM of the percent of change in the apoB concentrations in 21 patients. Statistical significance between the different treatments as found by ANOVA is P<0.05.

As shown in FIG. 18, a comparison of the reducing effect of the omega-3 esters mixture of the invention (Preparation A) on endpoint apoB concentrations (−12.52%) to the ones obtained by un-reacted fish oil (−8.84%) or control diet (−2.27%), suggests a statistical significant between these dietary treatments effects (P=0.012).

Change in apoA/apoB Ratio

Hypercholesterolemic overweight volunteers were fed for four weeks with control diet (open squares) fish oil (closed squares) or Preparation A (hatched squares) followed by four weeks of washout and counter supplementation. Apolipoprotein B100 and Apolipoprotein A levels were tested at the beginning and at the termination of each phase as described in methods. The results are shown in FIG. 19. Values represent mean±SEM of the percent of change in the apoA to apoB ratio in 21 patients. Statistical significance between the different treatments as found by ANOVA is P<0.01.

As may be seen from FIG. 19, in addition to the change in apoB levels, when the omega-3 esters mixture of the invention (Preparation A) were compared to the fish oil and control diets, significant differences were observed between the effects of treatment on apoA/apoB ratios absolute changes (0.09, −0.01 and 0.02, respectively; P=0.039) and % change (8.45%, 0.35% and 2.20%, respectively; P=0.09) in apoA/apoB ratios.

Change in Total to HDL Cholesterol Ratio

Hypercholesterolemic overweight volunteers were fed for four weeks with control diet (open squares) fish oil (closed squares) or Preparation A (hatched squares) followed by four weeks of washout and counter supplementation. Total cholesterol and HDL-cholesterol levels were tested at the beginning and at the termination of each phase as described in methods. The results are shown in FIG. 20. Values represent mean±S.E.M of the percent of change in the total cholesterol to HDL-cholesterol ratio in 21 patients. Statistical significance between the different treatments as found by ANOVA is P<0.01.

As shown in FIG. 20, fish oil supplementation resulted in a tendency to increase the total/HDL cholesterol ratio (+3.5%; P-Value=0.15), apparently related to a decrease in HDL cholesterol levels (−10.94%; P-value=0.00003), while the control diet demonstrated only a negligible an insignificant increase in this key parameter (0.05; P-Value=0.72). However, when the omega-3 esters mixture of the invention (Preparation A) was consumed with the control diet, a significantly decreased (7.5%; P-Value=0.008) total/HDL cholesterol ratio was demonstrated (compared to fish oil and control diet; P-value=0.005; FIG. 20).

Changes in HDL Cholesterol Subfractions

Hypercholesterolemic mildly overweight volunteers were fed for four weeks with control diet (open squares) fish oil (closed squares) or Preparation A (hatched squares) followed by four weeks of washout and counter supplementation. $HDL_2$ (A) and $HDL_3$ (B) cholesterol levels in blood were measured at the beginning and at the termination of each phase as described. Results are shown in FIG. 21. Values represent mean±SEM of % of change in $HDL_2$ or $HDL_3$-cholesterol sub-fraction in 21 patients. Statistical significant as found by ANOVA for A (P-value<0.02) and B (P-Value<0.005).

As shown, feeding hypercholesterolemic subjects for a limited period with either control diet or fish oil had no effect on the $HDL_2$ subfraction levels (7.8% and −6.1%, respectively; P-value=0.33 and 0.45). However, supplementation with the omega-3 esters mixture of the invention (Preparation A) resulted with a marked elevation in $HDL_2$ levels (38.7%; P-value=0.007), which was shown to be significantly different than the control diet or fish oil treatment effects (P-value=0.022; FIG. 21A). The $HDL_3$ levels were reduced similarly by either the omega-3 esters mixture of the invention (Preparation A) or the fish oil (−13.1% and −12.7%, respectively; P-Value of 0.002 and 0.0005), but were unaffected by the control diet consumption (0.40%; P-Value=0.49), as shown in FIG. 21B.

Change in Fasting Triglycerides Concentrations

Hypercholesterolemic overweight volunteers were fed for four weeks with control diet (open squares) fish oil (closed squares) or Preparation A (hatched squares) followed by four weeks of washout and counter supplementation. Triglycerides levels were tested at the beginning and at the termination of each phase as described in methods. Results are shown in FIG. 22. Values represent mean±SEM of the level of plasma triglycerides concentrations in 21 patients. Statistical significance between the different treatments as found by ANOVA is P<0.0001.

Un-reacted fish oil decrease plasma fasting triglycerides by 37.1% (from 178 mg/dL to 97 mg/dL; P-value=0.007) while the comparable effect of the omega-3 esters mixture of the invention (Preparation A) was 42.9% decrease (from 165 mg/dL to 87 mg/dL; P-Value=0.00002); however there was only a mild tendency that suggests a difference between the effects of these supplementations (Student's t-test Paired analysis the P-Value=0.112). Comparing the effects of these supplements on fasting triglycerides levels to the rather mild effect of the control diet (−5.3%; P-Value=0.04) provides a statistically significant difference between the consumption of fish oil to olive oil (P-Value=0.0001; see FIG. 22).

Endpoint Postprandial Triglycerides Concentrations.

Hypercholesterolemic overweight volunteers were fed for four weeks with control diet (open squares) fish oil (closed squares) or Preparation A (hatched squares) followed by four weeks of washout and counter supplementation. Triglycerides levels were analyzed shortly after the meal at the termination of each phase as described in methods. Results are shown in FIG. 23. Values represent mean±SEM of the level of postprandial triglycerides concentrations in 21 patients. Statistical significance between the different treatments as found by ANOVA is P<0.01.

FIG. 23 shows the effect of the diets on postprandial triglyceride levels (FIG. 23). The lowest plasma triglyceride concentrations after consumption of a meal were detected in the subjects fed with the omega-3 esters mixture of the invention (135.6 mg/dL) compared with fish oil (159.1 mg/dL) and control diet (232.6 mg/dL) supplements (P-Value=0.002). Interestingly, the paired analysis between the un-reacted and the omega-3 esters mixture of the invention (Preparation A) demonstrated a notable tendency between these two supplements, though the levels of the EPA and DHA were identical (P-Value=0.09).

Change in CRP Concentrations

Hypercholesterolemic overweight volunteers were fed for four weeks with control diet (open squares) fish oil (closed squares) or Preparation A (hatched squares) followed by four weeks of washout and counter supplementation. CRP levels were analyzed at the beginning and the termination of each phase as described in methods. Results are shown in FIG. 24. Values represent mean±SEM of the level of CRP concentrations in 20 patients. Statistical significance between the different treatments as found by ANOVA is P<0.15.

The comparison of short-term consumption of control diet with or without fish oil or the omega-3 esters mixture of the invention (Preparation A) presented only a mild tendency towards altered effects (P-Value=0.151; see FIG. 24).

Endpoint Relative Risk According to Total/HDL Cholesterol and CRP Concentrations Hypercholesterolemic overweight volunteers were fed for four weeks with control diet (open squares) fish oil (closed squares) or Preparation A (hatched squares) followed by four weeks of washout and counter supplementation. Total cholesterol, HDL cholesterol and CRP levels were analyzed at the termination of each phase as described in methods. Total to HDL cholesterol ratio was calculated as described in methods, and Rifai and Ridker 2000 [Rifai and Ridker (2001) *Clin. Chem.*; 47:28-30] suggested algorithm was employed relative risk in the different phases calculation. Results are shown in FIG. 25. Values represent mean±SEM of the relative risk predicted values according to Rifai and Ridker 2000 as calculated for 21 patients. Statistical significance between the control diet or fish oil and the Preparation A as found by paired Student's t-test is 0.004 and 0.005, respectively.

Further correlations between the total to HDL-cholesterol ratio and CRP-levels remarkably indicate a reduced relative risk of CVD event prospective in the following ten years for the subjects which consumed the omega-3 esters mixture of the invention (Preparation A) (FIG. 25).

The invention claimed is:

1. An edible composition which comprises a mixture of esters of omega-3 long chain polyunsaturated fatty acids (omega-3 LC-PUFA), said mixture comprising (1) esters of omega-3 LC-PUFA with phytosterols or phytostanols or with both phytosterols and phytostanols and (2) esters of omega-3 LC-PUFA with glycerol, wherein the weight ratio of (2) to (1) in the mixture is from about 1.5:1 to about 1:9.

2. A mixture of claim 1, wherein said esters of LC-PUFA with glycerol are mono-, di- and/or triglycerides.

3. A method for reducing circulating atherogenic small-dense LDL particles, while maintaining a high proportion of HDL/LDL ratio, in a subject in need thereof which comprises administering to the subject an amount of the composition of claim 1 effective to reduce circulating atherogenic small-dense LDL particles in the subject.

4. A method for shifting a subject's HDL profile in the direction of larger and less dense particles and reducing the $HDL_3$ subfraction while increasing the level of $HDL_2$ subfraction which comprises administering to the subject an amount of the composition of claim 1 effective to shift the subject's HDL profile.

5. A method for attenuating or counteracting adverse effects of omega-3 fatty acids in the form of oils selected from elevated LDL cholesterol and increased total/HDL cholesterol ratio related to a decrease in HDL cholesterol levels in a subject in need thereof which comprises administering to the subject an amount of the composition of claim 1 effective to attenuate or counteract adverse effects of omega-3 fatty acids in the subject.

6. The composition of claim 1, wherein said mixture of esters of omega-3 LC-PUFA with glycerol is derived from an animal source, a plant source, an algae source or a microorganism source.

7. An orally administrable pharmaceutical or nutraceutical unit dosage capsule form comprising an edible composition which comprises a mixture of (1) esters of omega-3 LC-PUFA with glycerol and (2) esters of omega-3 LC-PUFA with phytosterols and phytostanols, wherein said unit dosage form contains from about 0.3 to about 0.8 gram omega-3 LC-PUFA, and wherein said unit dosage form provides at least 50% of the recommended daily intake (RDI) of phytosterols and 100% of the RDI of omega-3 LC-PUFA.

8. The pharmaceutical dosage capsule form of claim 7, wherein said capsule is a soft gel capsule.

9. The pharmaceutical dosage capsule form of claim 7, wherein said RDI of phytosterols is from about 0.4 g to about 0.8 g.

10. A method for reducing circulating atherogenic small-dense LDL particles, while maintaining a high proportion of HDL/LDL ratio, in a subject in need thereof which comprises administering to the subject an amount of the pharmaceutical dosage capsule form of claim 7 effective to reduce circulating atherogenic small-dense LDL particles in the subject.

11. A method for shifting a subject's HDL profile in the direction of larger and less dense particles and reducing the $HDL_3$ subfraction while increasing the level of $HDL_2$ subfraction which comprises administering to the subject an amount of the pharmaceutical dosage capsule form of claim 7 effective to shift the subject's HDL profile.

12. A method for attenuating or counteracting adverse effects of use of omega-3 fatty acids in the form of oils selected from elevated LDL cholesterol and increased total/HDL cholesterol ratio related to a decrease in HDL cholesterol levels in a subject in need thereof which comprises administering to the subject an amount of the pharmaceutical dosage capsule form of claim 7 effective to attenuate or counteract adverse effects of omega-3 fatty acids in the subject.

13. A method of treatment of metabolic syndrome and related conditions, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

14. The method of claim 13, wherein said effective dose is comprised in a soft gelatine capsule, said method comprising administering said capsule to said patient twice daily.

15. A method of reducing circulating atherogenic small-dense LDL particles, while maintaining a high proportion of HDL/LDL ratio, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

16. The method of claim 15, wherein said effective dose is comprised in a soft gelatine capsule, said method comprising administering said capsule to said patient twice daily.

17. A method of shifting the HDL profile in the direction of larger and less dense particles, particularly reducing the $HDL_3$ subfraction while increasing the level of $HDL_2$ subfraction, said method comprising administering a therapeutically effective dose of an edible mixture of esters of LC-PUFA or compositions comprising thereof to a subject in need, wherein said mixture comprises esters of LC-PUFA with phytosterols and/or phytostanols and esters of LC-PUFA with glycerol, wherein the weight ratio of said LC-PUFA glycerol esters to their esters with phytosterol or phytostanol is from about 19:1 to about 1:9.

18. The method of claim 17, wherein said effective dose is comprised in a soft gelatine capsule, said method comprising administering said capsule to said patient twice daily.

19. A method for reducing triglycerides in a subject in need thereof, wherein the reduction of plasma levels of triglycerides in said subject is greater than the reduction achieved by administration of a corresponding amount of fish oil, which comprises administering to the subject an amount of the composition of claim 1, effective to reduce triglycerides in the subject, wherein the omega-3 LC-PUFA residues in the esters of omega-3 LC-PUFA with glycerol and in the esters of omega-3 LC-PUFA with any phytosterols and phytostanols present in the composition correspond to the fatty acid residues of fish oil.

20. The method of claim 13, wherein the LC-PUFA residues in the esters of LC-PUFA with glycerol and in the esters of LC-PUFA with phytosterols and/or phytostanols correspond to the fatty acid residues of fish oil, and wherein the reduction of plasma levels of triglycerides is greater than reduction achieved by administration of fish oil.

21. The composition of claim 1 further comprising free phytosterols, free phytostanols, or both free phytosterols and free phytostanols.

\* \* \* \* \*